(12) United States Patent
Longaker et al.

(10) Patent No.: US 11,529,391 B2
(45) Date of Patent: Dec. 20, 2022

(54) REVERSING DEFICIENT HEDGEHOG SIGNALING RESTORES DEFICIENT SKELETAL REGENERATION

(71) Applicant: The Board of Trustees of the Leland Stanford Junior University, Stanford, CA (US)

(72) Inventors: Michael T. Longaker, Atherton, CA (US); Irving L. Weissman, Stanford, CA (US); Ruth Tevlin, Stanford, CA (US); Charles K. F. Chan, Redwood City, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 0 days.

(21) Appl. No.: 16/475,353

(22) PCT Filed: Jan. 8, 2018

(86) PCT No.: PCT/US2018/012823
§ 371 (c)(1),
(2) Date: Jul. 1, 2019

(87) PCT Pub. No.: WO2018/129470
PCT Pub. Date: Jul. 12, 2018

(65) Prior Publication Data
US 2019/0336575 A1 Nov. 7, 2019

Related U.S. Application Data

(60) Provisional application No. 62/444,176, filed on Jan. 9, 2017.

(51) Int. Cl.
*A61K 38/18* (2006.01)
*A61K 38/17* (2006.01)
*A61P 19/00* (2006.01)
*A61P 3/10* (2006.01)
*C07K 14/435* (2006.01)
*C07K 14/475* (2006.01)

(52) U.S. Cl.
CPC ............ *A61K 38/1709* (2013.01); *A61P 3/10* (2018.01); *A61P 19/00* (2018.01); *C07K 14/435* (2013.01)

(58) Field of Classification Search
CPC ........ A61K 38/1709; A61P 19/00; A61P 3/10; C07K 14/435
See application file for complete search history.

(56) References Cited

U.S. PATENT DOCUMENTS

| | | | |
|---|---|---|---|
| 3,773,919 A | 11/1973 | Boswell et al. | |
| 4,530,840 A | 7/1985 | Tice et al. | |
| 4,622,219 A | 11/1986 | Haynes et al. | |
| 4,767,628 A | 8/1988 | Hutchinson | |
| 4,891,225 A | 1/1990 | Langer et al. | |
| 6,132,765 A * | 10/2000 | DiCosmo | A61L 27/54 424/450 |
| 6,271,363 B1 * | 8/2001 | Ingham | A01K 67/0275 435/69.1 |
| 6,683,192 B2 * | 1/2004 | Baxter | A61P 15/08 549/32 |
| 8,853,266 B2 * | 10/2014 | Dalton | A61K 31/675 514/522 |
| 2005/0171015 A1 * | 8/2005 | Crabtree | A61K 38/465 514/9.4 |

FOREIGN PATENT DOCUMENTS

WO 9725563 A1 7/1997

OTHER PUBLICATIONS

Kelly et al. "The Use of a Surgical Grade Calcium Sulfate as a Bone Graft Substitute". 2001. Clinical Orthopaedics and Related Research. No. 382, pp. 42-50 (Year: 2001).*
Shimoyama et al. "Ihh/Gli2 Signaling Promotes Osteoblast Differentiation by Regulating Runx2 Expression and Function". 2007. Molecular Biology of the Cell, vol. 18, 2411-2418 (Year: 2007).*
Guan et al. "Sonic hedgehog alleviates the inhibitory effects of high glucose on the osteoblastic differentiation of bone marrow stromal cells". 2009. Bone, 45, 1146-1152 (Year: 2009).*
Edwards et al. "Sonic hedgehog gene-enhanced tissue engineering for bone regeneration". Gene Therapy (2005) 12, 75-86. (Year: 2005).*
Zou et al. "Mesenchymal stem cells overexpressing Ihh promote bone repair". Journal of Orthopaedic Surgery and Research 2014, 9:102. (Year: 2014).*
Bianco et al. "Postnatal Skeletal Stem Cells" 2006, Elsevier Inc.vol. 419 [6] pp. 117-148 (Year: 2006).*
Umpierrez et al. "Treatment of Diabetic Ketoacidosis With Subcutaneous Insulin Aspart" Diabetes Care 27:1873-1878, 2004. (Year: 2004).*
Sopyan et al. "Porous hydroxyapatite for artificial bone applications"; Science and Technology of Advanced Materials 8 (2007) 116-123. (Year: 2007).*
Keats et al in "Switch from Canonical to Noncanonical Wnt Signaling Mediates High Glucose-Induced Adipogenesis"; Cells 2014;32:1649-1660 (Year: 2014).*
Keats and Khan, "Unique Responses of Stem Cell-Derived Vascular Endothelial and Mesenchymal Cells to High Levels of Glucose", PLoS ONE 7(6): e38752 (Year: 2012).*
Tevlin et al., "Diminished Recruitment of Resident Skeletal Progenitor Cells in Diabetic Fracture Healing," Plastic and Maxillofacial Surgery (219)3: Journal of the American College of Surgeons, Supplement, s82, Sep. 1, 2014.*

(Continued)

*Primary Examiner* — Joanne Hama
*Assistant Examiner* — Jon M Lockard
(74) *Attorney, Agent, or Firm* — Pamela J. Sherwood; Bozicevic, Field & Francis LLP

(57) ABSTRACT

Methods and compositions are provided for the therapeutic use of hedgehog agents, for enhancing bone growth and regeneration in diabetic or pre-diabetic patients, including repair following injury, osseointegration of implants, and the like. In some embodiments of the invention, the compositions are administered locally, e.g. by injection or implantation at the site of an injury.

9 Claims, 50 Drawing Sheets

(56) References Cited

OTHER PUBLICATIONS

Marecic et al., "Response of Skeletal Progenitor Cells to Fracture Injury in a Mouse Model," Journal of the American College of Surgeons, Surgical Forum Abstracts, S86, Sep. 1, 2014.*
Tevlin et al., "Impairment in Fracture Healing in a Mouse Model of Type 2 Diabetes Is Driven by Skeletal Stem Cell Niche Dysregulation," Journal of the American College of Surgeons, Scientific Forum Abstracts, vol. 221, No. 4S1, Oct. 2015.*
Marecic et al., "Identification and Characterization of an Injury-Induced Skeletal Progenitor," PNAS 112(32):9920-9925, Aug. 11, 2015.*
Walmsley et al., "Nanotechnology in Bone Tissue Engineering," Nanomedicine: Nanotechnology, Biology, and Medicine (11):1253-1263 (2015) (Year: 2015).*
Tevlin et al., "Stem and progenitor cells: advancing bone tissue engineering," Drug Deliv. and Transl. Res. (2016) 6:159-173 (Year: 2015).*
Tevlin et al., "Skeletal Stem Cell Niche Aberrancies Underlie Impaired Fracture Healing in a Mouse Model of Type 2 Diabetes," Plastic and Reconstructive Surgery. 136(4S Suppl):73 (Year: 2015).*
Parisi-Amon et al., "Protein-Nanoparticle Hydrogels That Self-assemble in Response to Peptide-Based Molecular Recognition," ACS Biomaterials Science & Engineering, 3(5):750-756, Aug. 19, 2016.*
Chan et al., "Lectins bring benefits to bones," eLife Skeletal Stem Cells; 5:e22926 (Year: 2016).*
Tevlin et al., "Pharmacological rescue of diabetic skeletal stem cell niches," Science Translational Medicine, vol. 9, Issue 372 pp. 1-9, Jan. 11, 2017.*
Murphy et al., "The Role of Skeletal Stem Cells in the Reconstruction of Bone Defects," J Craniofac Surg. 28(5): 1136-1141 Jul. 2017.*
Tevlin et al., "Pharmacological rescue of diabetic skeletal stem cell niches," Supplemental Materials (Year: 2017).*
Kulkarni et al. (1966) "Polylactic acid for surgical implants" Arch. Surg. 93: 839.
Das et al. (2013) "Hedgehog agonist therapy corrects structural and cognitive deficits in a Down syndrome mouse model" vol. 5, Issue 201, pp. 201ra120.
Friedler et al. (2000) "Development of a functional backbone cyclic mimetic of the HIV-1 Tat arginine-rich motif" No. 31 pp. 23783-23789.

* cited by examiner mSSC-dependent bone healing is impaired in diabetic mice.

Mechanical Strength Testing i)

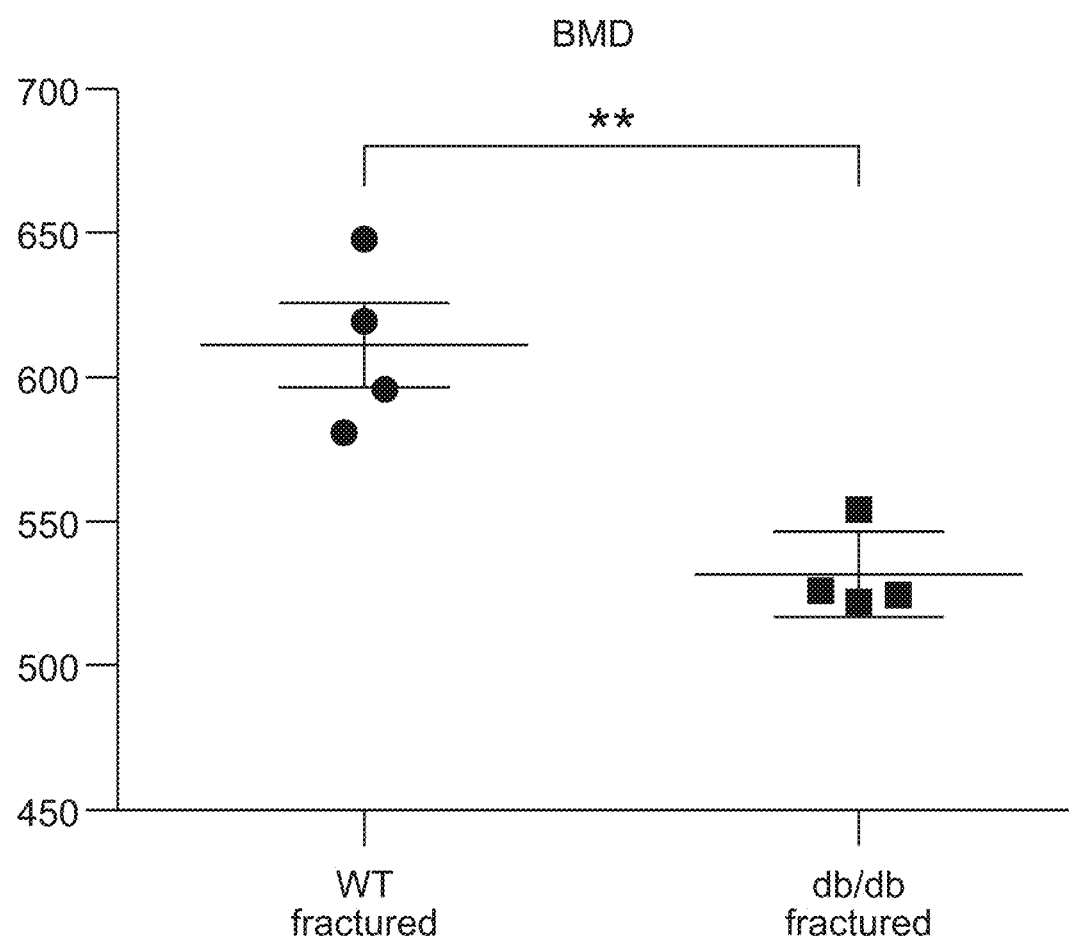

iii)

mSSC-dependent bone healing is impaired in diabetic mice.

top)

bottom)

top)

bottom)

left)

right)

Altered mSSC skeletogenic activity is cell-extrinsic in diabetic mice.

WT or DB mSSCs in WT environment

WT mSSCs in WT or Db environment

Differential hedgehog signaling occurs in diabetic skeletal niches after fracture.

WT control

WT + XL 139
100 nM

WT + XL 139
1000 nM

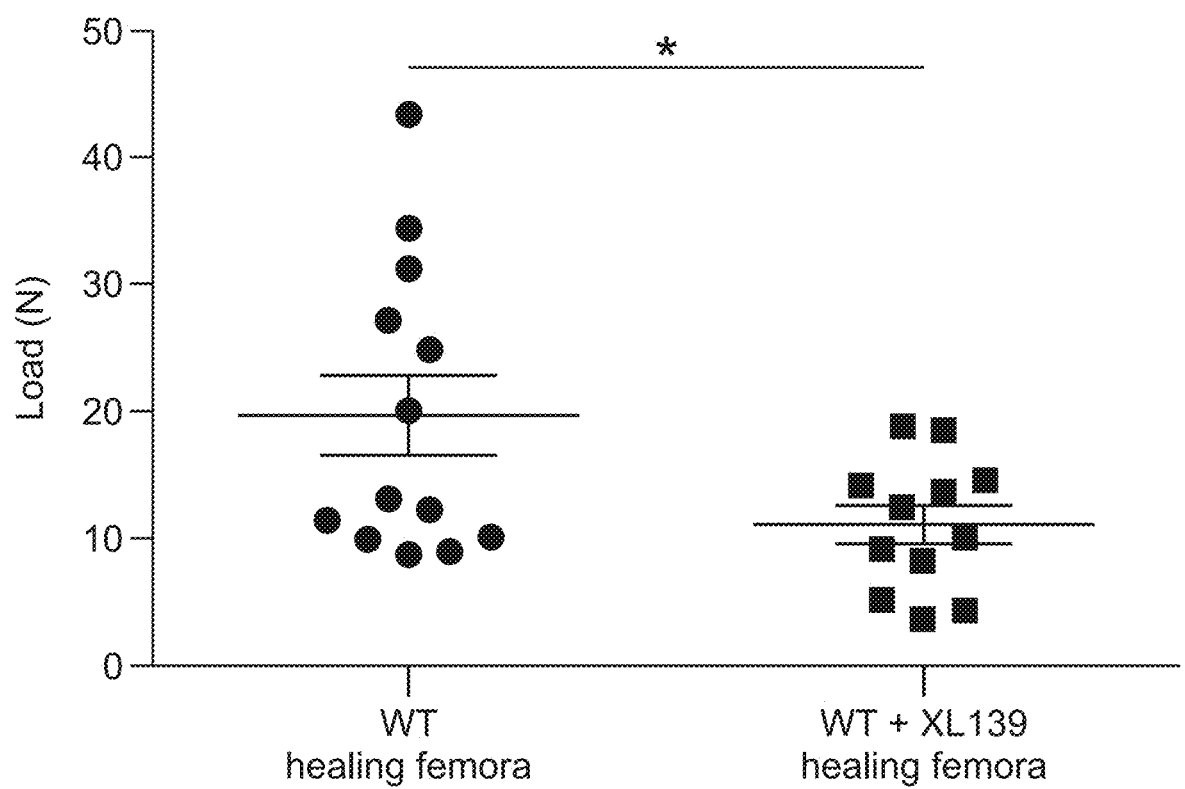

Indian hedgehog and Gli1 expression are repressed in diabetic human skeleton progenitors.

Area of cartilage degeneration

Local delivery of Ihh restores mSSC's functional response to injury.

left)

right)

left)

right)

Local delivery of Ihh restores mSSC's functional response to injury.

mSSC fracture

BCSP fracture

Impaired mSSC- and BCSP-mediated bone healing is consistent in multiple mouse models of DM.

Prior to fracture induction

Circulating IL-1b is elevated in both uninjured and injured Db mice.

Local delivery of *Ihh* restores impaired bone healing in Db mice.

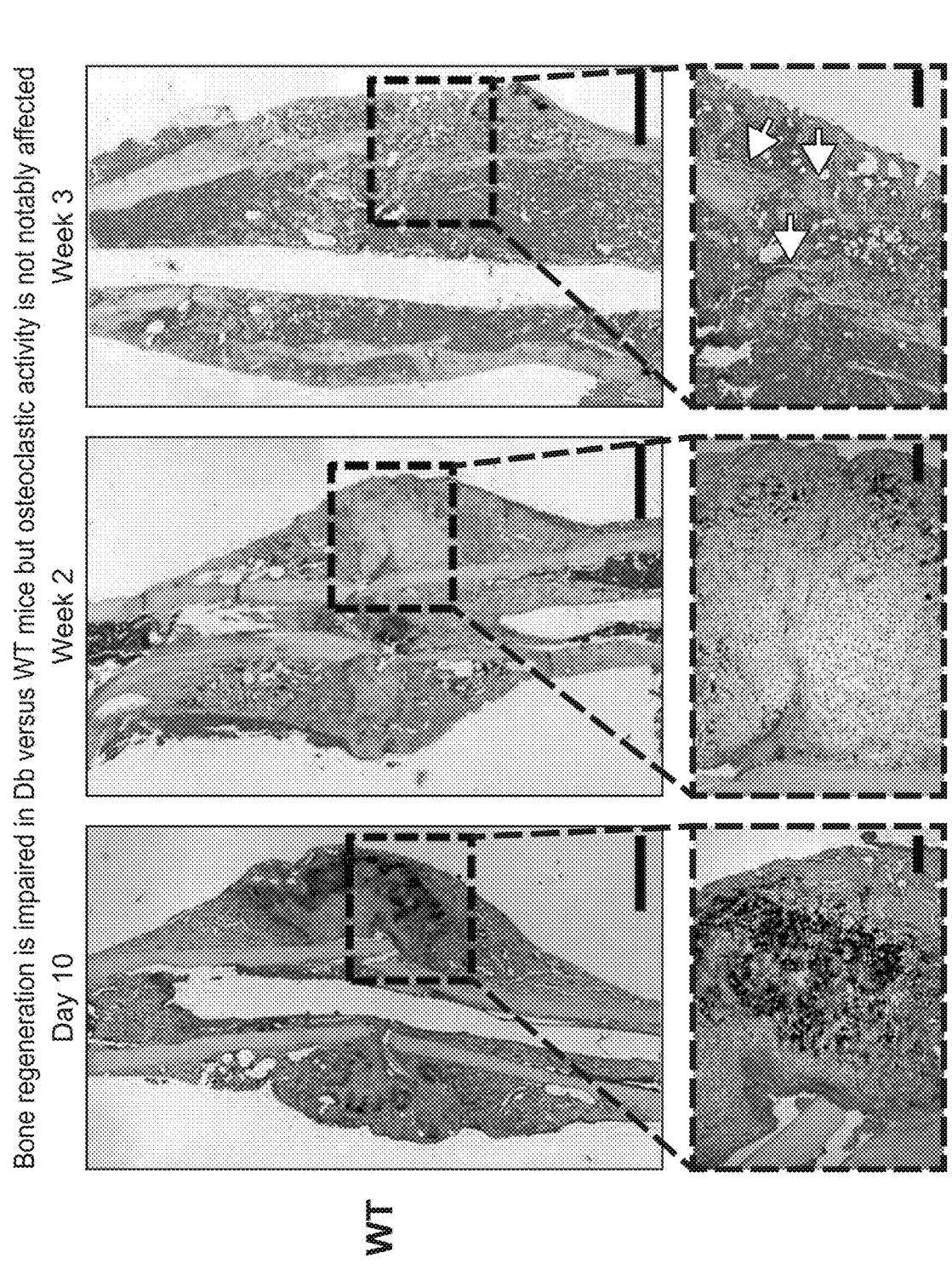

Bone regeneration is impaired in db/db versus WT mice but osteoclastic activity is not notably affected Week 2

Week 3

Week 4

WT

Neutralization of TNFα signaling in Db serum restores Ihh expression in co-cultured mSSC.

REVERSING DEFICIENT HEDGEHOG SIGNALING RESTORES DEFICIENT SKELETAL REGENERATION

CROSS-REFERENCE TO RELATED APPLICATIONS

This application is a 371 of International Application Serial No. PCT/US2018/012823, filed on Jan. 8, 2018, which claims priority to U.S. Provisional Patent Application Ser. No. 62/444,176, filed Jan. 9, 2017, the contents of each of which is incorporated herein by reference.

STATEMENT REGARDING FEDERALLY SPONSORED RESEARCH

This invention was made with Government support under contracts AG049958, DE021683, and HL099776 awarded by the National Institutes of Health. The Government has certain rights in the invention.

BACKGROUND OF THE INVENTION

Diabetes mellitus (DM) is a chronic metabolic disease with high blood glucose levels.

Diabetes results from deficits in the production of insulin or deficit insulin resistance coupled with insufficient insulin production. Type 1 diabetes mellitus (T1DM) is due to the lack of insulin production by the pancreas and requires daily administration of insulin. It is typically caused by destruction of pancreatic β-cells of autoimmune etiology. Type 2 diabetes mellitus (T2DM) is characterized by the inability to use insulin efficiently, referred to as insulin resistance combined with an inability to produce a sufficient amount of insulin to overcome the insulin resistance. Diabetes mellitus often leads to serious complications that affect the heart, blood vessels, eyes, kidneys, and nerves. It has also been increasingly recognized that diabetes adversely affects bone health.

High levels of glucose contribute to diabetic complications by inducing stress at the cellular level, glycating proteins that lead to the formation of advanced glycation endproducts, increasing production of reactive oxygen species, and enhancing expression of cytokines such as tumor necrosis factor. In diabetic humans and animals there is increased production of inflammatory mediators by macrophages in adipose tissue leading to increased systemic inflammation, which among other factors contributes to insulin resistance. Diabetic conditions such as high glucose levels, increased formation of advanced glycation endproducts and increased generation of ROS lead to greater expression of inflammatory cytokines at the local level when tissues are perturbated by events such as wounding.

Pro-inflammatory mediators including TNF-α, IL-1β, IL-6 and IL-18 are increased locally in diabetes mellitus and are thought to contribute to diabetic complications. Diabetics have difficulty in down regulating inflammation once induced. Increased levels of TNF may limit the capacity of diabetics to down regulate other inflammatory genes and increase apoptosis, which has been shown to reduce bone coupling in diabetic animals.

During perturbation diabetes increases and prolongs inflammation, which may lead to enhanced osteoclastogenesis. Diabetes increases osteoclast formation in a number of conditions including periodontal disease, fracture healing and osteoporosis. Diabetes-increased osteoclasts may pertain to situations where bone is challenged by injury or inflammation rather than basal levels. Diabetes leads to increased RANKL/OPG ratios and TNF levels that contribute to greater bone resorption. In humans, the ratio of RANKL/OPG and TNF levels are increased in poorly controlled diabetics. Fatty acid levels in diabetics may also contribute to increased osteoclastogenesis. The capacity to resolve inflammation is an important aspect of limiting bone resorption as shown by diminished bone loss in animals treated with resolvins or by use of TNF inhibitors.

Diabetic fracture is a significant co-morbidity of both type I and type II diabetes and is characterized by microarchitectural changes that decrease bone quality. Meta-analysis shows a consistent pattern of increased risk of fracture in men and women and in studies conducted in the United States and Europe. For example, the relative risk of hip fracture is increased 6-7 fold for individuals with T1DM, which is considerably higher than the increased risk (1.4-1.7 fold) in T2DM. The fracture risk of T1DM increases because of a decrease of bone mineral density (BMD), which is linked to impaired bone formation that may be linked to a deficiency of insulin and insulin-like growth factor-1 (IGF-1). T2DM is often characterized by normal or high BMD. Diabetes may be associated with a reduction of bone strength that is not reflected in the measurement of BMD, which results in high risk of fracture.

Healing of fractures in diabetic patients is prolonged by 87% and has a 3.4 fold higher risk of complications including delayed union, non-union, redislocation or pseudoarthrosis. Clinical studies in humans indicate that diabetes delays fracture healing. A study of spontaneously diabetic animals revealed that diabetic fracture healing was characterized by decreased bone apposition and mineralization. The reparative phase of bone fracture healing is initiated by proliferation and chondroblastic differentiation of periosteal precursor cells resulting in a hyaline cartilage callus around the wounded bone. Imbalances in chondrocyte apoptosis, premature removal of cartilage, reduced osteoblast differentiation and function and alterations in vascularization have been shown to affect the transition from cartilage to bone. Supernormal osteoclast activity disturbs remodeling of the osseous callus. It has been proposed in the art that any of insulin insufficiency, hyperglycemia and oxidative stress are mechanisms that affect fracture healing in T1DM and T2DM. They may reduce osteoblast differentiation, increase osteoclast activity, and alter apoptosis of chondrocytes and osteoblasts to interfere with fracture healing in diabetic patients.

T1DM and T2DM both increase fracture risk and have several common mechanisms including increased AGE formation, increased ROS generation, and increased inflammation. These factors affect osteoblasts and osteoclasts. Both humans and animal models of T1DM and T2DM display impaired fracture healing although T1DM patients have a greater risk of developing fractures. Moreover, animals with T1DM and T2DM exhibit impaired bone formation under conditions of perturbation such as bacteria induced periodontal bone loss and bone fracture healing.

Developing biologically based methods for restoring skeletal healing deficiencies related to diabetes is of great clinical interest.

SUMMARY OF THE INVENTION

A specific signaling deficiency underlying poor fracture healing in the diabetic skeletal stem cell niche is identified, and demonstrated to be reversed by exogenous delivery of an agent that provides for Hedgehog activity, leading to restoration of normal levels of bone regeneration. It is shown herein that agents that provide hedgehog activity for this purpose may include, without limitation, native or modified hedgehog proteins; antibodies that bind to and activate a hedgehog pathway protein, e.g. smoothened, patched, etc.; small molecules that are agonists of smoothened or patched; and the like. Specific skeletal stem cell niche-related abnormalities that impair skeletal repair are present in diabetic patients. This deficiency can be reversed by targeted delivery of a hedgehog agent to the fracture site, for example using a sustained release formulation such as a hydrogel. In the presence of exogenously applied hedgehog activity the injury-induced expansion and osteogenic potential of skeletal stem cells is restored, culminating in the rescue of diabetic bone healing. The methods provided herein can correct deficient skeletal healing in diabetic patients for a variety of applications, from repair of skeletal fractures, to securing bone or teeth implants.

In one embodiment a method is provided for promoting bone healing in a diabetic patient in need thereof by locally administering a therapeutically effective amount of hedgehog agent to the patient. Another aspect relates to the use of a hedgehog agent in the manufacture of a medicament for accelerating bone healing in a diabetic patient in need thereof, which medicament is characterized by comprising a therapeutically effective amount of hedgehog agent for localized administration. An additional aspect provides a drug delivery device, which comprises a hedgehog agent and a pharmaceutically acceptable carrier, wherein the device is adapted for localized administration of the agent to a patient in need thereof.

In some embodiments the hedgehog agent is a hedgehog protein. The hedgehog protein may be a human protein, or a variant or active fragment thereof. In some embodiments the hedgehog protein is sonic hedgehog. In some embodiments the hedgehog protein is indian hedgehog. In other embodiments the hedgehog agent is a small molecule agonist.

In one embodiment, the patient is afflicted with a bone condition selected from bone fracture, bone trauma, arthrodesis, and a bone deficit condition associated with post-traumatic bone surgery, post-prosthetic joint surgery, post-plastic bone surgery, post-dental surgery, bone chemotherapy treatment, congenital bone loss, post traumatic bone loss, post surgical bone loss, post infectious bone loss, allograft incorporation or bone radiotherapy treatment.

In an embodiment, the hedgehog agent is delivered via an hedgehog agent delivery system. In one embodiment, the hedgehog agent delivery system includes at least one biocompatible carrier or matrix. In another embodiment, the biocompatible carrier includes poly-lactic acid, poly-glycolic acid, copolymers of poly-lactic acid or poly-glycolic acid. In yet another embodiment, the biocompatible carrier includes at least one bioerodible fatty acid or a metal salt of a fatty acid. In one embodiment the biocompatible carrier is a hydrogel, for example a poly(ethylene glycol) hydrogel. In yet another embodiment, the hedgehog agent delivery system includes an article for implantation. In an additional embodiment, the hedgehog agent delivery system includes a coating on an article for implantation.

In another embodiment, the carrier comprises porous or non-porous calcium phosphate, porous or non-porous hydroxyapatite, porous or non-porous tricalcium phosphate, porous or non-porous tetracalcium phosphate, porous or non-porous calcium sulfate, or a combination thereof. The delivery system may further comprise a bioactive bone agent, including without limitation peptide growth factors, anti-inflammatory factors, pro-inflammatory factors, inhibitors of apoptosis, MMP inhibitors, bone catabolic antagonists, etc. diabetic mice are labeled as being in the right column and WT mice are labeled as being in the left column in FIG. 1(C).

The hedgehog agent may be delivered directly to the site for skeletal regeneration. The hedgehog agent may be provided immediately before, during or after the implant is introduced, shortly following a fracture or bone trauma, etc., and in some embodiments is delivered within 1, 2, 3, 4, 5, 6, 7 days following introduction. The hedgehog agent may be transiently provided over a short, defined period of time, for example as a localized implant releasing an active agent for a short period of time, e.g. not more than about 7 days, not more than 6 days, not more than 5 days, not more than 4 days, not more than 3 days, and the like.

In some embodiments of the invention an individual selected for treatment has metabolic syndrome. In some embodiments an individual selected for treatment has type I diabetes. In some embodiments an individual selected for treatment has type II diabetes. In embodiments an individual is tested for indicia of diabetes or metabolic syndrome prior to treatment, including without limitation testing insulin levels, blood sugar levels, hemoglobin A1c levels and the like, as known in the art.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

(FIG. 1A) Schematic representation of femoral fracture creation and assessment by Mechanical Strength Testing (MST) at post-fracture week 4. (FIG. 1B) Maximal load (Newtons, N) to fracture of uninjured and healing femora from $db_{LR}$ (red) versus WT (blue) mice, as assessed by MST. n=5. (FIG. 1C) (i) Representative micro-computed tomographic images show trabecular bone of healing femora from $db_{LR}$ (right column) or WT (left column) mice. The area outlined in the top row is magnified to show trabecular spaces (bottom row, red arrows). Top scale bar, 500 µm; bottom scale bar, 100 µm. (ii) Bone mineral density comparison of WT (left) and $db_{LR}$ fractures. (iii) Post-fracture scan of WT (left) and $db_{LR}$ fractures. (iv) Assessment of bone volume/total volume (BV/TV) of healing bone from WT or $db_{LR}$ mice (FIG. 1D) Illustration of mSSC lineage hierarchy. Mouse skeletal stem cell (mSSC); Pre-bone cartilage, stromal progenitor (pre-BCSP); Bone, cartilage, stromal progenitor (BCSP); Pro-chondrogenic cell (PCP); Thy+ osteogenic progenitor (Thy); B-cell lymphocyte stromal progenitor (BLSP); 6C3+ stromal progenitor (6C3); Hepatic leukemia factor expressing cell (HEC). (FIG. 1E) Schematic representation of stem and progenitor cell isolation. mSSCs and BCSPs were isolated from injured whole femora and dissected calluses at different post-fracture timepoints using fluorescence-activated cell sorting (FACS). (FIG. 1F) FACS plots show the frequencies of mSSCs and BCSPs in whole post-fracture day 7 calluses of $db_{LR}$ (bottom row) versus WT (top row) mice. (FIG. 1G) Absolute cell numbers of mSSCs (top graph) or BCSPs (bottom graph) in whole calluses harvested at different timepoints from $db_{LR}$ (red) versus WT (blue) mice. n=5 per group. (FIG. 1H)

Respective population percentages of BrdU-labeled mSSCs or BCSPs from post-fracture day 3 calluses of $db_{LR}$ (red) versus WT (blue) mice. db=$db_{LR}$ mice. n=5. (FIG. 11) Respective population percentage of annexin V expression on mSSCs from post-fracture day 7 calluses of $db_{LR}$ (red) versus WT (blue) mice. FMO=Full Minus One stain. Statistical analyses: unpaired two-tailed t-test. Results are depicted as mean±SEM; *p<0.05, p<0.01, **p<0.0001. "db" denotes $Lepr_{db}$ ($db_{LR}$) mice.

(FIG. 2A) Schematic representation of parabiotic pairing, femoral fracture creation, and assessment of healing femora using MST. Parabionts were rested for 4 weeks prior to further testing to ensure blood chimerism. Femoral fractures were fixed with an intramedullary pin (omitted for clarity). (FIG. 2B) A representative FACS analysis confirming blood chimerism in parabiotic pairs is shown. Blood chimerism was confirmed after 4 weeks of parabiosis by observing WT green fluorescent protein expressing (GFP+) (green boxes) cells in non-fluorescent $db_{LR}$ mice. (FIG. 2C) Blood glucose levels of each mouse in a chimeric pair are shown at post-parabiosis week 8. Parabiosis does not change the glycemic control of $db_{LR}$ or WT mice in WT/$db_{LR}$ chimeric pairs. n=5 per group. (FIG. 2D) MST analysis of healing femora harvested from each parabiotic pair shows that a non-diabetic circulation increases the strength of $db_{LR}$ femora but does not restore it to WT levels. n=5 per group.

(FIG. 3A) Schematic representation of kidney capsule transplantation assays. FACS-sorted mSSCs or BCSPs ($2 \times 10^4$) from the calluses of WT or $db_{LR}$ mice (top sequence) or the appendicular skeleton of P3 mice (bottom sequence) were transplanted into non-diabetic, immunodeficient (top) or WT or $db_{LR}$ (bottom) mice. Heterotopic skeletal grafts were excised after 1 month for histological analysis. (FIG. 3B) Left Section: Representative micrographs of grafts produced by mSSCs (i) or BCSPs (ii) from WT (top row) or $db_{LR}$ (bottom row) mice. There was no difference in graft size (left column, scale bar, 1 mm) or tissue composition (right column, scale bar, 200 μm). (FIG. 3C) Right Section: Grafts produced by P3 WT mSSCs (i) and BCSPs (ii) in WT (top row) or $db_{LR}$ (bottom row) mice show no difference in size (left column, scale bar, 1 mm), but grafts produced in $db_{LR}$ mice have decreased bone and persistent cartilage content, as shown by Movat's Pentachrome stain (right column, red arrows; yellow=bone, blue=cartilage, brown=marrow, red=kidney tissue; scale bar, 200 μm). Statistical analyses: unpaired two-tailed t-test. Results are depicted as mean±SEM; *p<0.05, ***p<0.001. "db" denotes $Lepr_{db}$ ($db_{LR}$) mice.

FIG. 4A-4G. Differential hedgehog signaling occurs in diabetic skeletal niches after fracture. (FIG. 4A) Heat map showing relative gene expression of skeletogenic factors in mSSCs and BCSPs from uninjured femora (left columns) or calluses (right columns) of WT versus $db_{LR}$ mice. Genes related to hedgehog (Hh) signaling (top rows) and skeletal development, growth, and repair (bottom rows) are shown. Differential gene expression was seen for Hh signaling factors, including Ihh, Smo, and Gli1 (black arrows). Blue denotes low expression; red denotes high expression. (FIG. 4B) Relative protein levels of Ihh in mSSCs from post-fracture day 7 calluses of $db_{LR}$ (red) versus WT (blue) mice. Western blot quantification was determined by densitometry analysis. n=3. (FIG. 4C) Heat map showing relative gene expression of Hh signaling factors in mSSCs from postfracture day 7 calluses of multiple diabetic mouse models. Models include: 10-week-old WT, 4-weekold pre-diabetic $Lepr_{db}$ (pre-$db_{LR}$), 4-week-old WT, $Lepr^{db}$ ($db_{LR}$), streptozotocin-induced diabetes (db/STZ), and diet-induced diabetes (db/DIO). Black arrows highlight differentially expressed genes. (FIG. 4D) Alizarin red staining shows that XL139 reduces the in vitro osteogenic potential of WT mSSCs from post-fracture day 7 calluses in a dose-dependent manner. (FIG. 4E) MST analysis of healing femora harvested at post-fracture week 4 from XL139-treated (grey) versus untreated (blue) WT mice. n=5. (FIG. 4F) Absolute cell numbers of mSSCs and BCSPs in XL139-treated (grey) versus untreated calluses (blue) isolated at post-fracture day 7 from WT mice. n=5. (FIG. 4G) Pre- and post-fracture serum levels of TNFα in $db_{LR}$ (red) versus WT mice (blue). n=3.

(FIG. 5A) Single-cell RNA-sequencing (ssRNA-seq) shows the cell-specific expression of TNFα receptor, Tumor necrosis factor receptor superfamily 1a (Tnfrsf1a), in mSSCs and BCSPs from postfracture day 7 calluses of $db_{LR}$ mice. (FIG. 5B) ssRNA-seq shows the cell-specific expression of Ihh in mSSCs and BCSPs isolated from postfracture day 7 calluses of $db_{LR}$ mice. (FIG. 5C) ssRNA-seq shows the cell-specific expression of hedgehog receptor, Ptch1, in mSSCs and BCSPs from post-fracture day 7 calluses of $db_{LR}$ mice. (FIG. 5D) ssRNA-seq shows the cell-specific expression of hedgehog effector, Gli1, in mSSCs and BCSPs from post-fracture day 7 calluses of $db_{LR}$ mice. (FIG. 5E) Schematic showing the experimental procedure used to investigate the effects of glucose or TNFα on Ihh expression in vitro. mSSCs and BCSPs were isolated from the appendicular skeleton of uninjured postnatal day 3 (P3) WT mice using FACS. Protein quantification was measured using realtime polymerase chain reaction (qRT-PCR). (FIG. 5F) qRT-PCR analysis reveals that TNFα significantly diminishes Ihh expression in mSSC-derived cultures isolated from uninjured P3 mice. (FIG. 5G) qRT-PCR analysis shows that glucose and TNFα reduces Ihh expression in BCSP-derived cultures isolated from uninjured P3 mice. (FIG. 5H) qRT-PCR analysis reveals that TNFα diminishes Ihh expression in BCSP-derived cultures isolated from uninjured P3 mice in a dose-dependent manner. (FIG. 5I) Schematic illustrating stem and progenitor cell crosstalk in the skeletal niche. BCSPs mediate mSSC activity through autocrine or paracrine signaling. Ihh expressed by BCSPs is recognized by Ptch1 on mSSCs, leading to signal transduction via Gli1. (FIG. 5J) Venn diagram showing that $db_{LR}$ mSSCs (left) and BCSPs (right) from post-fracture day 7 calluses co-express Ihh and Tnfrsf. Statistical analyses: unpaired two-tailed t-test. Results are depicted as mean±SEM; *p<0.05, p<0.01, *p<0.001, ****p<0.0001. "db" denotes $Lepr^{db}$ ($db_{LR}$) mice. qRT-PCR results are normalized with GAPDH.

(FIG. 6A) FACs gating strategy for isolation of human skeletal progenitor populations from collagenase-dissociated cells extracted from human femoral head and knee tissues. Both CD146(+) and CD146(−) skeletal stem progenitors are represented in non-hematopoietic CD45(−)CD235(−) populations. (FIG. 6B) Representative image of osteoarthritic femoral head. Arrows point to regions of skeletal lesions in which tissues were isolated for analysis. (FIG. 6C) Quantitative real-time PCR analysis of relative expression of IHH in CD45(−) CD235(−) CD146 (+/−) human bone progenitors isolated from non-diabetic vs. diabetic patients. Gene expression was normalized to beta-actin expression. n=5-6

(FIG. 6D) Quantitative real-time PCR analysis of relative expression of hedgehog responsive GLI1 in CD45(−) CD235(−) CD146 (+/−) human bone progenitors from non-diabetic vs. diabetic patients. Gene expression was normalized to beta-actin expression. n=5-6

(FIG. 7A) Experimental schematic showing placement of slow-release hydrogel treatment directly on the fracture site in WT or $db_{LR}$ mice. Then, mSSCs or BCSPs were isolated from post-fracture day 7 calluses for in vitro analysis, or healing femora were harvested after 4 weeks for MST. (FIG. 7B) MST analysis of untreated WT femora versus Ihh- (red), Shh- (green), or PBS-treated (black) femora harvested from $db_{LR}$ mice. In $db_{LR}$ mice, treatment with Ihh or Shh significantly increased femur strength relative to PBS-treated controls. All healing femora were harvested at post-fracture week 4. n=5. (FIG. 7C) Absolute cell numbers of mSSCs (top) and BCSPs (bottom) from untreated, WT femora versus Ihh-, Shh-, or PBS-treated calluses from $db_{LR}$ mice. Calluses were harvested at post-fracture day 7. (FIG. 7D) The colony-forming ability of mSSCs from Ihh-, Shh-, or PBS-treated calluses was measured by total number of colonies formed. mSSCs were isolated from $db_{LR}$ mice at post-fracture day 7. n=3. (FIG. 7E) Respective population percentages of BrdU-labeled mSSCs (left) or BCSPs (right) from Ihh-, Shh-, or PBS-treated calluses harvested at post-fracture day 3. n=4. (FIG. 7F) Respective population percentages of annexin V expression in mSSCs isolated from PBS- (left column) versus Ihh-treated (middle column) calluses $db_{LR}$ (bottom row) or WT mice (top row). Calluses were harvested at post-fracture day 7. Merged plots are shown (right column). (FIG. 7G) Alizarin red staining shows the osteogenic potential of mSSCs (top row) and BCSPs (bottom row) from Shh- (far left column), Ihh- (second column from left), or PBS-treated (second column from right) calluses versus untreated WT femora (far right column). Treated cell samples were isolated from $db_{LR}$ mice at post-fracture day 7. All cells were maintained in osteogenic differentiation media for six days. Brightfield microscopy, 10×; scale bar, 200 µm. Statistical analyses: unpaired two-tailed t-test. Results are depicted as mean±SEM; *p<0.05, **p<0.01.

(FIG. 9A) Schematic showing MST apparatus set-up. Femora were placed in a 3-point bend configuration between one pin on side "A" and two pins on side "B." The applied load was generated by compression between pins "A" and "B" and was analyzed by a computer program. The maximal load required to fracture the femur (Newton, N) per displacement (µm) from the original position was recorded. (FIG. 9B) Graphical representation of maximal load versus displacement, as recorded by MST. The maximal load to fracture (red arrow) is shown. All samples were preloaded to 1 N (black arrow).

(FIG. 10A) MST analysis of femora harvested from 4-week-old $Lepr^{-/-}$ (pre-diabetic, pre-$db_{LR}$) versus WT mice at post-fracture week 4 (n=5). (FIG. 10B) MST analysis of femora harvested from $db_{DIO}$ and $db_{STZ}$ versus WT mice at post-fracture week 4 (n=5). (FIG. 10C) Baseline absolute cell numbers of mSSCs or BCSPs in uninjured $db_{LR}$ versus WT femora (n=5). (FIG. 10D) Absolute cell numbers of mSSCs or BCSPs in post-fracture day 7 calluses of WT versus pre-diabetic, $Lepr_{db}$ mice (n=5). (FIG. 10E) Absolute cell numbers of mSSCs or BCSPs in post-fracture day 7 calluses of $db_{DIO}$ versus WT mice. (FIG. 10F) Absolute cell numbers of mSSCs or BCSPs in post-fracture day 7 calluses of $db_{STZ}$ versus WT mice. Data and error bars represent means±SEM. *p<0.05, p<0.01, **p<0.0001, unpaired two-tailed t-test.

(FIG. 11A) (Left) Line graph showing circulating blood glucose levels in WT versus $db_{LR}$ mice following fracture. As expected, $db_{LR}$ mice have significantly increased blood glucose levels. (Right) Line graph showing the weight (gram, g) of WT versus $db_{LR}$ mice after fracture. (FIG. 11B) Serum blood glucose levels (left) and weight (right) of $db_{STZ}$ versus WT mice. (FIG. 11C) Serum blood glucose levels (left) and weight (right) of $db_{DIO}$ versus WT mice. (FIG. 11D) Serum blood glucose levels (left) and weight (right) of pre-$db_{LR}$ versus age- and sex-matched WT mice. Although pre-$db_{LR}$ mice do not have glycemic levels consistent with fulminant DM at postnatal week 4, they are significantly heavier than age and sex-matched WT controls. Data and error bars represent means±SEM. *p<0.001, **p<0.0001, n=5 per group, unpaired two-tailed t-test.

(FIG. 13A) Femora were harvested at post-fracture week 4 and prepared for histological stain with Movat's Pentachrome for the following groups (left to right): WT PBS hydrogel, $db_{LR}$ PBS hydrogel, $db_{LR}$ Ihh hydrogel, and $db_{LR}$ Shh hydrogel. The outlined areas are magnified below. (Scale bar from left to right: top=2 mm; bottom=200 µm). (FIG. 13B) Bar graphs showing the perimeter of trabecular bone thickness after healing with the local hydrogel delivery of PBS, Ihh, or Shh. Data and error bars represent means±SEM. p<0.01, **p<0.0001, n=5, unpaired two-tailed t-test.

(FIG. 14A) Histological sections of fractured femora stained with Movat's Pentachrome on (left to right) post-fracture days 10, 14, and 21 demonstrate delayed development of cartilage (blue stain) in $db_{LR}$ versus WT mice following injury. The outlined areas are magnified (scale bar from top to bottom=2 mm, 200 µm, 200 µm, 2 mm). (FIG. 14B) Bar graphs showing the size of trabecular bone in healing femora at post-fracture day 21 (n=3). (FIG. 14C) Bar graph showing that db calluses are significantly smaller than WT controls. The variation in callus size within each group is small. (FIG. 14D) Brightfield micrographs of WT (top) and $db_{LR}$ (bottom) femora stained with Tartrate-Resistant Acid Phosphatase (TRAP) at (left to right) post-fracture days 14, 21, and 28 (scale bar from top to bottom of panel=2 mm, 200 µm, 200 µm, 2 mm). (FIG. 14E) Bar graphs showing no significant difference between groups in TRAP Staining intensity per 30,000 pixels area (n=3). Data and error bars represent means±SEM. **p<0.01, unpaired two-tailed t-test.

(FIG. 15A) Relative gene expression of mouse Ihh and Gli1 in mSSCs harvested from postnatal day 3 (P3) mice in medium supplemented with 5 pg/mL and 10 ng/mL of TNFα. (FIG. 15B) Relative gene expression of human Ihh in human bone progenitors treated with 10 ng/mL of TNFα. (FIG. 15C) Relative gene expression of mouse Ihh in P3 mSSC treated with 10 ng/mL TNFα and 2 ug/mL anti-TNFα antibody. (FIG. 15D) Relative gene expression of mouse Ihh in co-cultures of P3 mSSC with WT or db mouse serum containing 1 ug/mL anti-TNFα antibody. Data and error bars represent means±SEM. *p<0.05, unpaired two-tailed t-test.

DESCRIPTION OF THE SPECIFIC EMBODIMENTS

Figure 1A:
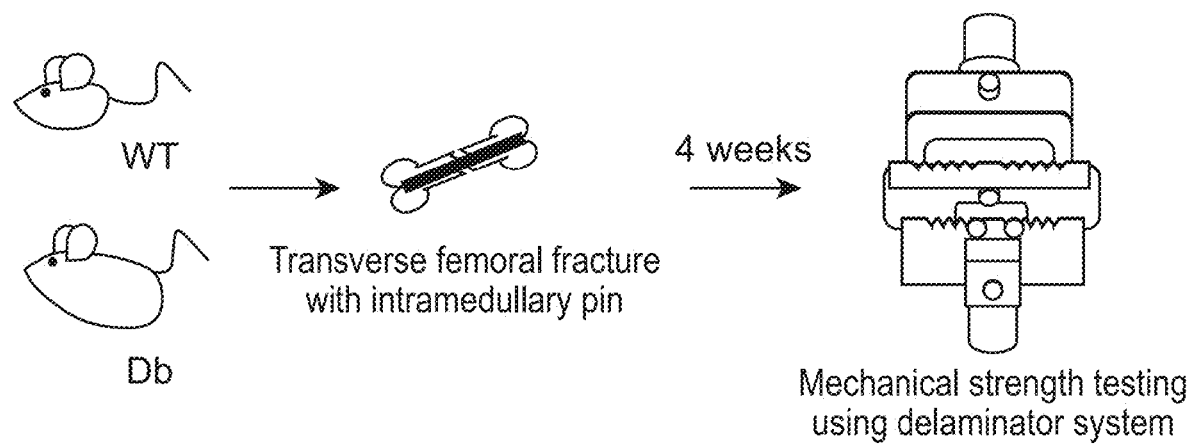
FIG. 1A-1I. mSSC-dependent bone healing is impaired in diabetic mice.

The methods of the invention utilize therapeutic hedgehog agent formulations for targeted delivery of the agent to a deficient skeletal stem cell niche. In some embodiments of the invention, a pharmaceutical composition for in vivo administration is provided, comprising a therapeutically effective dose of a hedgehog agent in a formulation, e.g. for sustained release, local delivery, etc. Pharmaceutical compositions of the present invention can be administered to a mammal, e.g. a human, for therapeutic purposes. In some embodiments of the invention, the compositions are administered locally, e.g. by implantation or injection at the site of a bone injury or implant.

For use in the above methods, the invention also provides an article of manufacture, comprising: a container, a label on the container, and a composition comprising an active agent within the container, wherein the composition comprises substantially homogeneous biologically active Indian hedgehog protein inserted in the non-aqueous phase of a lipid structure, which is effective in vivo, for example in enhancing proliferation and/or maintenance of stem or progenitor cells, and the label on the container indicates that the composition can be used for enhancing proliferation and/or maintenance of those cells.

Definitions

Before the present methods are described, it is to be understood that this invention is not limited to particular methods described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges encompassed within the invention, subject to any specifically excluded limit in the stated range.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a microsphere" includes a plurality of such microspheres and reference to "the stent" includes reference to one or more stents and equivalents thereof known to those skilled in the art, and so forth.

Hedgehog agent. As used herein, the term "hedgehog agent" or "agent that provides for hedgehog activity" refers to any agent that provides for the same activity in the signaling pathway as a native hedgehog protein on its homologous, cognate receptor, for example an agent may have at least about 20% of the native protein activity, at least about 30%, at least about 40%, at least about 50%, at least about 60%, at least about 70%, at least about 80%, at least about 90%, at least about 100%, or may have greater activity than the native protein, e.g. 2-fold, 3-fold, 5-fold, 10-fold or more activity. Levels of activity may be determined, for example, by assessing transcription of Ci target genes, processing of Ci, etc. Hedgehog (Hh) proteins are secreted morphogens that are essential for multiple developmental processes in both invertebrates and vertebrates. Secreted active Hh fragments can regulate cellular activities of neighboring and distant cells.

Hh-target cells express two components of the Hh signaling system on the cell surface: Patched (Ptc), a 12-transmembrane protein, and Smoothened (Smo), a 7-transmembrane protein. In the absence of Hh, Ptc represses the activity of Smo, which allows proteolytic processing of a downstream zinc-finger transcription factor, Cubitus intereptus (Ci) at its C-terminal end forming a transcriptional repressor. When Hh binds to Ptc it relieves Ptc repression of Smo and activated Smo stabilizes intact Ci, which then acts as a transcription activator, and hence stimulates transcription of target genes. In mammals there are two Ptc homologues, where both bind Hh proteins with similar affinity and both can interact with mammalian Smo. Ptc1 is widely expressed throughout the mouse embryo and serves as the extracellular receptor for multiple Hh proteins, and is itself upregulated by Hh signaling. Ptc2 is expressed at high levels in the skin and spermatocytes.

There are three vertebrate Hh proteins: Desert hedgehog (Dhh), Sonic hedgehog (Shh), and Indian hedgehog (Ihh). All of them have unique sets of functions in regulation of different developmental processes. Dhh is essential for the development of peripheral nerves and spermatogenesis. Shh is involved in establishing lateral asymmetry, the anterior-posterior limb axis, and development of the central nervous system. Ihh is a master regulator of endochondral bone development.

The hedgehog protein is initially synthesized as a 46 kDa precursor, with two distinct domains: the N-terminal "hedge" domain is processed to a 19 kDa fragment (Hh-N) following proteolytic cleavage that is executed by the C-terminal "hog" domain within the endoplasmic reticulum. The C-terminus acts as a cholesterol transferase to covalently attach a cholesterol group to the carboxy end of the Hh amino terminal fragment, Hh-N. The nascent Hh-N is further modified by the subsequent addition of a palmitoyl group at Cys-24, resulting in an extremely hydrophobic molecule that is referred to as Hh-Np for Hh-N-processed. The processing of Hh-N takes place in the secretory pathway and is mediated by a palmitoylacyltransferase which is coded for by the Skinny hedgehog gene (Ski/Skn). The palmitoyl addition is essential for SHH function. The addition of cholesterol and palmitate increases the efficacy of SHH-Np, while addition of hydrophilic adducts to the N terminus reduces the activity of SHH.

Protein sequences of exemplary hedgehog proteins, e.g. human hedgehog proteins, are publicly available at Genbank. Included are sonic hedgehog protein isoform 1, accession NP_000184.1; sonic hedgehog protein isoform 2, accession NP_001297391.1; indian hedgehog protein, accession number NP_002172; and desert hedgehog protein, accession NP_066382, the sequences thus identified are each specifically incorporated by reference.

Antibodies that specifically bind to human patched or smoothened are known in the art or can be generated by conventional methods. Such antibodies may be screened for agonist activity for use in the methods of the invention. Alternatively, small molecule agonists are known in the art, see, for example Frank-Kamenetsky et al. (2002) J. Biol. 1(2):10, herein specifically incorporated by reference. Specific agonists of interest include, without limitation N-Methyl-N'-(3-pyridinylbenzyl)-N'-(3-chlorobenzo[b]thiophene-2-carbonyl)-1,4-diaminocyclohexane, SAG1.1, SAG1.3, purmorphamine, etc., as described in Das et al. (2013) Sci Transl Med. 5(201):201ra120; Carney and Ingham BMC Biology 201311:37, etc.

The terms "hedgehog protein" or "hedgehog gene product" or "hedgehog polypeptide" when used herein encompass native sequence hedgehog polypeptides, hedgehog polypeptide variant, hedgehog polypeptide fragments and chimeric hedgehog polypeptides, e.g. for human hedgehog sequences including sonic hedgehog, indian hedgehog and desert hedgehog.

A "native sequence" polypeptide is one that has the same amino acid sequence as a hedgehog polypeptide derived from nature. Such native sequence polypeptides can be isolated from cells producing endogenous hedgehog protein or can be produced by recombinant or synthetic means. Thus, a native sequence polypeptide can have the amino acid sequence of, e.g. naturally occurring human polypeptide, murine polypeptide, or polypeptide from any other mammalian species, or from non-mammalian species, e.g. *Drosophila, C. elegans*, and the like.

A "variant" polypeptide means a biologically active polypeptide as defined below having less than 100% sequence identity with a native sequence polypeptide. Such variants include polypeptides wherein one or more amino acid residues are added at the N- or C-terminus of, or within, the native sequence; from about one to forty amino acid residues are deleted, and optionally substituted by one or more amino acid residues; and derivatives of the above polypeptides, wherein an amino acid residue has been covalently modified so that the resulting product has a non-naturally occurring amino acid. Frequently a biologically active hedgehog variant will have an amino acid sequence having at least about 90% amino acid sequence identity with a native sequence hedgehog polypeptide, preferably at least about 95%, more preferably at least about 99%.

A "chimeric" hedgehog polypeptide is a polypeptide comprising a hedgehog polypeptide or portion (e.g., one or more domains) thereof fused or bonded to heterologous polypeptide. The chimeric hedgehog polypeptide will generally share at least one biological property in common with a native sequence hedgehog polypeptide. Examples of chimeric polypeptides include immunoadhesins, combine a portion of the hedgehog polypeptide with an immunoglobulin sequence, and epitope tagged polypeptides, which comprise a hedgehog polypeptide or portion thereof fused to a "tag polypeptide". The tag polypeptide has enough residues to provide an epitope against which an antibody can be made, yet is short enough such that it does not interfere with biological activity of the hedgehog polypeptide. Suitable tag polypeptides generally have at least six amino acid residues and usually between about 6-60 amino acid residues.

A "functional derivative" of a native sequence hedgehog polypeptide is a compound having a qualitative biological property in common with a native sequence hedgehog polypeptide. "Functional derivatives" include, but are not limited to, fragments of a native sequence and derivatives of a native sequence hedgehog polypeptide and its fragments, provided that they have a biological activity in common with a corresponding native sequence hedgehog polypeptide. The term "derivative" encompasses both amino acid sequence variants of hedgehog polypeptide and covalent modifications thereof.

A fragment of a hedgehog protein may be selected to achieve a specific purpose. Such deletions generally extend from residue 1 through 10 of the peptide, and may further delete additionally amino acids at residues 11, 12 or more. Smaller deletions, of from 1 to to 5 amino acids, may be deleted in the N-terminus and still retain the properties.

The sequence of the hedgehog polypeptide may be altered in various ways known in the art to generate targeted changes in sequence. The polypeptide will usually be substantially similar to the sequences provided herein, i.e. will differ by at least one amino acid, and may differ by at least two but not more than about ten amino acids. The sequence changes may be substitutions, insertions or deletions. Scanning mutations that systematically introduce alanine, or other residues, may be used to determine key amino acids. Conservative amino acid substitutions typically include substitutions within the following groups: (glycine, alanine); (valine, isoleucine, leucine); (aspartic acid, glutamic acid); (asparagine, glutamine); (serine, threonine); (lysine, arginine); or (phenylalanine, tyrosine).

Modifications of interest that do not alter primary sequence include chemical derivatization of polypeptides, e.g., acetylation, or carboxylation. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine.

Also included in the subject invention are polypeptides that have been modified using ordinary molecular biological techniques and synthetic chemistry so as to improve their resistance to proteolytic degradation or to optimize solubility properties or to render them more suitable as a therapeutic agent. For examples, the backbone of the peptide may be cyclized to enhance stability (see Friedler et al. (2000) J. Biol. Chem. 275:23783-23789). Analogs of such polypeptides include those containing residues other than naturally occurring L-amino acids, e.g. D-amino acids or non-naturally occurring synthetic amino acids.

The subject peptides may be prepared by in vitro synthesis, using conventional methods as known in the art. Various commercial synthetic apparatuses are available, for example, automated synthesizers by Applied Biosystems, Inc., Foster City, Calif., Beckman, etc. By using synthesizers, naturally occurring amino acids may be substituted with unnatural amino acids. The particular sequence and the manner of preparation will be determined by convenience, economics, purity required, and the like.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

The polypeptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

Drug screening may be performed using an in vitro model, a genetically altered cell or animal, or purified hedgehog protein to identify ligands, mimetics and other agents that enhance or mimic the action of hedgehog. A wide variety of assays may be used for this purpose, including labeled in vitro protein-protein binding assays, electrophoretic mobility shift assays, immunoassays for protein binding, and the like. Knowledge of the 3-dimensional structure of hedgehog, derived from crystallization of purified synthetic hedgehog protein, leads to the rational design of small drugs that specifically inhibit hedgehog activity.

The term "agent" as used herein describes any molecule, e.g. protein or pharmaceutical, with the capability of altering or mimicking the physiological function of hedgehog. Generally, a plurality of assay mixtures are run in parallel with different agent concentrations to obtain a differential response to the various concentrations. Typically one of these concentrations serves as a negative control, i.e., at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin, etc. For the specific binding members, the complementary member would normally be labeled with a molecule that provides for detection, in accordance with known procedures.

Antibodies. The methods of the invention may utilize antibodies specific for a hedgehog receptor or member of the hedgehog signaling pathway as a hedgehog agent, which antibody can mimic the activity of a native hedgehog. As used herein, the term "antibodies" includes antibodies of any isotype, fragments of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein. The antibodies may be detectably labeled, e.g., with a radioisotope, an enzyme that generates a detectable product, a green fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like.

"Antibody specificity", in the context of antibody-antigen interactions, is a term well understood in the art, and indicates that a given antibody binds to a given antigen, wherein the binding can be inhibited by that antigen or an epitope thereof which is recognized by the antibody, and does not substantially bind to unrelated antigens. Methods of determining specific antibody binding are well known to those skilled in the art, and can be used to determine the specificity of antibodies of the invention for a hedgehog polypeptide, particularly a human hedgehog polypeptide.

Antibodies are prepared in accordance with conventional ways, where the expressed polypeptide or protein is used as an immunogen, by itself or conjugated to known immunogenic carriers, e.g. KLH, pre-S HBsAg, other viral or eukaryotic proteins, or the like. Various adjuvants may be employed, with a series of injections, as appropriate. For monoclonal antibodies, after one or more booster injections, the spleen is isolated, the lymphocytes immortalized by cell fusion, and then screened for high affinity antibody binding. The immortalized cells, i.e. hybridomas, producing the desired antibodies may then be expanded. For further description, see Monoclonal Antibodies: A Laboratory Manual, Harlow and Lane eds., Cold Spring Harbor Laboratories, Cold Spring Harbor, N.Y., 1988. If desired, the mRNA encoding the heavy and light chains may be isolated and mutagenized by cloning in E. coli, and the heavy and light chains mixed to further enhance the affinity of the antibody. Alternatives to in vivo immunization as a method of raising antibodies include binding to phage display libraries, usually in conjunction with in vitro affinity maturation.

Diabetes. Individuals selected for treatment by the methods of the invention generally have been diagnosed or are diagnosed as part of the treatment with diabetes or metabolic syndrome. Diabetes mellitus is a group of metabolic diseases characterized by hyperglycemia resulting from defects in insulin secretion, insulin action, or both. The chronic hyperglycemia of diabetes is associated with long-term damage, dysfunction, and failure of various organs, especially the eyes, kidneys, nerves, heart, and blood vessels.

The vast majority of cases of diabetes fall into two broad etiopathogenetic categories. In one category, type 1 diabetes, the cause is an absolute deficiency of insulin secretion. Individuals at increased risk of developing this type of diabetes can often be identified by serological evidence of an autoimmune pathologic process occurring in the pancreatic islets and by genetic markers. In the other, much more prevalent category, type 2 diabetes, the cause is a combination of resistance to insulin action and an inadequate compensatory insulin secretory response. In the latter category, a degree of hyperglycemia sufficient to cause pathologic and functional changes in various target tissues, but without clinical symptoms, may be present for a long period of time before diabetes is detected. During this asymptomatic period, it is possible to demonstrate an abnormality in carbohydrate metabolism by measurement of plasma glucose in the fasting state or after a challenge with an oral glucose load.

The degree of hyperglycemia (if any) may change over time, depending on the extent of the underlying disease process. A disease process may be present but may not have progressed far enough to cause hyperglycemia. The same disease process can cause impaired fasting glucose (IFG) and/or impaired glucose tolerance (IGT) without fulfilling the criteria for the diagnosis of diabetes. In some individuals with diabetes, adequate glycemic control can be achieved with weight reduction, exercise, and/or oral glucose-lowering agents. These individuals therefore do not require insulin. Other individuals who have some residual insulin secretion but require exogenous insulin for adequate glycemic control can survive without it. Individuals with extensive β-cell destruction and therefore no residual insulin secretion require insulin for survival. The severity of the metabolic abnormality can progress, regress, or stay the same. Thus, the degree of hyperglycemia reflects the severity of the underlying metabolic process and its treatment more than the nature of the process itself.

Type 2 diabetes, which accounts for ~90-95% of those with diabetes, previously referred to as non-insulin-dependent diabetes, type II diabetes, or adult-onset diabetes, encompasses individuals who have insulin resistance and usually have relative (rather than absolute) insulin deficiency. Most patients with this form of diabetes are obese, and obesity itself causes some degree of insulin resistance. Patients who are not obese by traditional weight criteria may have an increased percentage of body fat distributed predominantly in the abdominal region. Ketoacidosis seldom occurs spontaneously in this type of diabetes; when seen, it usually arises in association with the stress of another illness such as infection. This form of diabetes frequently goes undiagnosed for many years because the hyperglycemia develops gradually and at earlier stages is often not severe enough for the patient to notice any of the classic symptoms of diabetes. Nevertheless, such patients are at increased risk of developing macrovascular and microvascular complications. Whereas patients with this form of diabetes may have insulin levels that appear normal or elevated, the higher blood glucose levels in these diabetic patients would be expected to result in even higher insulin values had their β-cell function been normal. Thus, insulin secretion is defective in these patients and insufficient to compensate for insulin resistance. Insulin resistance may improve with weight reduction and/or pharmacological treatment of hyperglycemia but is seldom restored to normal. The risk of developing this form of diabetes increases with age, obesity, and lack of physical activity.

Categories of fasting plasma glucose (FPG) values are as follows: FPG<100 mg/dl (5.6 mmol/l)=normal fasting glucose; FPG 100-125 mg/dl (5.6-6.9 mmol/l)=IFG (impaired fasting glucose); FPG≥126 mg/dl (7.0 mmol/l)=provisional diagnosis of diabetes. The corresponding categories when the oral glucose tolerance test (OGTT) is used are the following: 2-h postload glucose<140 mg/dl (7.8 mmol/l)= normal glucose tolerance; 2-h postload glucose 140-199 mg/dl (7.8-11.1 mmol/l)=IGT (impaired glucose tolerance); 2-h postload glucose≥200 mg/dl (11.1 mmol/l)=provisional diagnosis of diabetes. IFG and IGT are associated with the metabolic syndrome, which includes obesity (especially abdominal or visceral obesity), dyslipidemia of the high-triglyceride and/or low-HDL type, and hypertension.

Methods of Use

In clinical situations for individuals suffering from diabetes mellitus, bone healing condition are impaired. In methods of accelerating bone repair, a pharmaceutical composition of the present invention comprising an effective dose of a hedgehog agent is administered to a patient suffering from damage to a bone, e.g. following an injury. The formulation is preferably administered at or near the site of injury, following damage requiring bone regeneration. The formulation may be administered for a short period of time, and in a dose that is effective to increase the number of bone progenitor cells present at the site of injury. In some embodiments the formulation is administered within about two days, usually within about 1 day of injury, and is provided for not more than about two weeks, not more than about one week, not more than about 5 days, not more than about 3 days, etc.

In some embodiments, the effective dose is the amount necessary to accelerate bone healing, e.g. to accelerate time to healing by about at least about 25%, at least about 50%, at least about 75%, at least about 100%, at least about 125%, at least about 150% or more, relative to healing in the absence of the agent. In some embodiments the effective dose is the amount necessary to increase the presence of skeletal stem cells (SSC) by at least about 25%, at least about 50%, at least about 75%, at least about 100%, at least about 125%, at least about 150% or more, relative to healing in the absence of the agent. In some embodiments, the effective dose is the dose that provides activity comparable to a native hedgehog protein at a concentration of least about 0.1 µg/kg, least about 1 µg/kg, least about 10 µg/kg, least about 100 µg/kg, at least about 1 mg/kg, at least about 10 mg/kg, at least about 100 mg/kg, at least about 500 mg/kg, and dosage ranges therein.

In methods of accelerating bone repair, a pharmaceutical hedgehog composition is administered to a patient suffering from damage to a bone, e.g. following an injury, or desiring increased osteogenic activity, e.g. at the site of an implant. The formulation is preferably administered at or near the site of desired osteogenesis, following the incident requiring bone regeneration.

In some embodiments, a patient requiring bone regeneration is also treated with an effective dose of skeletal stem cells. The cells may be treated ex vivo with a pharmaceutical composition comprising a hedgehog protein or proteins in a dose sufficient to enhance regeneration; or the cell composition may be administered to a patient in conjunction with a hedgehog formulation of the invention. Optionally, the treatment method of the present invention is combined with one or more of bone autograft, bone allograft, autologous stem cell treatment, allogeneic stem cell treatment, chemical stimulation, electrical stimulation, internal fixation, and external fixation.

A hedgehog agent is locally administered to the patient by injection or implantation of a hedgehog agent or a hedgehog agent delivery system adapted for the localized administration of the agent. Therefore, the present invention also relates to a drug delivery device, which comprises a hedgehog agent and a pharmaceutically acceptable carrier.

Bone implants have been extensively employed to replace missing or damaged hard tissues. Implants are manufactured to withstand the movement and stress associated with these clinical applications but the lifespan of implants is limited: Because they are denser and stronger than bone, implants can eventually weaken the surrounding bone-material interface. When this connection between bone and the implant surface is lost then the implant must be removed and replaced. In cases where osseointegration is likely to be compromised because of a poor implant bed or underlying illness then the ability to stimulate rapid and robust osseointegration is essential. Osseointegration occurs when cells in the peri-implant space attach to the implant surface and differentiate into matrix-secreting osteoblasts. In some embodiments of the invention, methods are providing for providing an individual with a stable orthopedic or dental implant, where the method comprises introducing an orthopedic or dental implant into a diabetic or pre-diabetic individual in need thereof; and contacting the site of the implant with a hedgehog formulation comprising an effective dose of a hedgehog agent, where the site of implant includes, without limitation, the peri-implant space.

Therapeutic formulations of hedgehog agent in the hedgehog agent delivery systems employable in the methods of the present invention may be prepared for storage by mixing the hedgehog agent having the desired degree of purity with optional pharmaceutically acceptable carriers, excipients, stabilizers, or enhancers of hedgehog agent activity. Such therapeutic formulations can be in the form of lyophilized formulations or aqueous solutions. Acceptable biocompatible carriers, excipients, or stabilizers are nontoxic to recipients at the dosages and concentrations employed, and may include buffers, for example, phosphate, citrate, and other organic acids; antioxidants including ascorbic acid and methionine; preservatives (e.g. octadecyldimethylbenzyl ammonium chloride; hexamethonium chloride; benzalkonium chloride, benzethonium chloride; phenol, butyl or benzyl alcohol; alkyl parabens, for example, methyl or propyl paraben; catechol; resorcinol; cyclohexanol; 3-pentanol; and m-cresol); low molecular weight (less than about 10 residues) polypeptides; proteins, for example, serum albumin, gelatin, or immunoglobulins; hydrophilic polymers, for example, polyvinylpyrrolidone; amino acids, for example, glycine, glutamine, asparagine, histidine, arginine, or lysine; monosaccharides, disaccharides, and other carbohydrates including glucose, mannose, dextrins, or hyaluronan; chelating agents, for example, EDTA; sugars, for example, sucrose, mannitol, trehalose or sorbitol; salt-forming counter-ions, for example, sodium; metal complexes (e.g. Zn-protein complexes); and/or non-ionic surfactants, for example, TWEEN™, PLURONICS™ or polyethylene glycol (PEG).

In order for the formulations to be used in vivo administration, they must be sterile. The formulation may be readily rendered sterile by filtration through sterile filtration membranes, prior to or following lyophilization and reconstitution. The therapeutic formulations herein preferably are placed into a container having a sterile access port, for example, an intravenous solution bag or vial having a stopper pierceable by a hypodermic injection needle.

The formulations used herein may also contain more than one active compound as necessary for the particular indication being treated, preferably those with complementary activities that do not adversely affect each other. Such molecules are present in combinations and amounts that are effective for the intended purpose. Optionally, the hedgehog agent delivery system includes a bioactive bone agent in addition to hedgehog agent. Preferably, the bioactive bone agent is selected from peptide growth factors (e.g., IGF (1,2), PDGF (AA, AB, BB), BMPs, FGF (1-20), TGF-beta (1-3), aFGF, bFGF, EGF, VEGF, parathyroid hormone (PTH), and parathyroid hormone-related protein (PTHrP)), anti-inflammatory factors (e.g., anti-TNFα, soluble TNF receptors, IL1ra, soluble IL1 receptors, IL4, IL-10, and IL-13), pro-inflammatory factors, inhibitors of apoptosis, MMP inhibitors and bone catabolic antagonists (e.g., bisphosphonates, osteoprotegerin, and statins).

The route of administration of hedgehog agent via the hedgehog agent delivery system is in accordance with known methods, e.g., via immediate-release, controlled-release, sustained-release, or extended-release means. Preferred modes of administration for the hedgehog agent delivery system include injection directly into afflicted bone sites and areas adjacent and/or contiguous to these sites or surgical implantation of the hedgehog agent delivery system directly into afflicted bone sites and areas adjacent and/or contiguous to these sites. Alternatively, the hedgehog agent delivery system is an article for implantation or a coating on an article for implantation. Preferred forms for the hedgehog agent delivery system include powders, granules, and bone cements.

The hedgehog agent molecules may also be entrapped in microcapsules prepared, for example by coacervation techniques or by interfacial polymerization, for example, hydroxymethylcellulose or gelatin-microcapsules and poly-(methylmethacrylate) microcapsules, respectively. Such preparations can be administered in colloidal drug delivery systems (for example, liposomes, albumin microspheres, microemulsions, nano-particles and nanocapsules) or in macroemulsions. Such techniques are disclosed in Remington's Pharmaceutical Sciences, 16th Edition (or newer), Osol A. Ed. (1980).

Optionally, the hedgehog agent delivery vehicle includes porous or non-porous calcium phosphate, porous or non-porous calcium phosphate, porous or non-porous hydroxyapatite, porous or non-porous tricalcium phosphate, porous or non-porous tetracalcium phosphate, porous or non-porous calcium sulfate, calcium minerals obtained from natural bone, inorganic bone, organic bone, or a combination thereof.

Where sustained-release or extended-release administration of hedgehog agent polypeptides is desired, microencapsulation of the hedgehog protein may be provided, see for example Cleland, "Design and Production of Single Immunization Vaccines Using Polylactide Polyglycolide Microsphere Systems" in Vaccine Design: The Subunit and Adjuvant Approach, Powell and Newman, eds., (Plenum Press: New York, 1995), pp. 439-462; WO 97/03692, WO 96/40072, WO 96/07399 and U.S. Pat. No. 5,654,010.

Suitable examples of sustained-release preparations include semipermeable matrices of solid hydrophobic polymers comprising the hedgehog agent, which matrices are in the form of shaped articles, e.g. films, or microcapsules.

Examples of sustained-release matrices include one or more polyanhydrides (e.g., U.S. Pat. Nos. 4,891,225; 4,767,628), polyesters, for example, polyglycolides, polylactides and polylactide-co-glycolides (e.g., U.S. Pat. Nos. 3,773,919; 4,767,628; 4,530,840; Kulkami et al., Arch. Surg. 93: 839 (1966)), polyamino acids, for example, polylysine, polymers and copolymers of polyethylene oxide, polyethylene oxide acrylates, polyacrylates, ethylene-vinyl acetates, polyamides, polyurethanes, polyorthoesters, polyacetylnitriles, polyphosphazenes, and polyester hydrogels (for example, poly(2-hydroxyethyl-methacrylate), or poly(vinylalcohol)), cellulose, acyl substituted cellulose acetates, non-degradable polyurethanes, polystyrenes, polyvinyl chloride, polyvinyl fluoride, poly(vinylimidazole), chlorosulphonated polyolefins, polyethylene oxide, copolymers of L-glutamic acid and γ-ethyl-L-glutamate, non-degradable ethylene-vinyl acetate, degradable lactic acid-glycolic acid copolymers, for example, the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of hedgehog agent for over 100 days, certain hydrogels release proteins for shorter time periods. Additional non-biodegradable polymers which may be employed are polyethylene, polyvinyl pyrrolidone, ethylene vinylacetate, polyethylene glycol, cellulose acetate butyrate and cellulose acetate propionate.

Alternatively, sustained-release formulations may be composed of degradable biological materials, for example, bioerodible fatty acids or metal salts thereof (e.g., palimitic acid, steric acid, oleic acid, myristic acid, metal salts thereof, and the like). Biodegradable polymers are attractive drug formulations because of their biocompatibility, high responsibility for specific degradation, and ease of incorporating the active drug into the biological matrix. For example, hyaluronic acid (HA) may be crosslinked and used as a swellable polymeric delivery vehicle for biological materials. U.S. Pat. No. 4,957,744; Valle et al., Polym. Mater. Sci. Eng. 62: 731-735 (1991). HA polymer grafted with polyethylene glycol has also been prepared as an improved delivery matrix which reduced both undesired drug leakage and the denaturing associated with long term storage at physiological conditions. Kazuteru, M., J. Controlled Release 59:77-86 (1999). Additional biodegradable polymers which may be used are poly(caprolactone), polyanhydrides, polyamino acids, polyorthoesters, polycyanoacrylates, poly(phosphazines), poly(phosphodiesters), polyesteramides, polydioxanones, polyacetals, polyketals, polycarbonates, polyorthocarbonates, degradable and non-toxic polyurethanes, polyhydroxylbutyrates, polyhydroxyvalerates, polyalkylene oxalates, polyalkylene succinates, poly(malic acid), chitin, and chitosan.

Alternatively, biodegradable hydrogels may be used as controlled-release materials for the hedgehog agent delivery vehicles. Through the appropriate choice of macromers, membranes can be produced with a range of permeability, pore sizes and degradation rates suitable for different types of hedgehog agent.

Alternatively, sustained-release delivery systems for hedgehog agents can be composed of dispersions. Dispersions may further be classified as either suspensions or emulsions. In the context of delivery vehicles for hedgehog agent, suspensions are a mixture of very small solid particles which are dispersed (more or less uniformly) in a liquid medium. The solid particles of a suspension can range in size from a few nanometers to hundreds of microns, and include microspheres, microcapsules and nanospheres. Emulsions, on the other hand, are a mixture of two or more immiscible liquids held in suspension by small quantities of emulsifiers. Emulsifiers form an interfacial film between the immiscible liquids and are also known as surfactants or detergents. Emulsion formulations can be both oil in water (o/w) wherein water is in a continuous phase while the oil or fat is dispersed, as well as water in oil (w/o), wherein the oil is in a continuous phase while the water is dispersed. One example of a suitable sustained-release formulation is disclosed in WO 97/25563. Additionally, emulsions for use with hedgehog agent in the present invention include multiple emulsions, microemulsions, microdroplets and liposomes. Microdroplets are unilamellar phospholipid vesicles that consist of a spherical lipid layer with an oil phase inside. E.g., U.S. Pat. Nos. 4,622,219 and 4,725,442. Liposomes are phospholipid vesicles prepared by mixing water-insoluble polar lipids with an aqueous solution.

Alternatively, the sustained-release formulations of a hedgehog agent may be developed using poly-lactic-coglycolic acid (PLGA), a polymer exhibiting a strong degree of biocompatibility and a wide range of biodegradable properties. The degradation products of PLGA, lactic and glycolic acids, are cleared quickly from the human body. Moreover, the degradability of this polymer can be adjusted from months to years depending on its molecular weight and composition. For further information see Lewis, "Controlled Release of Bioactive Agents from Lactide/Glycolide polymer," in Biogradable Polymers as Drug Delivery Systems M. Chasin and R. Langeer, editors (Marcel Dekker: New York, 1990), pp. 1-41.

Encapsulated hedgehog agents in extended-release formulation may be imparted by formulating the hedgehog agent polypeptide with water-soluble polyvalent metal salts, which are non-toxic at the release concentration and temperature. Exemplary "polyvalent metals" include the following cations: $Ca^{2+}$, $Mg^{2+}$, $Zn^{2+}$, $Fe^{2+}$, $Fe^{3+}$, $Cu^{2+}$, $Sn^{2+}$, $Al^{2+}$ and $Al^{3+}$. Exemplary anions which form water-soluble salts with the above polyvalent metal cations include those formed by inorganic acids and/or organic acids. Such water-soluble salts have a solubility in water (at 20° C.) of at least about 20 mg/ml, alternatively 100 mg/ml, alternatively 200 mg/ml.

"Therapeutically-effective amount" means an amount effective to accelerate bone healing in a patient. Exemplary healing mechanisms include, but are not limited to: (a) retaining mineralized components in bone, (b) inhibiting release of mineralized components from bone, (c) stimulating osteoblast activity, (d) reducing osteoclast activity, or (e) stimulating bone remodeling. Dosages of hedgehog agent employable with the present invention may vary depending on the particular use envisioned. The determination of the appropriate dosage or route of administration is well within the skill of an ordinary physician.

In a formulation, the concentration of the hedgehog agent may be from about 0.1% to 99% of the total weight of the formulation, e.g. from about 1%, about 5%, about 10%, about 15%, about 20%, about 25%, about 30%, about 35%, about 40%, about 45, about 50%, up to about 95%, up to about 90%, up to about 85%, up to about 80%, up to about 75%, up to about 70%, up to about 65%, up to about 60%, up to about 55%, or ranges therein.

The subject methods are useful for both prophylactic and therapeutic purposes. Thus, as used herein, the term "treating" is used to refer to enhanced regeneration of bone, enhanced osseointegration of implants, prevention of implant failure, and treatment of a pre-existing condition. Evidence of therapeutic effect may be any diminution in the severity of disease. The therapeutic effect can be measured in terms of clinical outcome or can be determined by mechanical or biochemical tests. Patients for treatment may be mammals, e.g. primates, including humans, may be laboratory animals, e.g. rabbits, rats, mice, etc., particularly for evaluation of therapies, horses, dogs, cats, farm animals, etc.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. Due to biological functional equivalency considerations, changes can be made in protein structure without affecting the biological action in kind or amount. All such modifications are intended to be included within the scope of the appended claims.

EXPERIMENTAL

Pharmacological Rescue of Diabetic Skeletal Stem Cell Niches

Abstract: Diabetes mellitus (DM) is a metabolic disease frequently associated with impaired bone healing, but despite its increasing prevalence worldwide, the molecular etiology of DM linked skeletal complications remains poorly defined. Using advanced stem cell characterization techniques, we analyzed intrinsic and extrinsic determinants of skeletal stem cell (mSSC) function to identify specific mSSC niche-related abnormalities that could impair skeletal repair in diabetic (db) mice. We discovered that high serum levels of tumor necrosis factor-a directly repressed the expression of Indian hedgehog (Ihh) in mSSCs and their downstream skeletogenic progenitors in db mice. When hedgehog signaling is inhibited during fracture repair, injury-induced mSSC expansion is suppressed, resulting in impaired healing. We reversed this deficiency by precise delivery of purified Ihh to the fracture site via a specially formulated, slow-release hydrogel. In the presence of exogenously applied Ihh, the injury-induced expansion and osteogenic potential of mSSCs was restored, culminating in the rescue of diabetic bone healing. Our results present a feasible strategy for precise treatment of molecular aberrations in stem and progenitor cell populations to correct skeletal manifestations of systemic disease.

Diabetes mellitus (DM) is a chronic metabolic disease that is increasing in frequency at an unprecedented rate. It is associated with a myriad of clinical complications, one of the most debilitating being impaired bone healing. Although patients with DM have increased bone resorption and osteoclast activity, how specific bone stem and progenitor cells contribute to the molecular etiology of DM-related skeletal complications is not well understood. We set out to molecularly characterize the skeletal stem cell niche to elucidate the mechanism of impaired diabetic bone healing.

Our laboratory's recent identification of the mouse skeletal stem cell (mSSC), a single multipotent stem cell capable of producing all of the skeletal elements, enables us to determine the homeostatic and injury-induced phenotypes of the mSSC and its downstream lineage in diabetic (db) mice. We showed previously that the mSSC and its downstream progenitor—the bone, cartilage, and stromal progenitor (BCSP)—facilitate the rapid repair of skeletal tissue in non-diabetic mice. When these cell types are reduced in number, fracture healing is severely impaired. Thus, we propose that aberrant stem and progenitor cell activity could lead to impaired db bone healing.

Figure 1B:
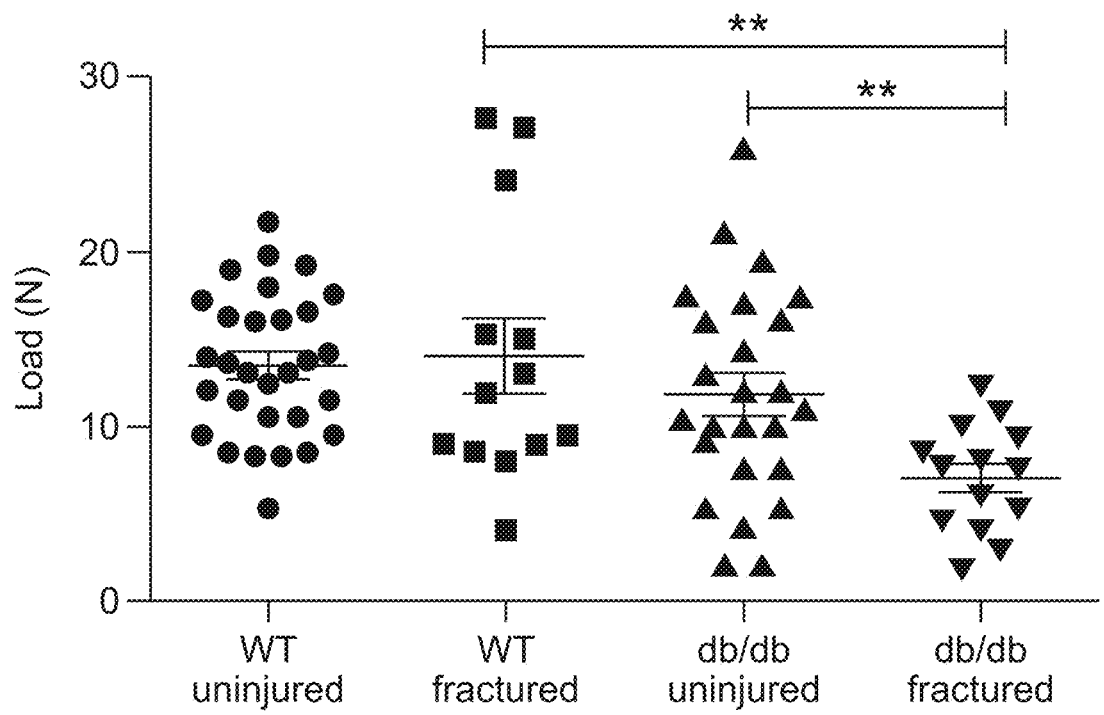
Figure 1C:
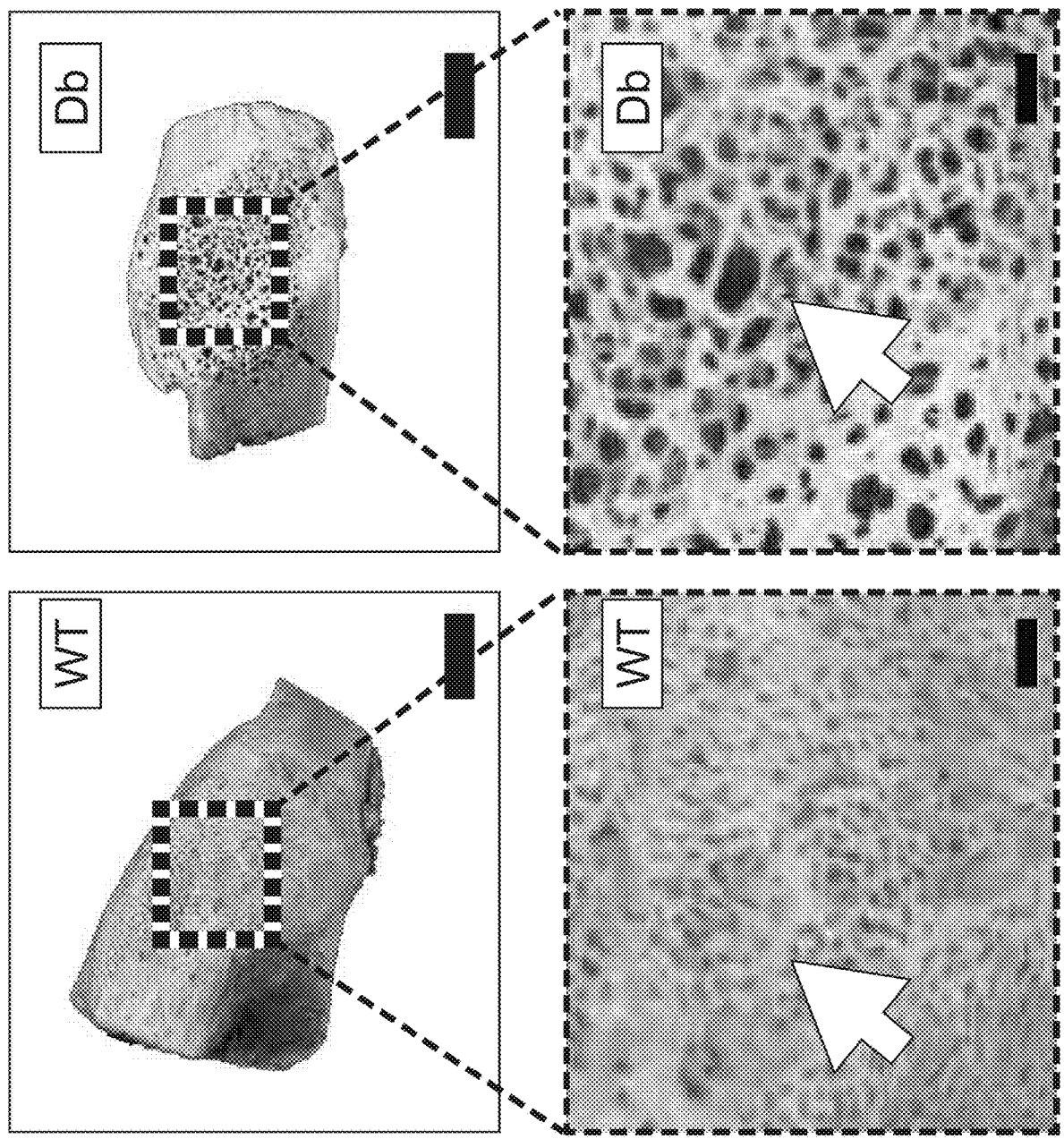
Figure 1C:
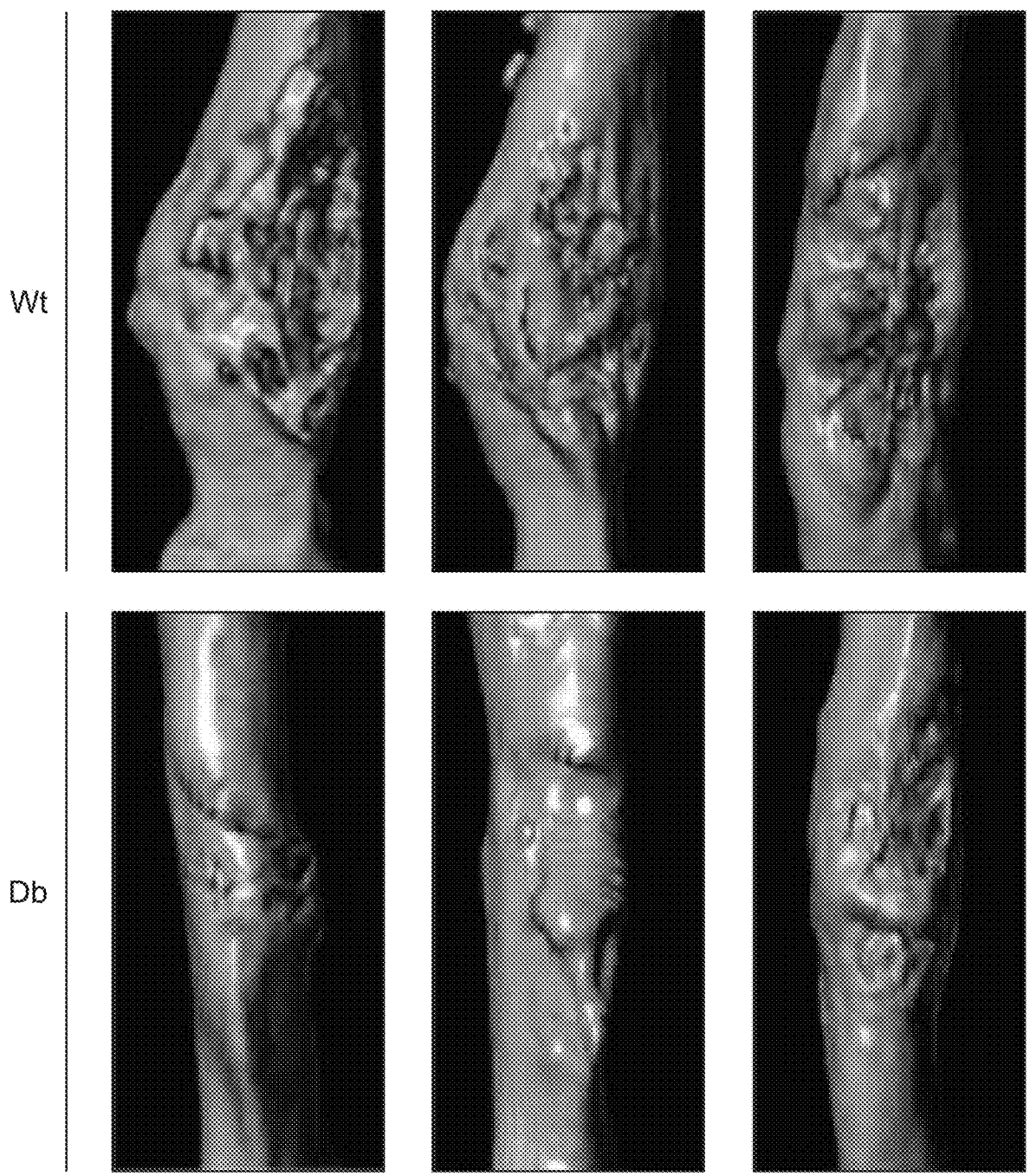
Figure 1C:
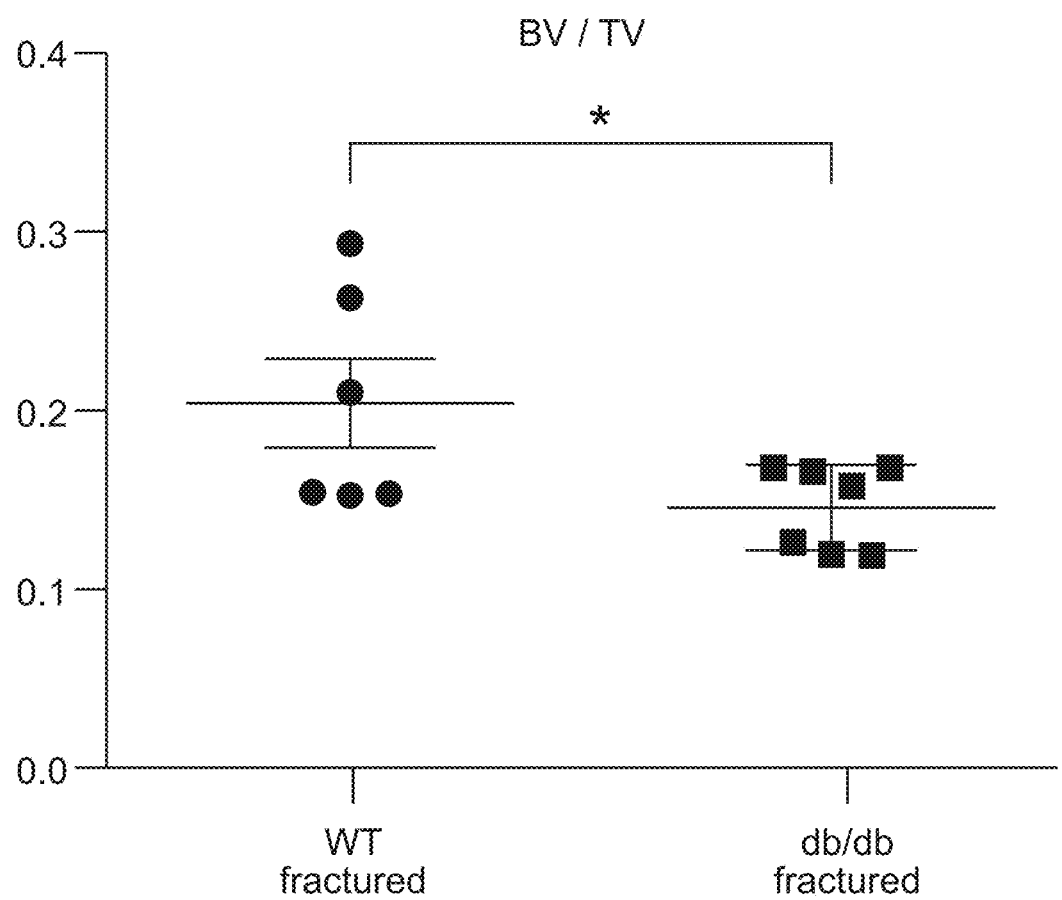
Figures 9A, 9B:
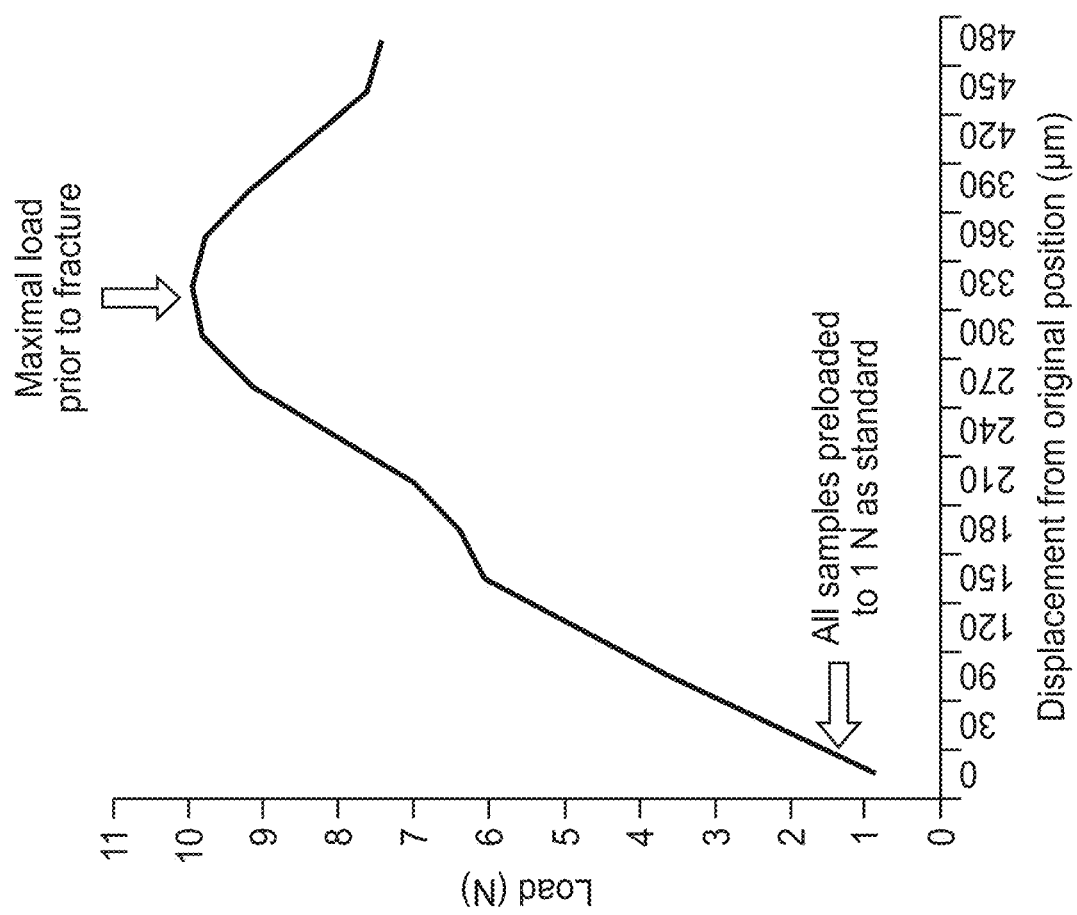
FIG. 9A-9B. Mechanical Strength Testing (MST) apparatus and assessment.

Results mSSC-dependent skeletal repair is impaired in diabetic mice. To determine whether DM is associated with impaired fracture healing in mice, we created transverse femoral fractures in 10-week-old diabetic (Lepr$^{db}$, denoted as db$_{LR}$) and nondiabetic (C57Bl/6, denoted as WT) female mice and fixed them with an intramedullary pin (FIG. 1A). The Lepr$^{db}$ mouse is a model of Type 2 DM resulting from an autosomal recessive mutation of the db gene, which codes for the leptin receptor. These mice are hyperphagic and secrete excessive insulin, making them obese, insulin resistant, hyperinsulinemic and hyperglycemic from four weeks of age. We assessed bone healing using a variety of techniques, including mechanical strength testing (MST), histology, and high-resolution microcomputed tomography (uCT). MST of healing femora was conducted at post-fracture week 4 (FIG. 9). This analysis revealed that healing db$_{LR}$ femora were significantly weaker than WT controls (FIG. 1B). In addition, analysis of post-fracture week 4 callus with ex vivo uCT showed that db$_{LR}$ femora had lower trabecular bone density than WT controls (FIG. 1C). Similarly, histomorphometric comparison of healing db$_{LR}$ and WT femora showed reduced osteogenesis in db$_{LR}$ mice; however, osteoclastic activity within the healing fractures was not significantly different between db$_{LR}$ and WT mice (FIG. 14).

Figure 10A:
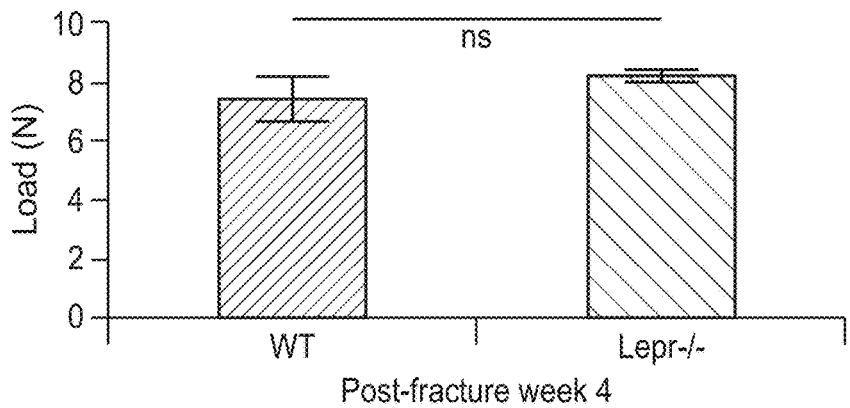
FIG. 10A-10F. Impaired mSSC- and BCSP-mediated bone healing is consistent in multiple mouse models of diabetes mellitus.
Figure 10B:
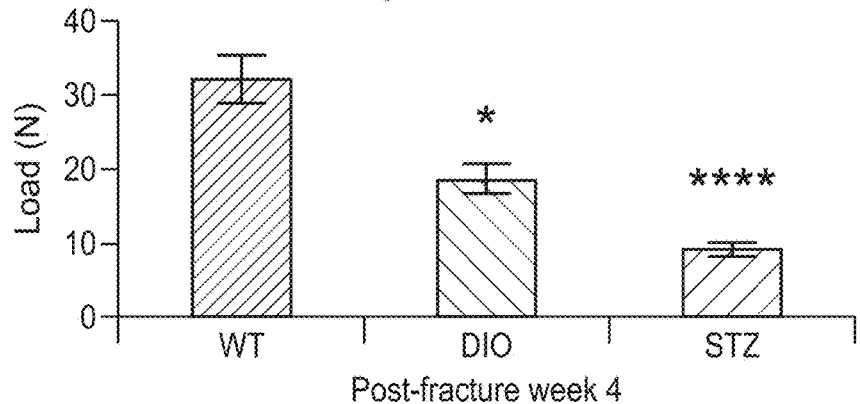

To further test whether impaired bone healing in db$_{LR}$ mice was associated with DM, we created femoral fractures in db$_{LR}$ mice at postnatal week 4, prior to the onset of DM (denoted as pre-db$_{LR}$). This experiment allowed us to determine the effect of DM and aberrant leptin signaling, as proposed by Karsenty et al., on injury-induced bone regeneration. MST analysis showed no significant difference in strength between healing femora from pre-db$_{LR}$ and age and sex-matched controls (FIG. 10A). These results indicate that impaired bone regeneration arose during active DM and was not related to aberrant leptin signaling. We also tested our hypothesis in streptozotocin-induced (db$_{STZ}$) and diet-induced obesity (db$_{DIO}$) mouse models of DM. In both models, the strength of healing femora was reduced significantly compared to WT controls (FIG. 10B). Collectively, these findings show that DM impairs bone healing in multiple models of diabetes in mice.

Figure 1D:
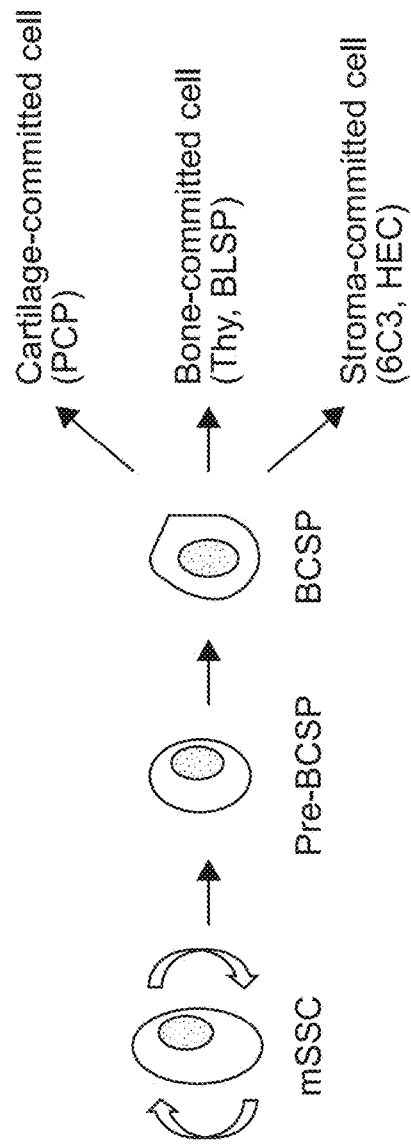
Figure 10C:
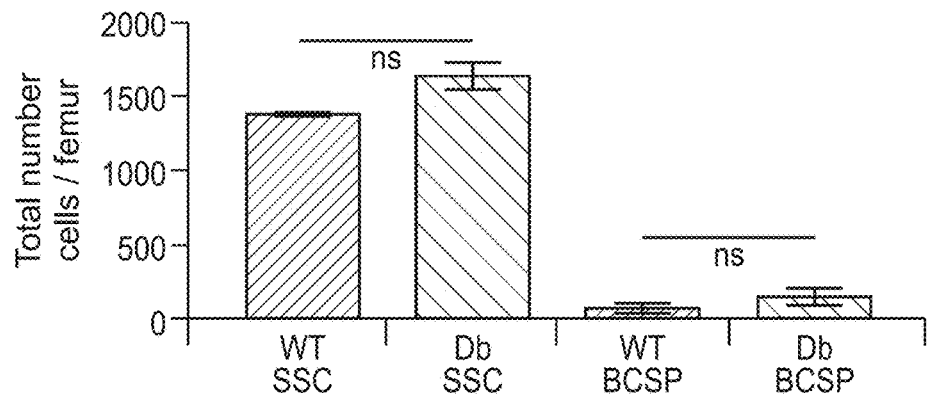

Considering our previous characterization of mSSC- and BCSP-dependent skeletal growth and repair (FIG. 1D), we hypothesized that a reduction in these cell populations could impair bone healing in $db_{LR}$ mice. When we analyzed mSSC and BCSP populations isolated from uninjured femora of $db_{LR}$ and WT mice using fluorescence-activated cell sorting (FACS), there was no significant difference in absolute cell numbers of either population (FIG. 10C).

Figure 1E:
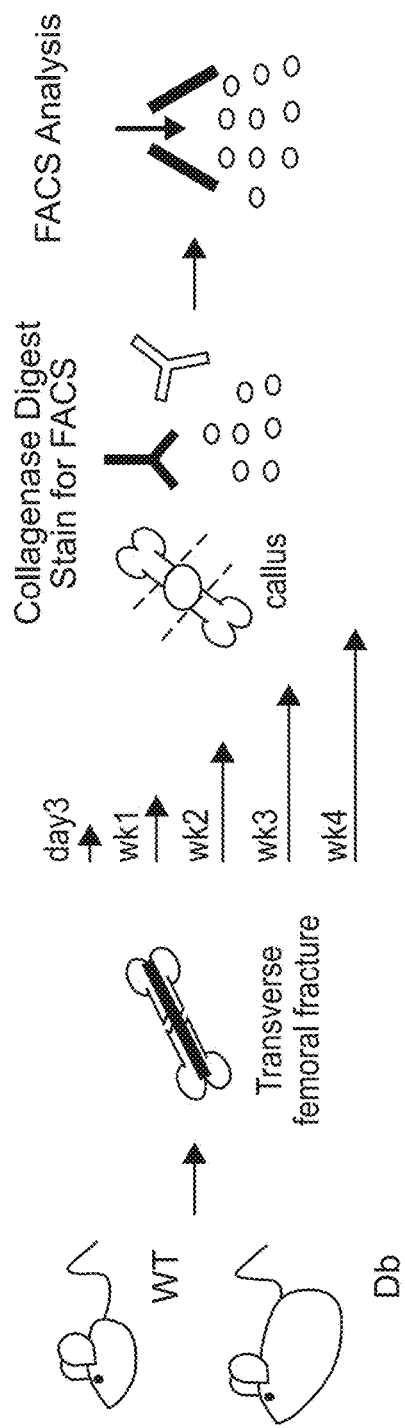
Figure 1F:
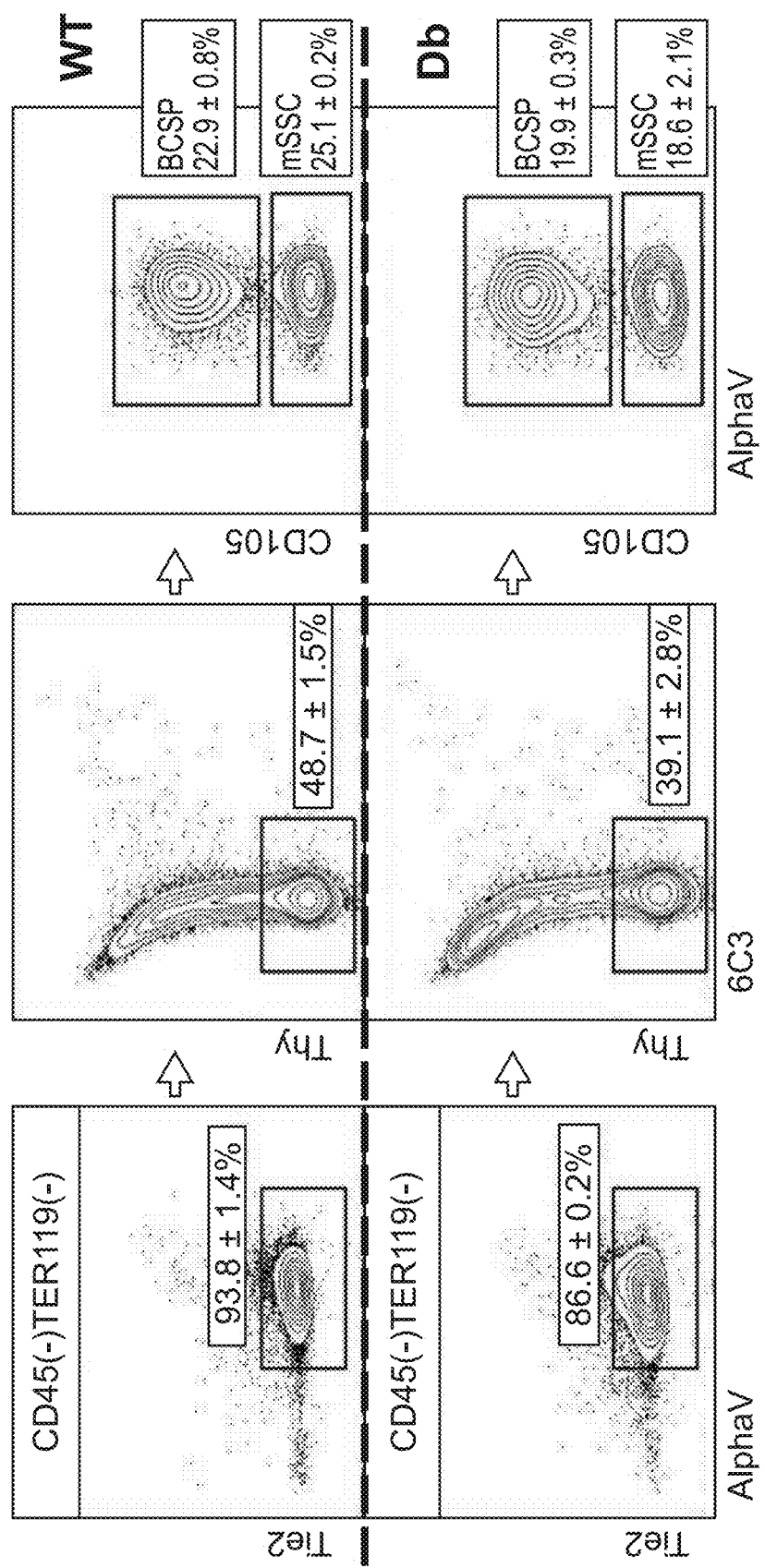
Figure 1G:
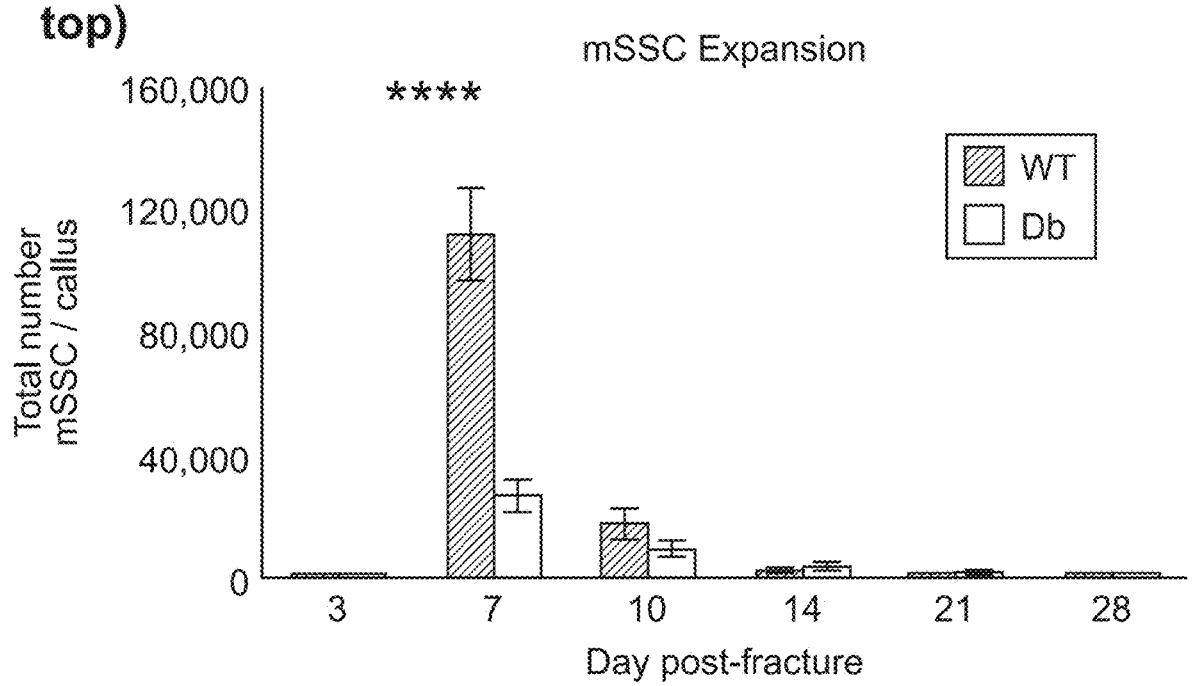
Figure 1G:
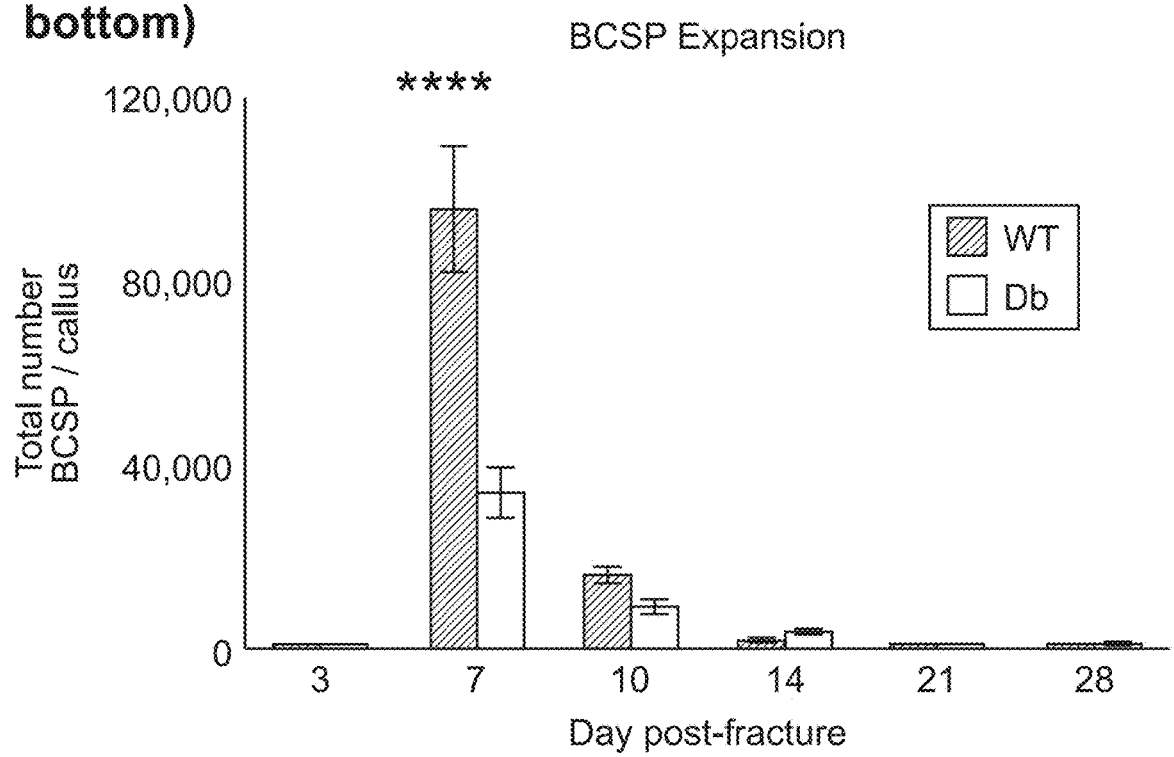
Figure 10D:
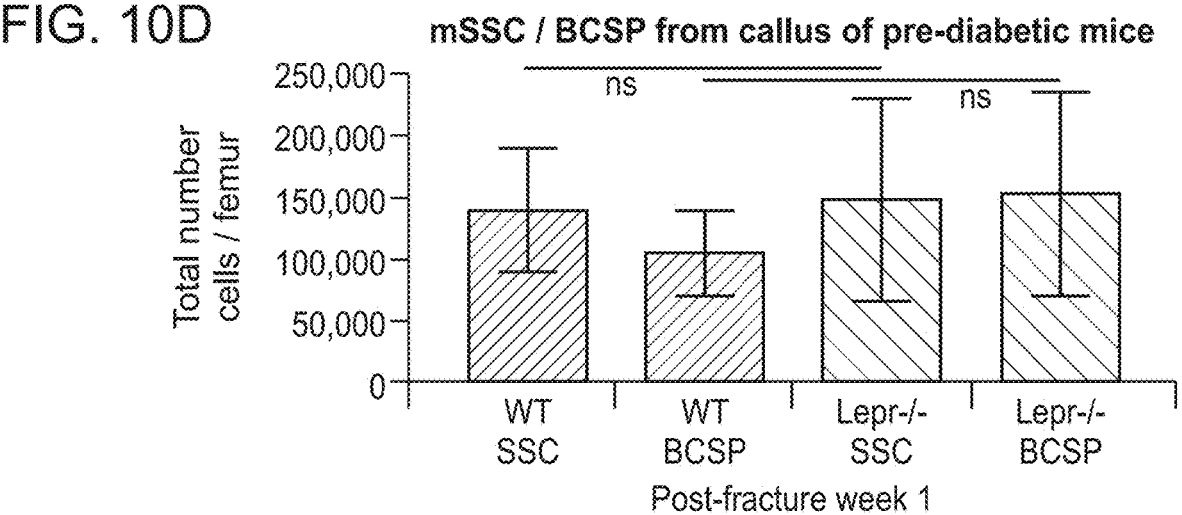
Figure 10E:
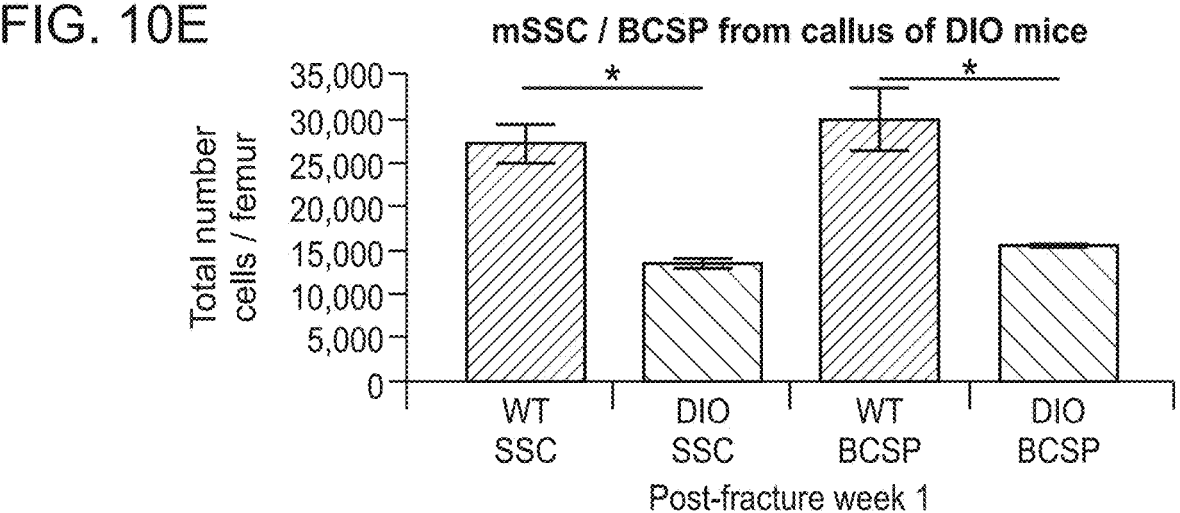
Figure 10F:
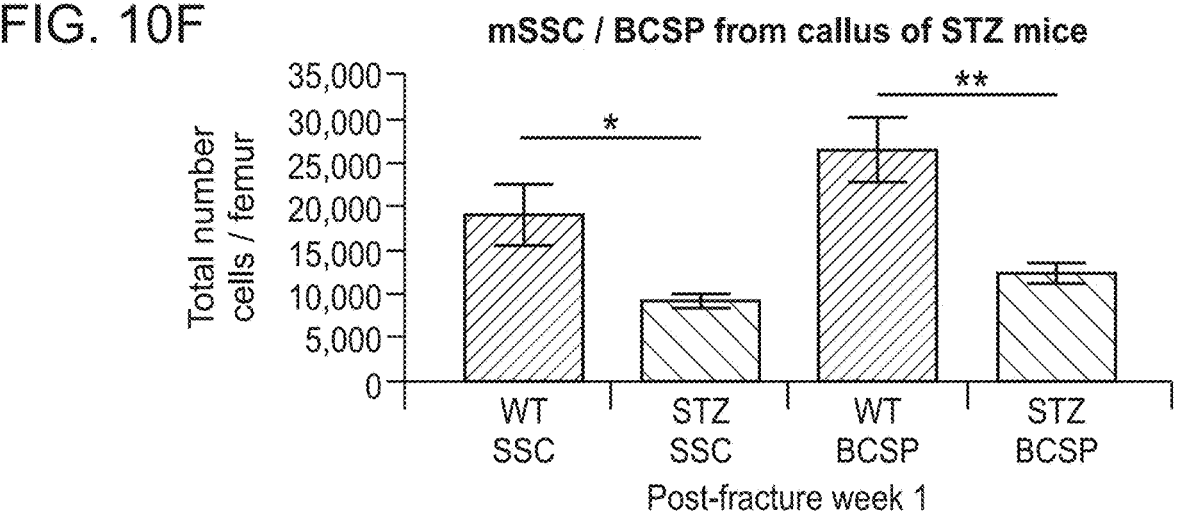
Figure 11A:
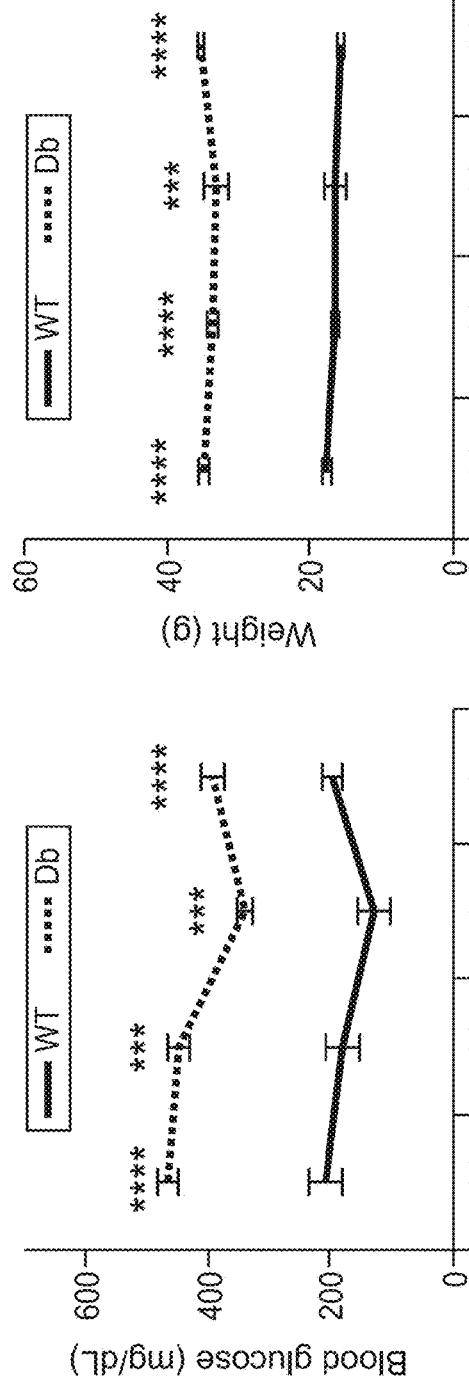
FIG. 11A-11D. Resting glucose and weight between types of diabetic and pre-diabetic mouse models.
Figure 11B:
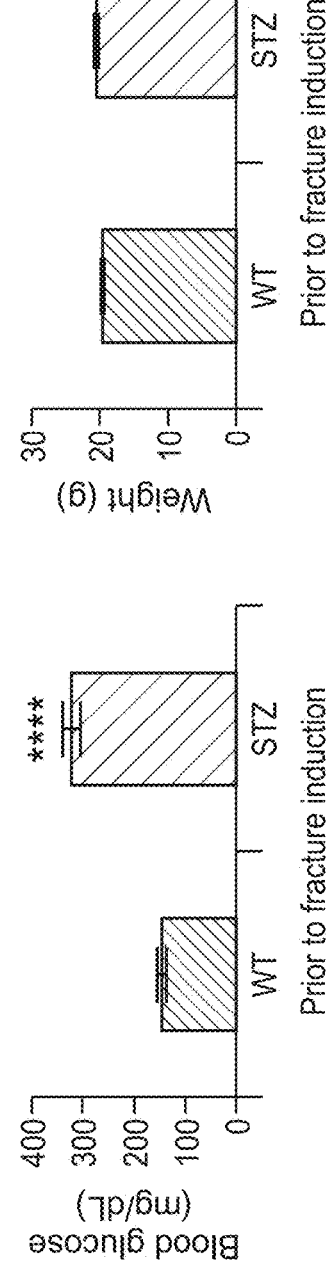
Figure 11C:
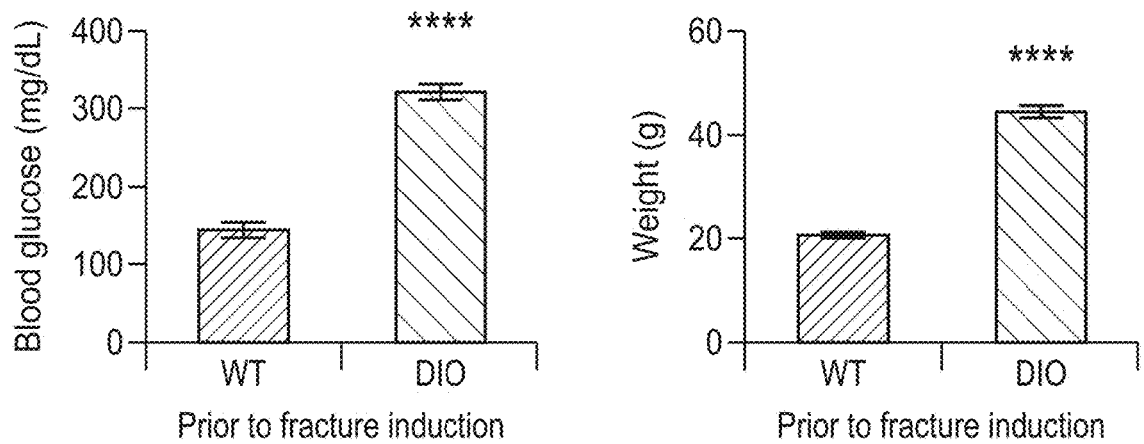
Figure 11D:
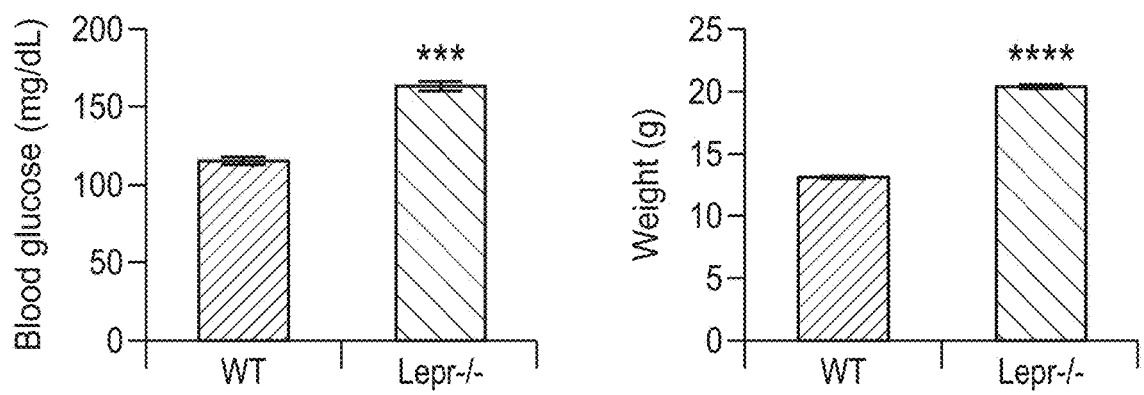

When we assessed the injury-induced expansion of mSSCs and BCSPs within $db_{LR}$ and WT calluses at post-fracture days 3, 7, 14, 21, and 28 (FIG. 1E), there was no significant difference in proportion of the total population for either cell type (FIG. 1F). However, absolute numbers of both mSSCs and BCSPs were significantly reduced in post-fracture day 7 calluses of $db_{LR}$ mice (FIG. 1G). This result is interesting because post-fracture day 7 is a time point previously shown to exhibit maximal mSSC and BCSP expansion in non-diabetic mice. We also observed significantly lower absolute numbers of mSSCs and BCSPs in post-fracture day 7 calluses of $db_{DIO}$ and $db_{STZ}$ mice but not in pre-$db_{LR}$ mice compared to age- and sex matched WT controls (FIG. 10D-F). Together, these results show that mSSC and BCSP injury induced expansion is diminished in several mouse models of DM only when DM is active.

Figure 1H:
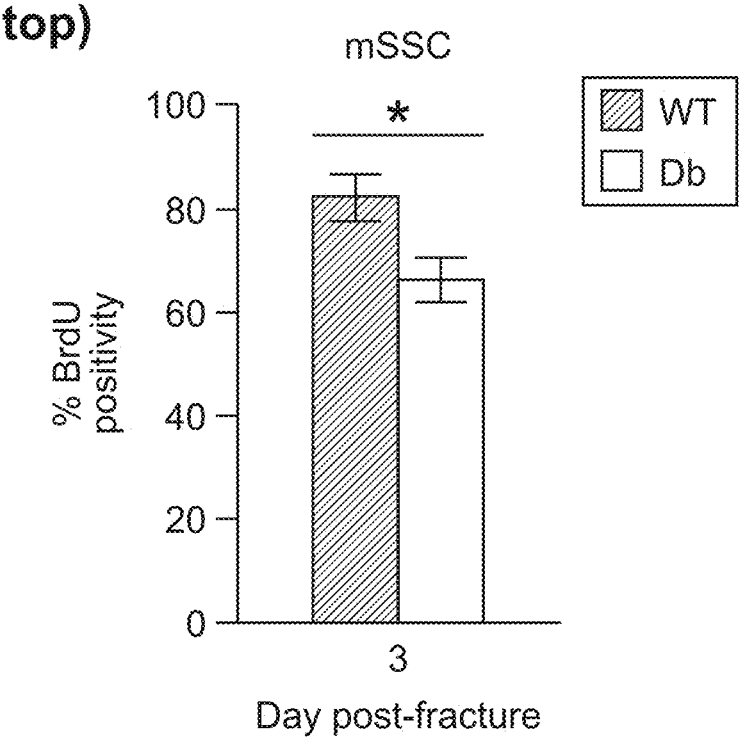
Figure 1H:
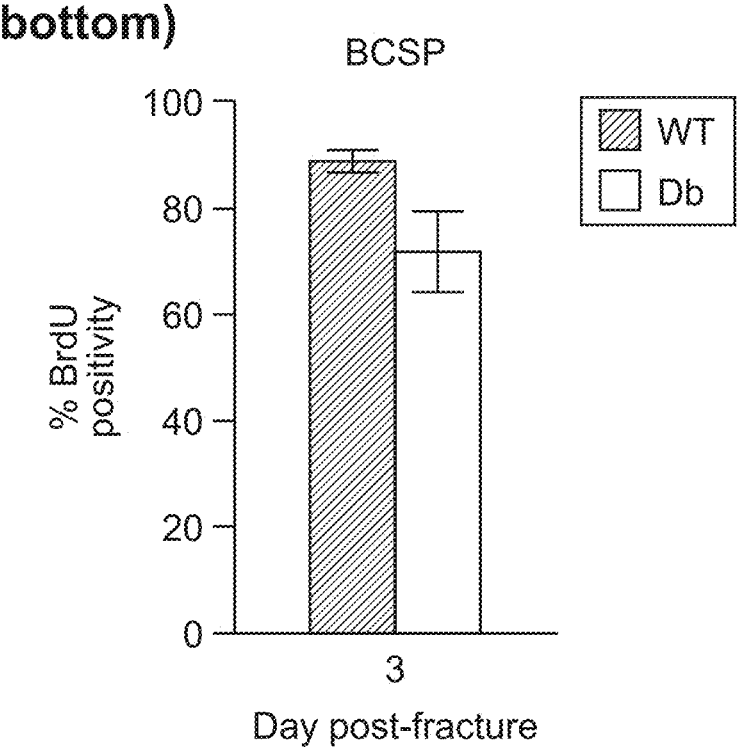
Figure 1I:
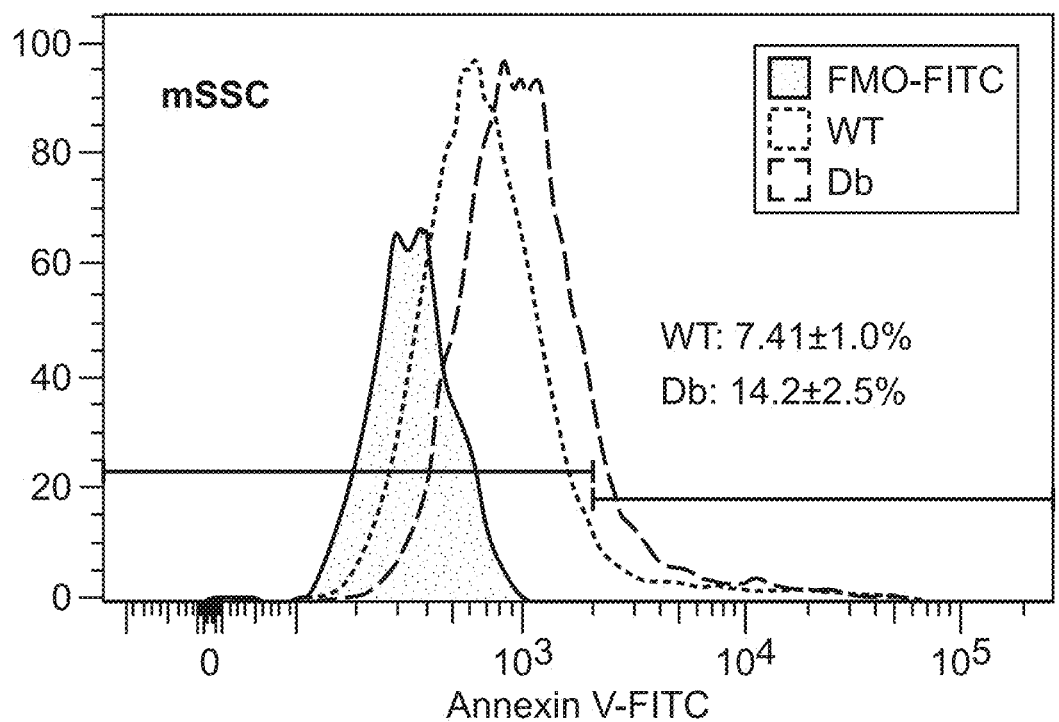
Figure 1I:
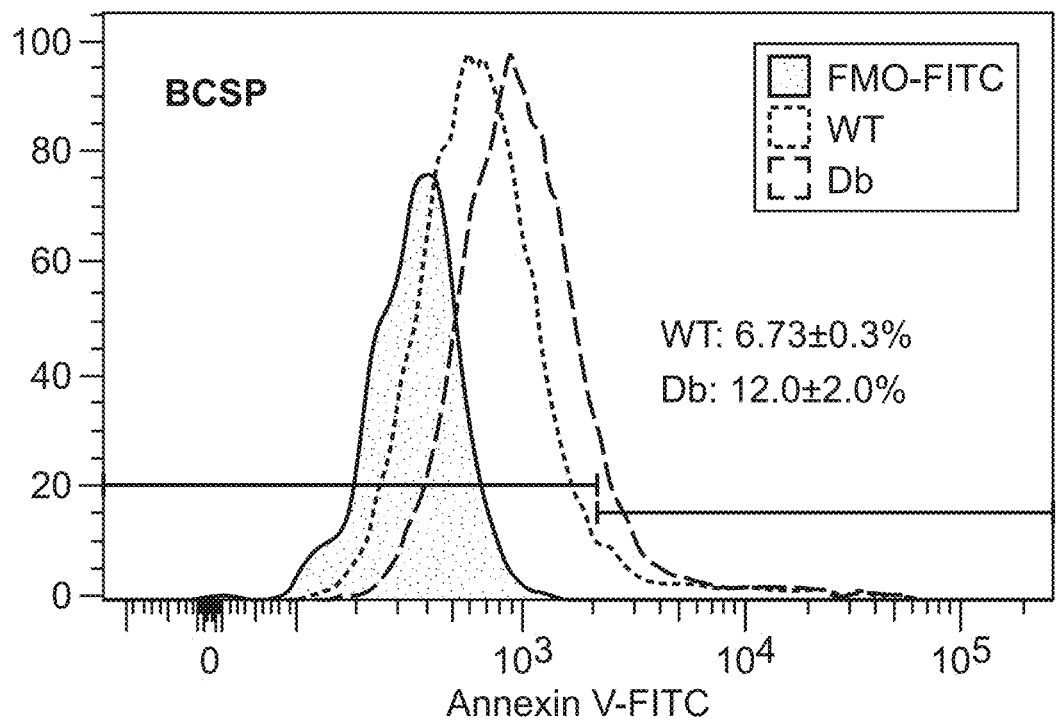

We next tested if differences in cellular proliferation or apoptosis contributed to the deficient stem and progenitor injury response. To assess proliferative activity, we administered 5-bromo-2'-deoxyuridine (BrdU), an intracellular label of rapidly dividing cells, to $db_{LR}$ and WT mice 12 hours prior to FACS analysis on post-fracture day 3. We found that the percentage of BrdU labeled mSSCs was significantly lower in $db_{LR}$ calluses on post-fracture day 3 (FIG. 1H). We then assessed apoptotic activity in mSSCs from post-fracture day 7 calluses using FACS to analyze surface phosphatidylserine staining (measured with FITC-conjugated annexin V). mSSCs from $db_{LR}$ calluses had greater apoptotic activity than those from WT controls (FIG. 1I). Thus, decreased proliferation and increased apoptotic activity of mSSCs contribute to the deficient stem and progenitor injury response in diabetic mice.

Figure 2A:
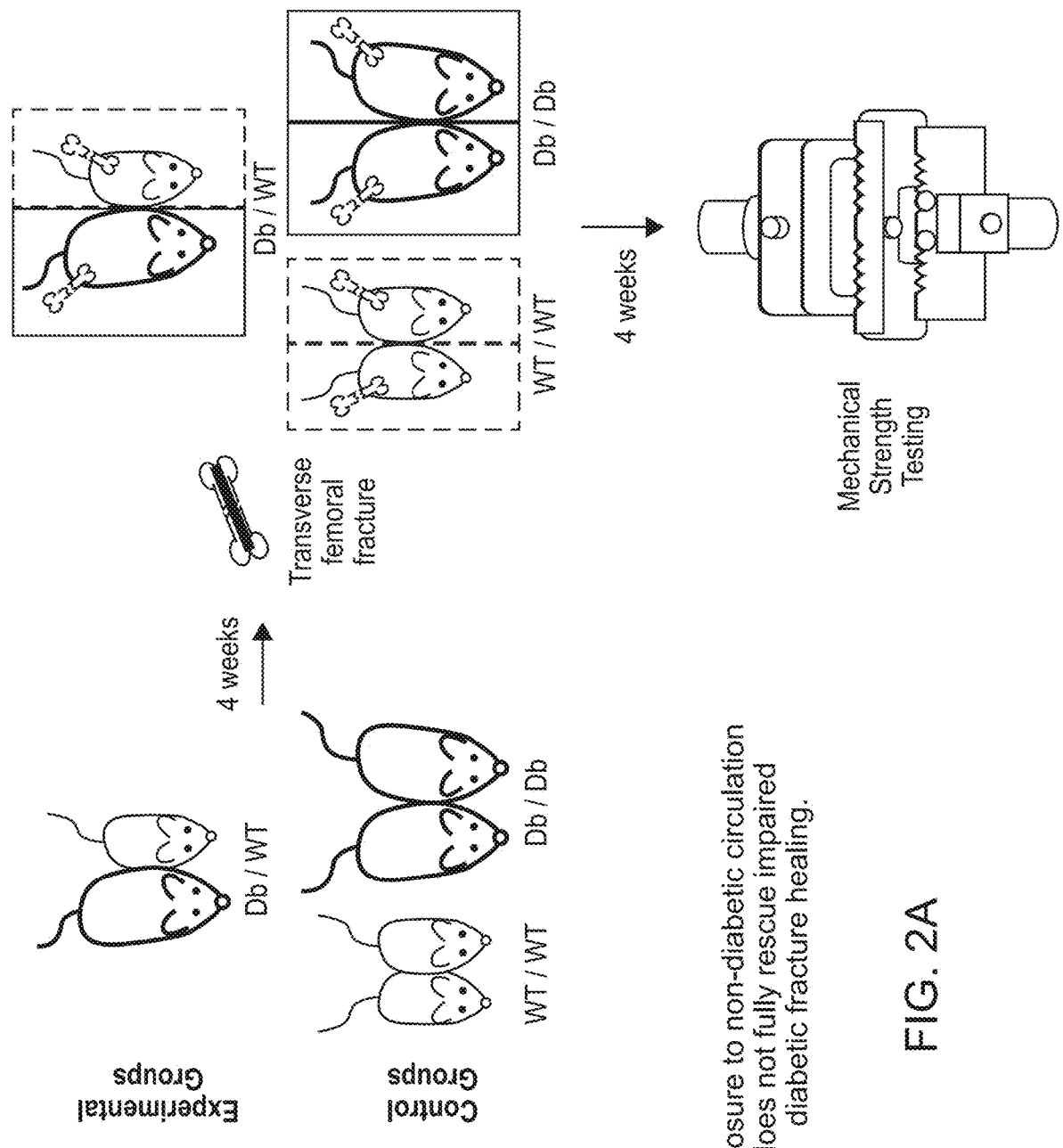
FIG. 2A-2D. Exposure to a non-diabetic circulation does not fully restore diabetic fracture healing.
Figure 2B:
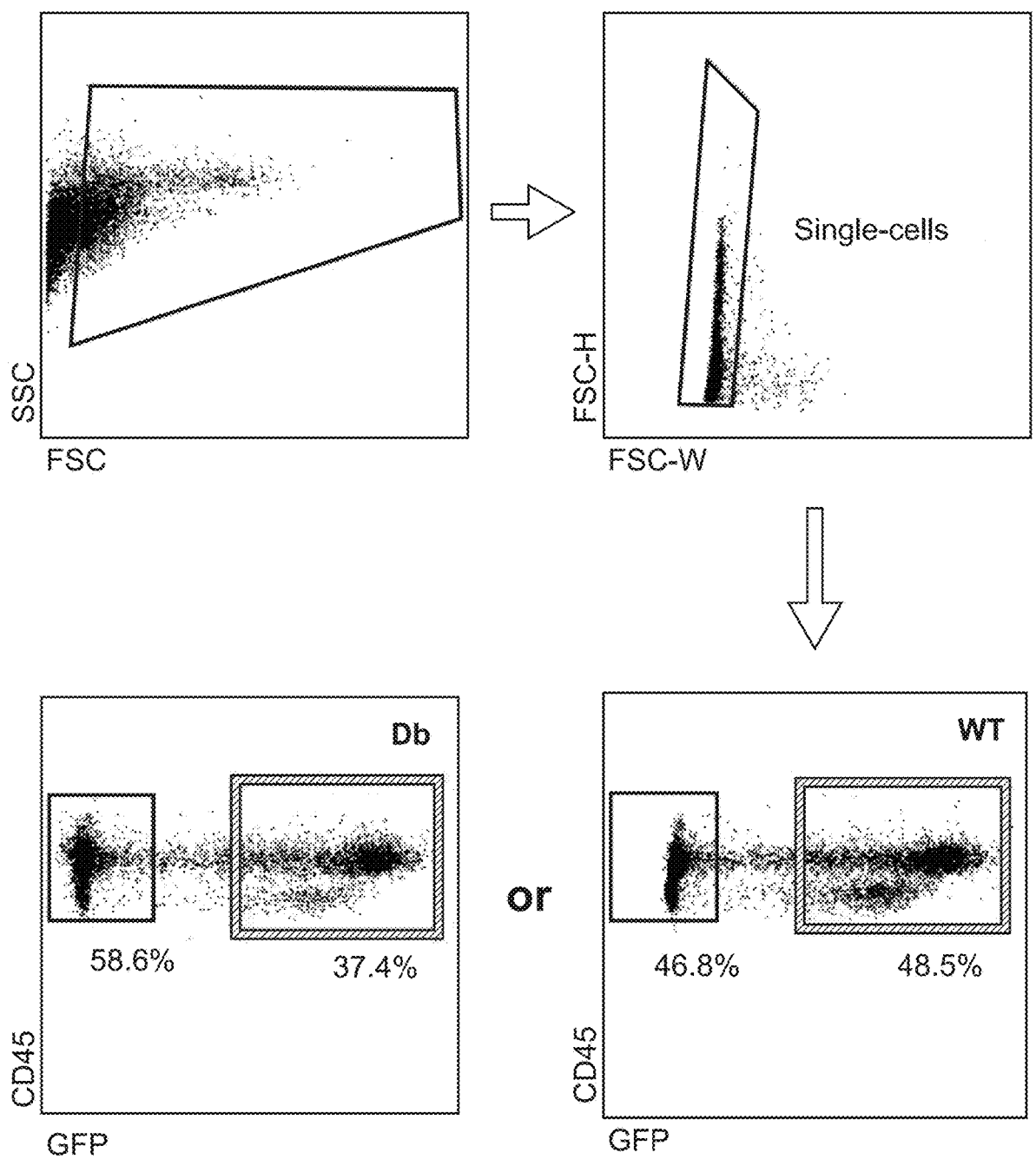
Figure 2C:
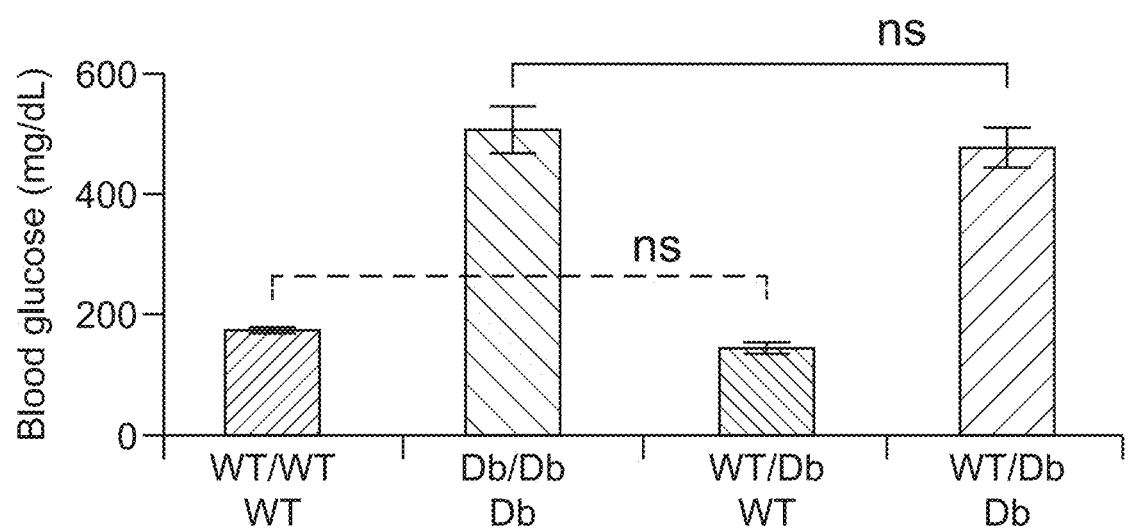
Figure 2D:
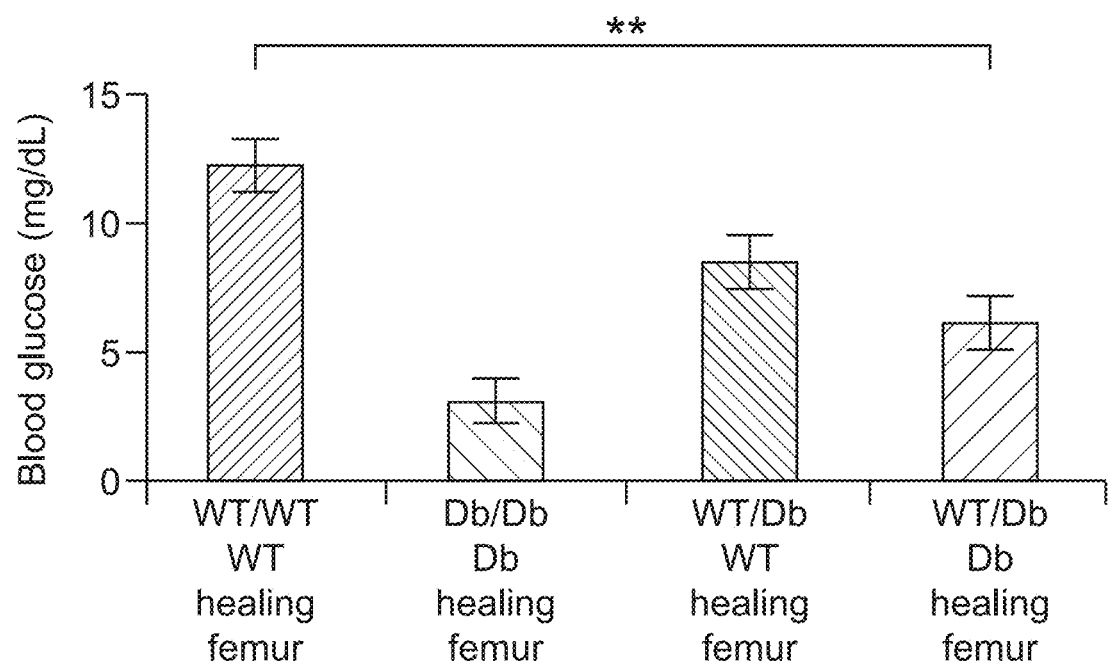

Exposure to non-diabetic circulation does not rescue diabetic fracture healing. Given that exposure to blood circulated from a young animal enhances bone repair in aged animals and that exposure to non-diabetic circulation improves diabetic cutaneous wound healing, we next investigated how exposure to non-diabetic circulation affects diabetic bone healing. We joined age- and sex-matched mice in parabiosis in the following chimeric pairs: WT/$db_{LR}$, $db_{LR}$/$db_{LR}$, and WT/WT (FIG. 2A). Blood chimerism was confirmed at postparabiosis week 4 (FIG. 2B). At postparabiosis week 8, glycemic control was not changed in $db_{LR}$ mice exposed to WT circulation, or vice versa (FIG. 2C). We then created a transverse femoral fracture fixed with an intramedullary pin in each animal of a parabiotic pair and assessed bone healing by MST at post-fracture week 4 (FIG. 2A). MST showed no significant difference in strength between WT femora of WT/$db_{LR}$ and WT/WT pairs or between db femora from WT/$db_{LR}$ and $db_{LR}$/$db_{LR}$ pairs (FIG. 2D). Furthermore, $db_{LR}$ femur strength remained significantly lower than that of WT animals, indicating that exposure to non-diabetic circulation does not rescue diabetic fracture repair.

Figure 3A:
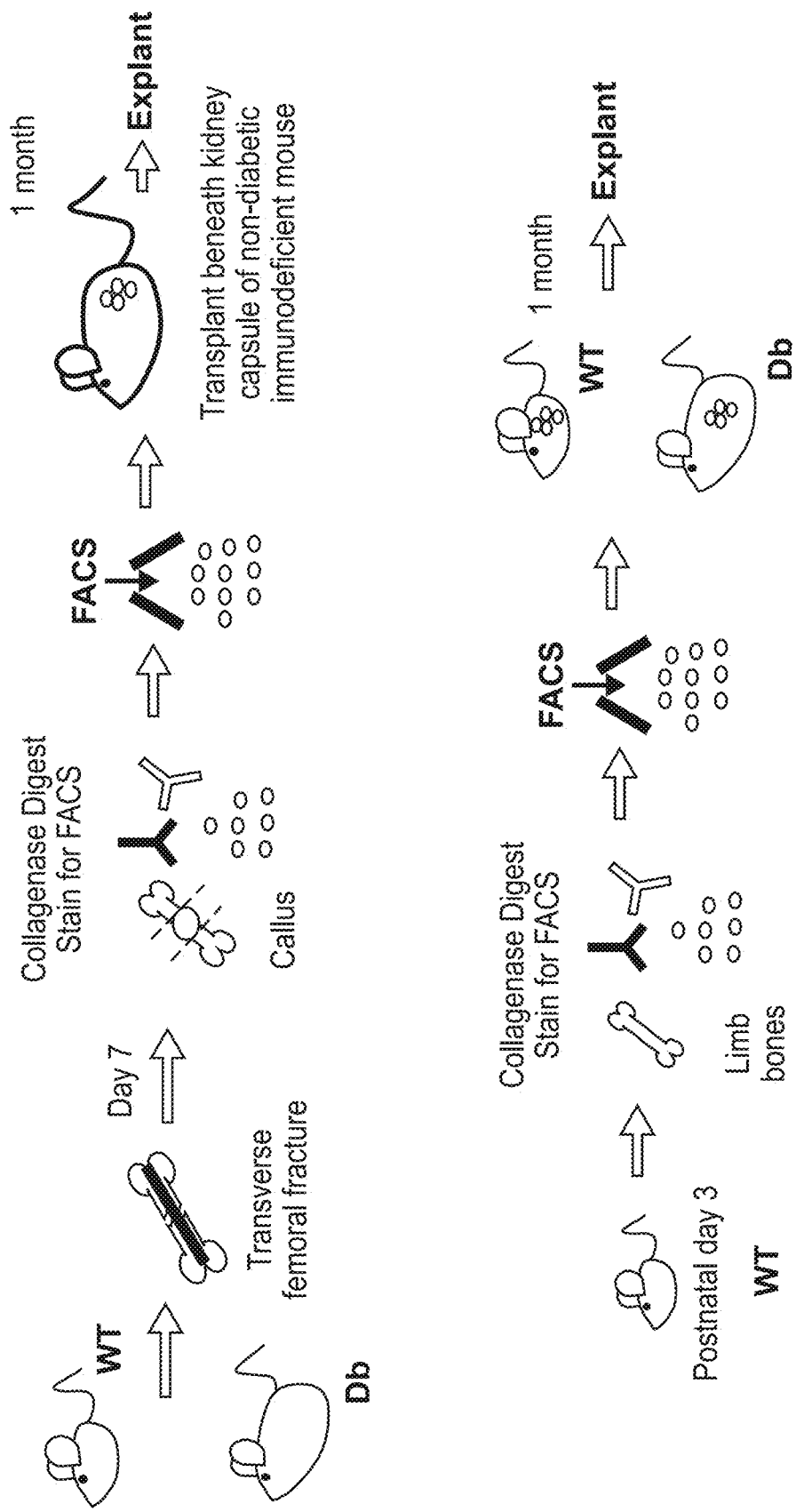
FIG. 3A-3C. Altered mSSC and BCSP skeletogenic activity is cell-extrinsic in diabetic mice.

Cell-extrinsic factors impair mSSC-dependent bone healing in db mice. Having seen reduced mSSC injury expansion in db mice and that exposure to a non-diabetic circulation does not rescue healing, we questioned if intrinsic stem or progenitor cell dysfunction impaired db bone healing. To assess intrinsic cell activity, FACS-sorted mSSCs ($2 \times 10^4$) from post-fracture day 7 calluses of $db_{LR}$ or WT mice were transplanted separately beneath independent kidney capsules of non-diabetic, immunodeficient mice (FIG. 3A). After 4 weeks, heterotopic skeletal grafts were explanted. We hypothesized that if $db_{LR}$ mSSCs were intrinsically dysfunctional, they would produce grafts of a different size and/or composition than those produced by WT mSSCs. Histological analyses determined that the grafts were not significantly different in size (FIG. 3B, far left column) or composition (FIG. 3B, second column from left), suggesting that mSSC-dependent skeletogenesis is not constrained by cell-intrinsic factors in $db_{LR}$ mice.

Figure 3B:
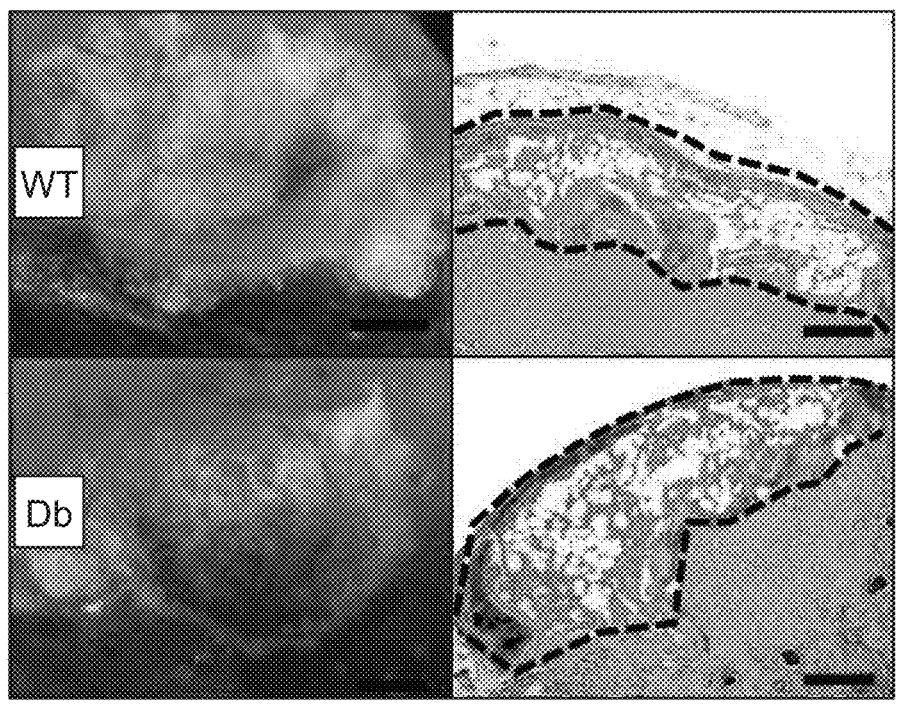
Figure 3B:
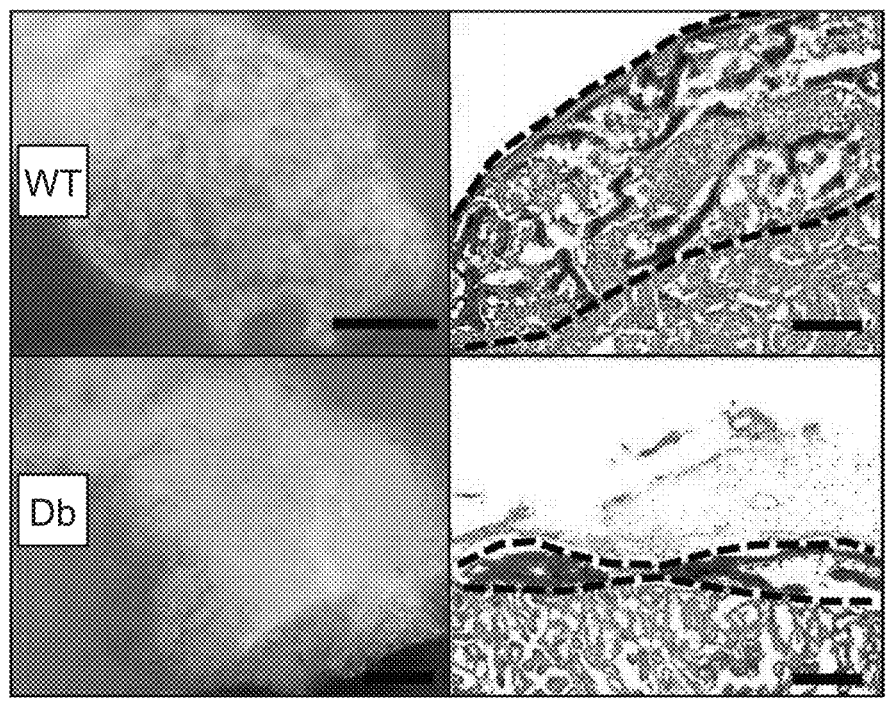
Figure 3C:
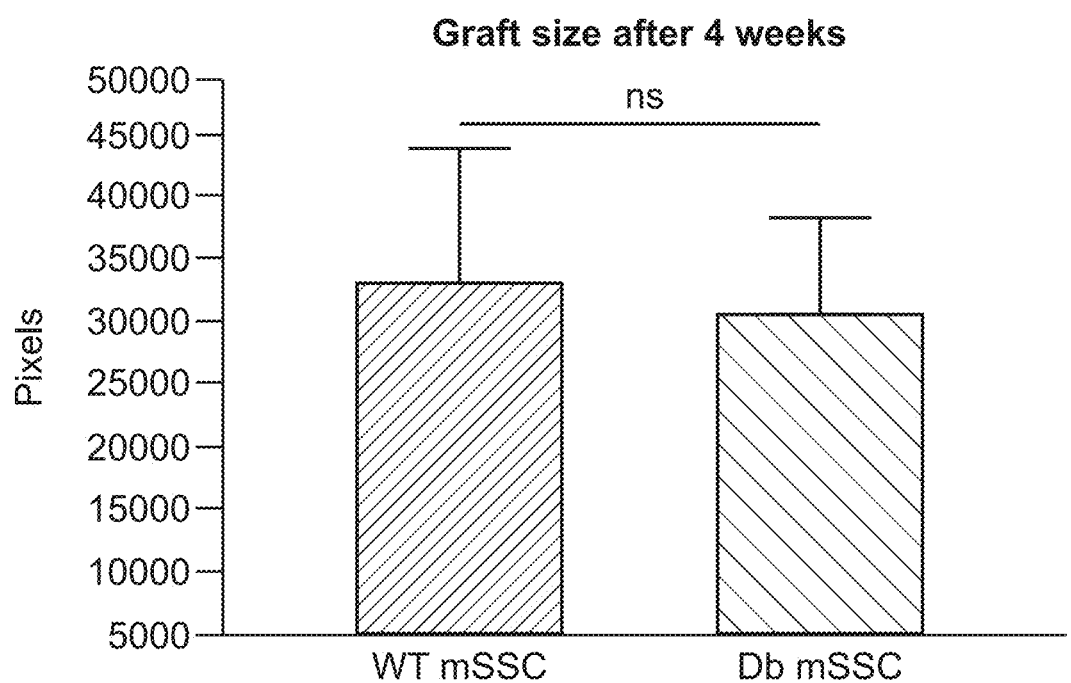
Figure 3C:
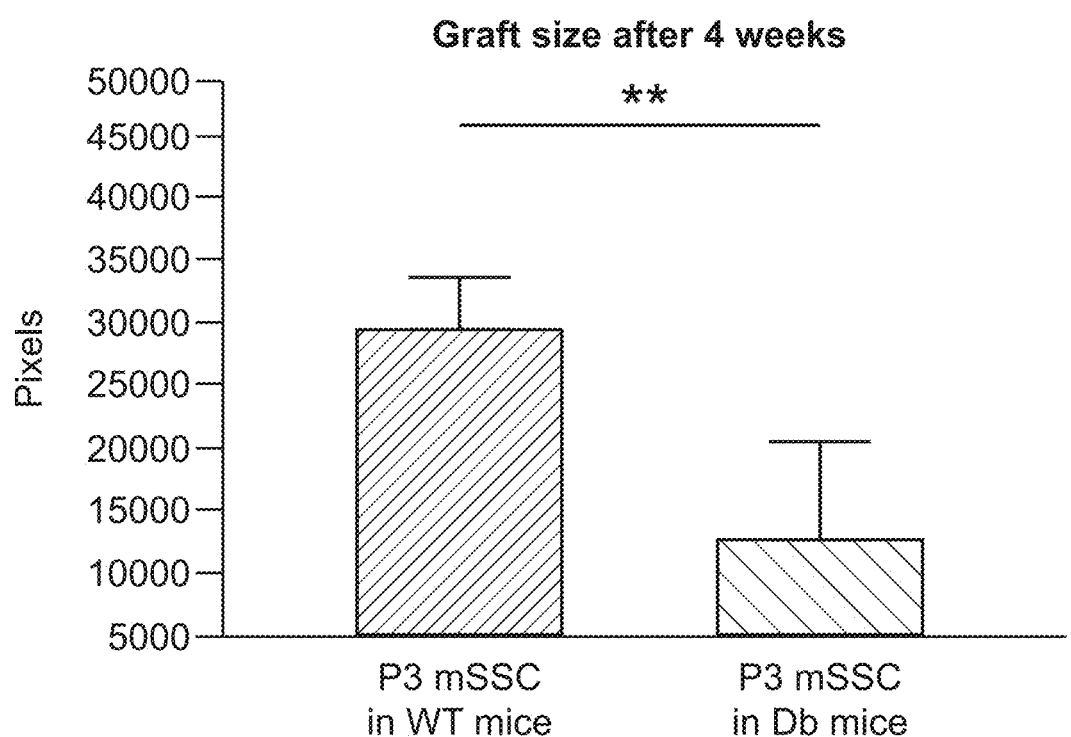

We next investigated if mSSCs are affected by cell-extrinsic factors by transplanting each population ($2 \times 10^4$), isolated from the appendicular skeleton of uninjured WT mice at postnatal day 3 (P3), beneath the kidney capsules of either $db_{LR}$ or WT mice. We hypothesized that if cell-extrinsic factors impaired heterotopic bone formation, grafts derived in $db_{LR}$ mice would differ in size or composition compared to those in WT mice. Histomorphometric analyses revealed that grafts derived in $db_{LR}$ mice differed significantly in size from those in WT mice (FIG. 3B-C, right panel). These results suggest that cell-extrinsic factors, potentially mediated by skeletal niche signaling, alter mSSC skeletogenic potential and could provide a mechanism to impaired db bone healing.

Molecular characterization of the skeletal niche points to therapeutic strategies. To identify molecular changes in skeletal niche signaling that could alter stem and progenitor activity in $db_{LR}$ mice, we compared the transcriptomes of mSSCs and BCSPs from $db_{LR}$ and WT mice using gene chip analysis of extracted mRNA. Each cell population was isolated from uninjured femora and post-fracture day 7 calluses. To elucidate differential gene expression, we analyzed our results using the Gene Expression Commons (GEXC), a system designed by our laboratory to normalize experimental results against publicly available microarray data.

Given the importance of hedgehog (Hh) signaling in skeletal development, we questioned if Hh signaling factors could be differentially expressed during the injury response in $db_{LR}$ and WT mice. Of note, Indian hedgehog (Ihh), a secreted Hh signaling molecule (FIG. 4Ai, first row, black arrow), Smoothened (Smo), a mediator of Hh signal transduction (FIG. 4Ai, fifth row, black arrow), and Gli1, an effector of Hh signaling (FIG. 4Ai, sixth row, black arrow), were downregulated in post-fracture day 7 $db_{LR}$ calluses relative to WT controls.

Figure 4A:
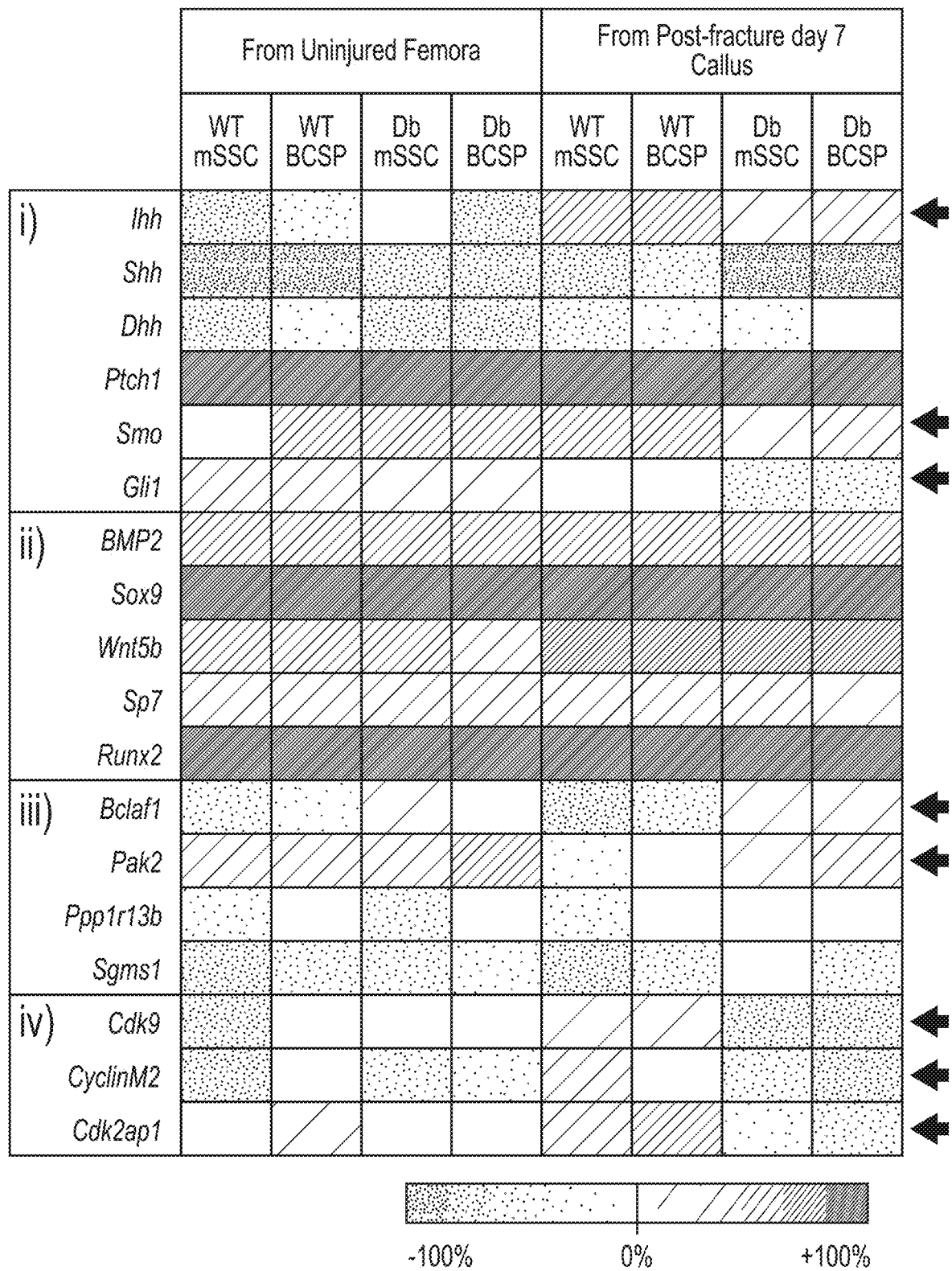
Figure 4B:
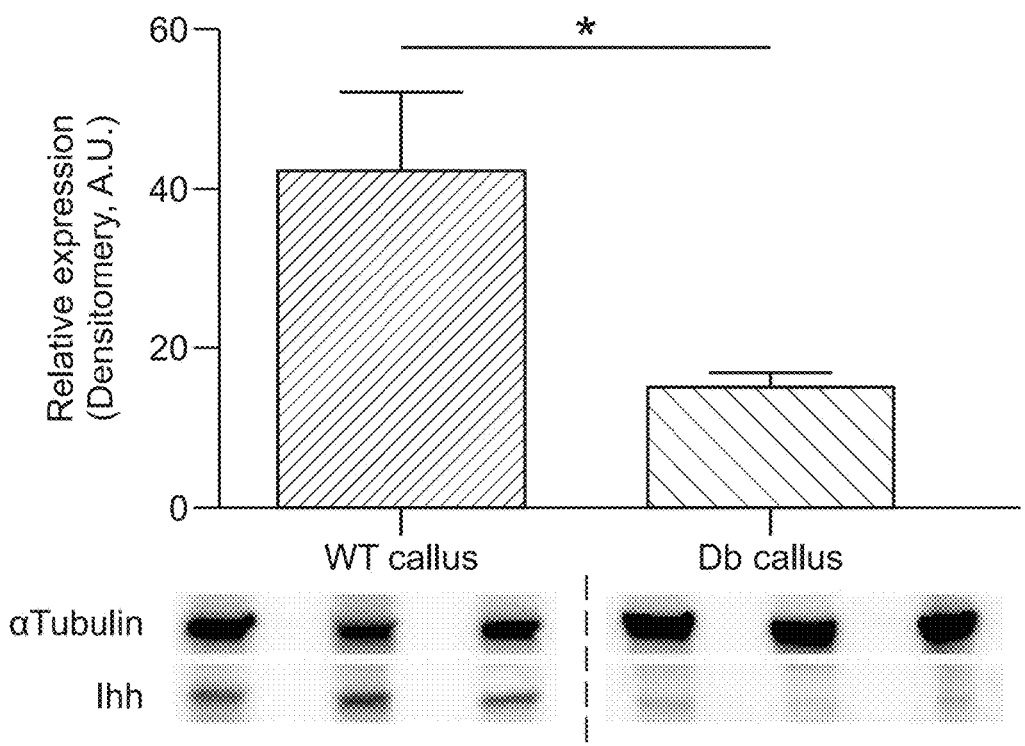
Figure 4C:
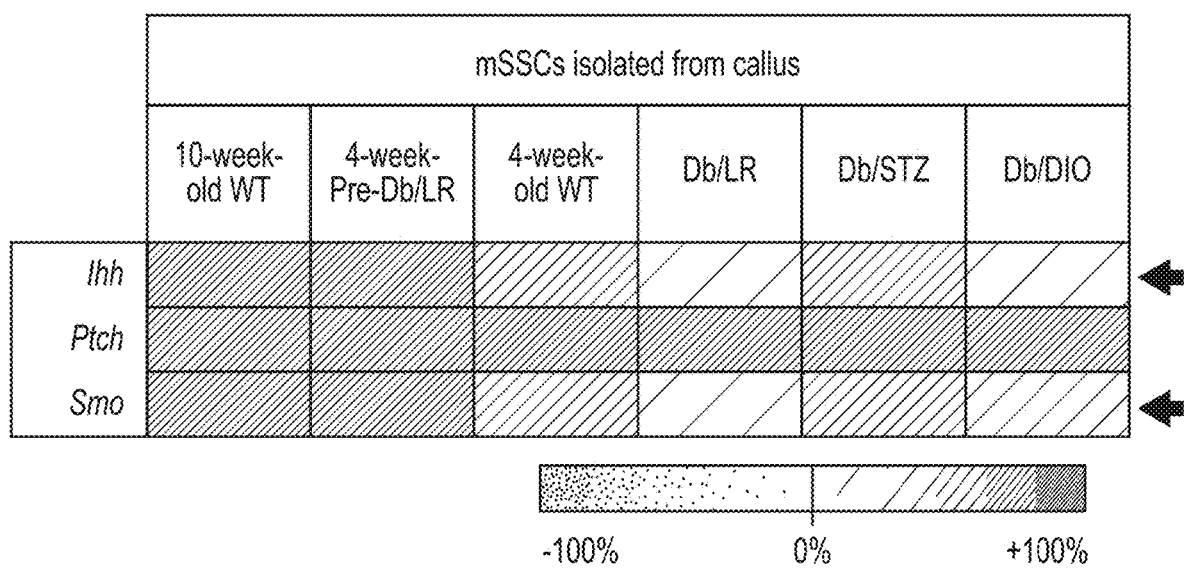

Western blot protein quantification reinforced these findings in FACS-sorted mSSCs isolated from the post-fracture day 7 calluses of $db_{LR}$ and WT mice (FIG. 4B). We also analyzed the expression of Hh signaling factors in $db_{DIO}$ and $db_{STZ}$ mice and found that mSSCs from post fracture day 7 calluses also showed downregulated Ihh and Smo expression relative to those from WT mice (FIG. 4C). Notably, this effect was not seen in mSSCs from post-fracture day 7 calluses of pre-$db_{LR}$ mice, which instead had expression patterns resembling those of their age and sex-matched non-diabetic controls (FIG. 4C). These results indicate that Hh signaling is altered in multiple mouse models of active DM.

In contrast, the expressions of other essential skeletogenic genes, such as WNT and bone morphogenic protein (BMP), were not significantly altered in post-fracture day 7 db mSSCs (FIG. 4Aii). We also found that genes involved in apoptosis were up-regulated and genes involved in cellular proliferation were down-regulated in post-fracture day 7 $db_{LR}$ mSSCs and BCSPs (FIG. 4Aiii-iv).

Figure 4D:
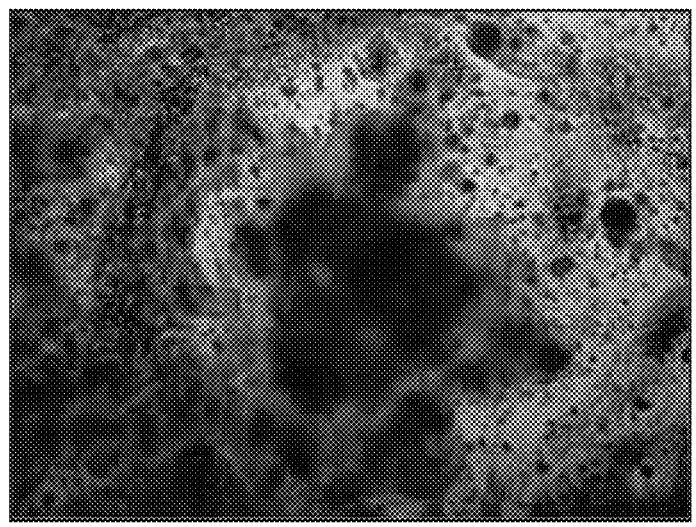
Figure 4D:
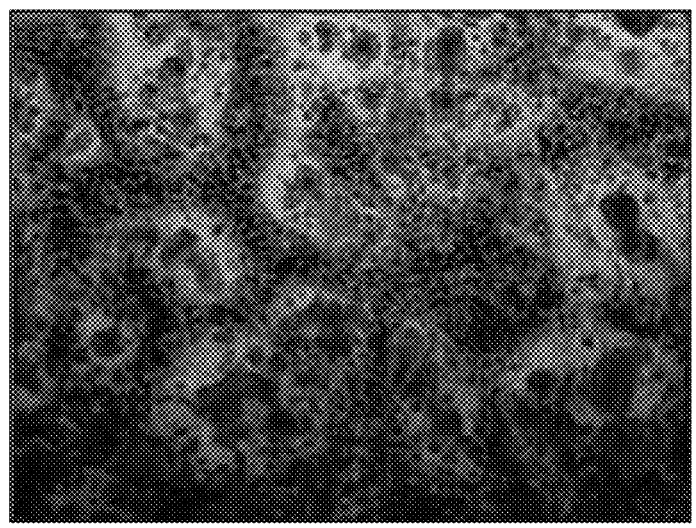
Figure 4D:
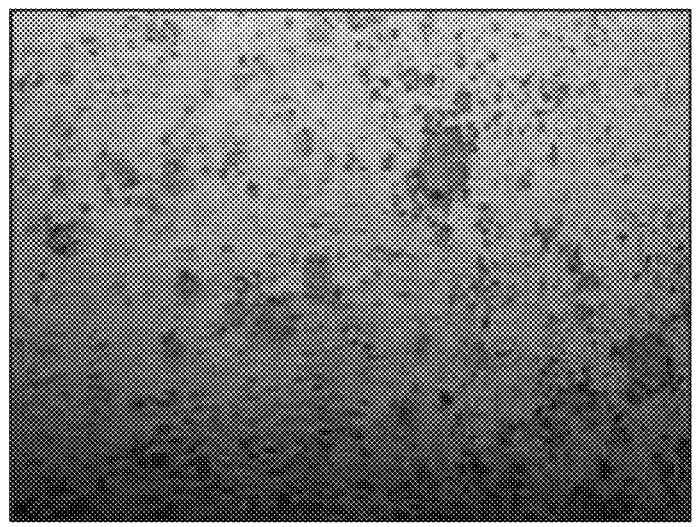

To investigate if Hh signaling is essential for mSSC-dependent osteogenesis, we antagonized Hh signaling in post-fracture day 7 WT mSSCs in vitro using XL139, a small molecule antagonist of Smo. We then assessed bone formation using alizarin red staining, a marker of extracellular matrix mineralization, and found a dose-dependent reduction in the osteogenic potential of mSSCs treated with XL139 (FIG. 4D).

Figure 4F:
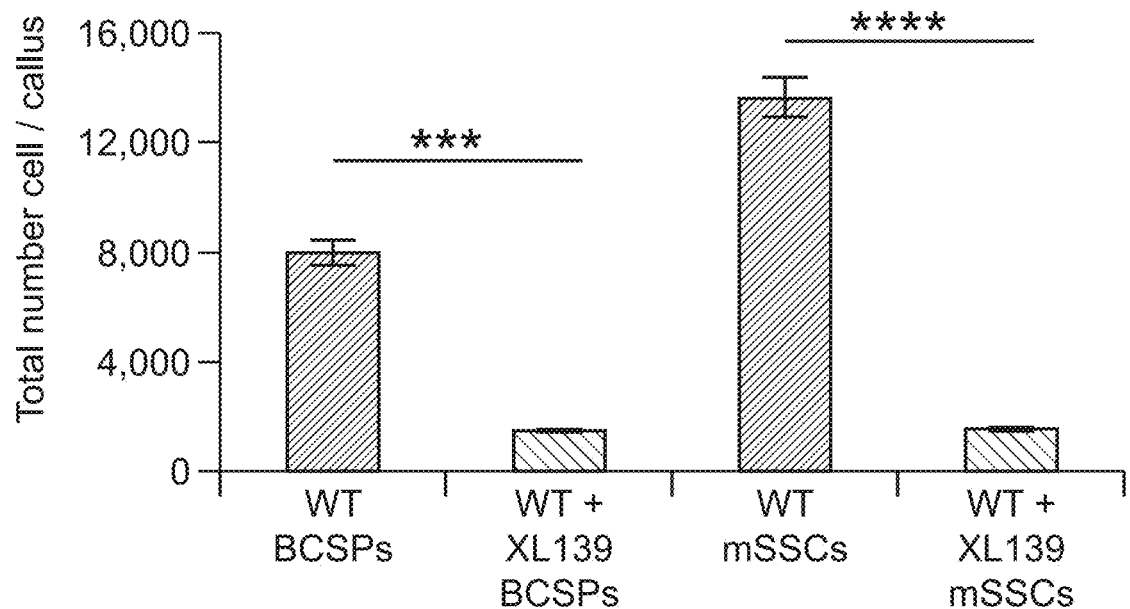

To verify that Hh antagonism impairs fracture repair in vivo, we administered XL139 to WT mice via oral gavage immediately after injury and assessed healing femur strength at post-fracture week 4 using MST. We found that femur strength was reduced significantly in XL139-treated versus untreated mice (FIG. 4E). We then isolated mSSCs and BCSPs from post-fracture day 7 calluses of XL139-treated versus untreated mice and found a highly significant reduction in the number of mSSCs and BCSPs following Hh antagonism (FIG. 4F).

Figure 4G:
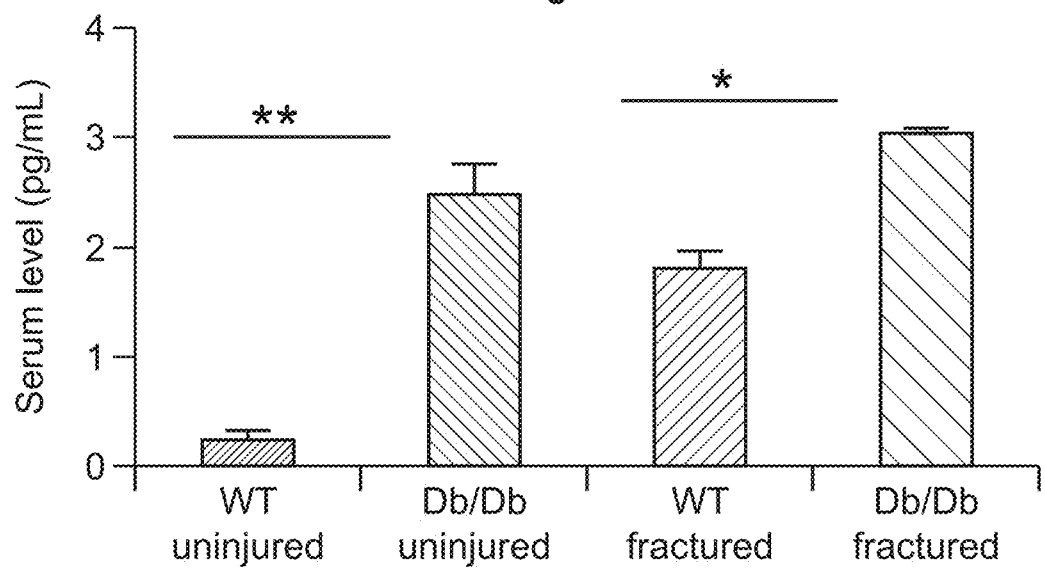
Figure 12:
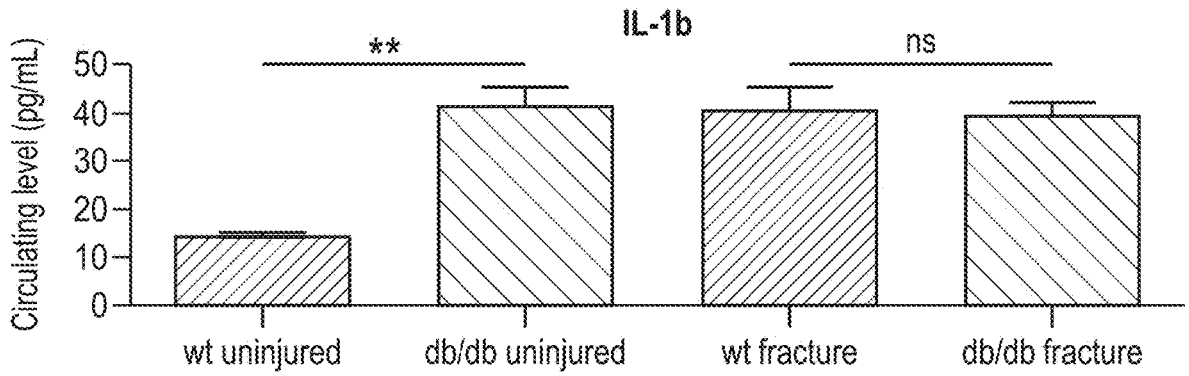
FIG. 12. Circulating IL-1b is elevated in both uninjured and injured db mice. Pre- and post-fracture serum levels of IL-1b in $db_{LR}$ (red) versus WT mice (blue). Data and error bars represent means±SEM. **p<0.01, n=3, unpaired two-tailed t-test.

To understand why Hh expression was repressed specifically in the skeletal niches of db mice, we first performed proteomic analyses on $db_{LR}$ and WT serum to identify systemic factors that could disrupt niche signaling. We found significantly higher levels of glucose and inflammatory cytokines such as TNFα and IL-1b in $db_{LR}$ mice (FIG. 4G: TNFα; FIG. 11: glucose; FIG. 12: IL-1b). Single-cell RNA-sequencing (scRNA-seq) revealed that TNFα receptors are co-expressed with Ihh, Ptch1, and Gli1 on both mSSCs and BCSPs isolated from post-fracture day 7 calluses of $db_{LR}$ mice (FIG. 5A-D).

Figure 5A:
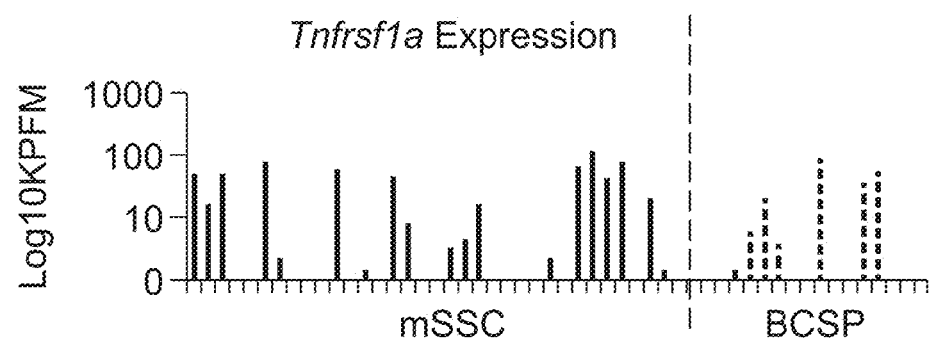
FIG. 5A-5J. Increased levels of TNFα directly suppress Ihh expression in skeletal progenitors.
Figure 5B:
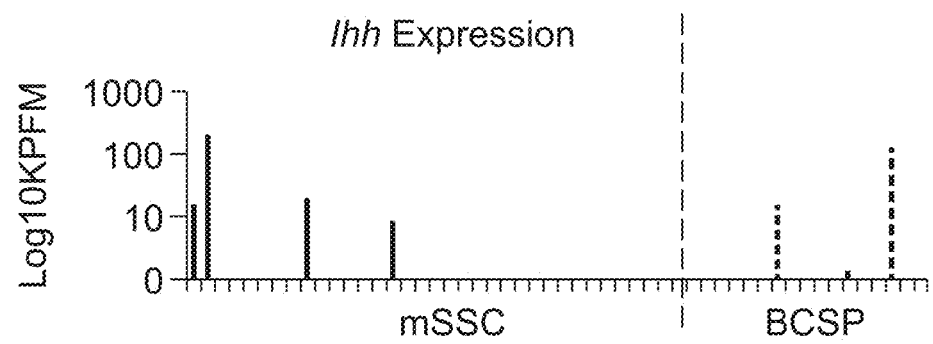
Figure 5C:
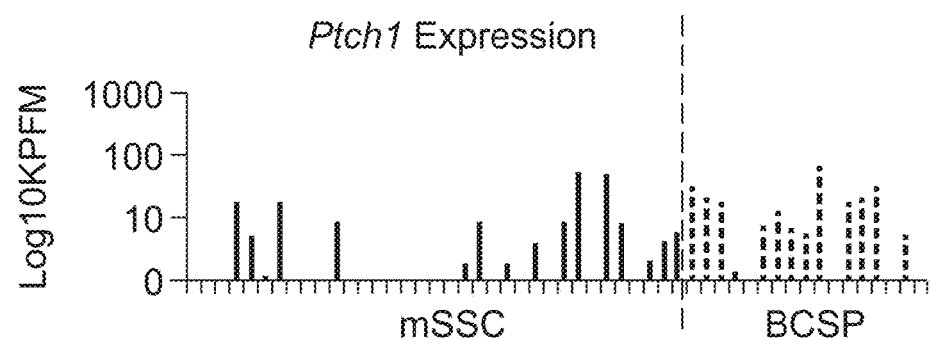
Figure 5D:
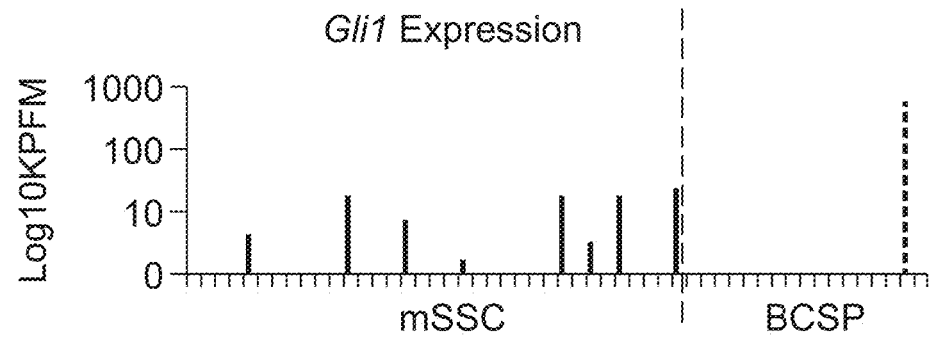
Figure 5E:
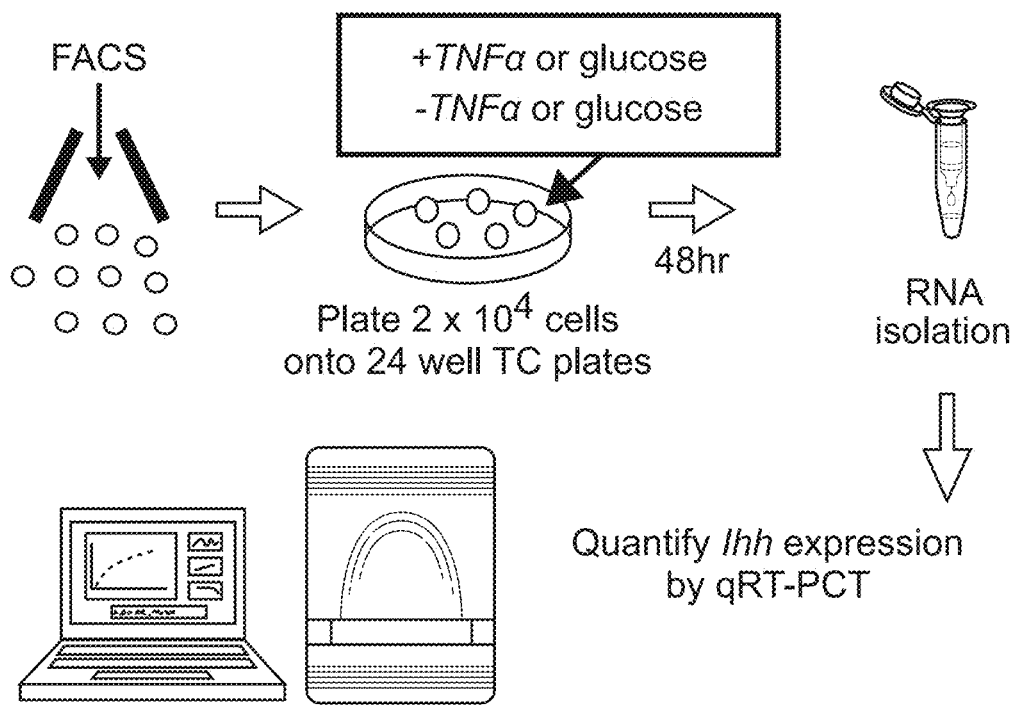
Figure 5F:
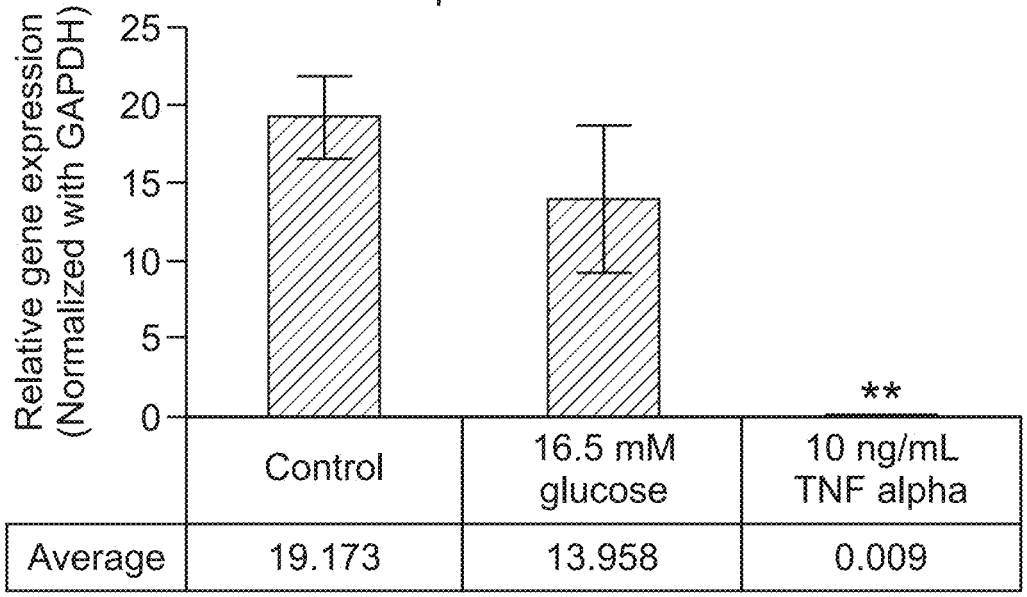
Figure 5G:
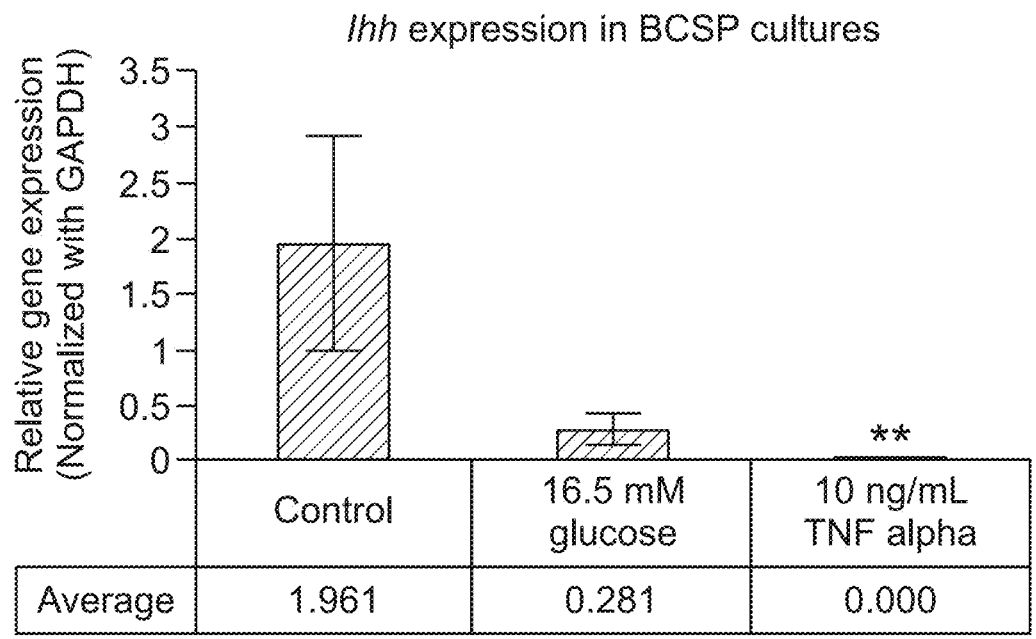
Figure 5H:
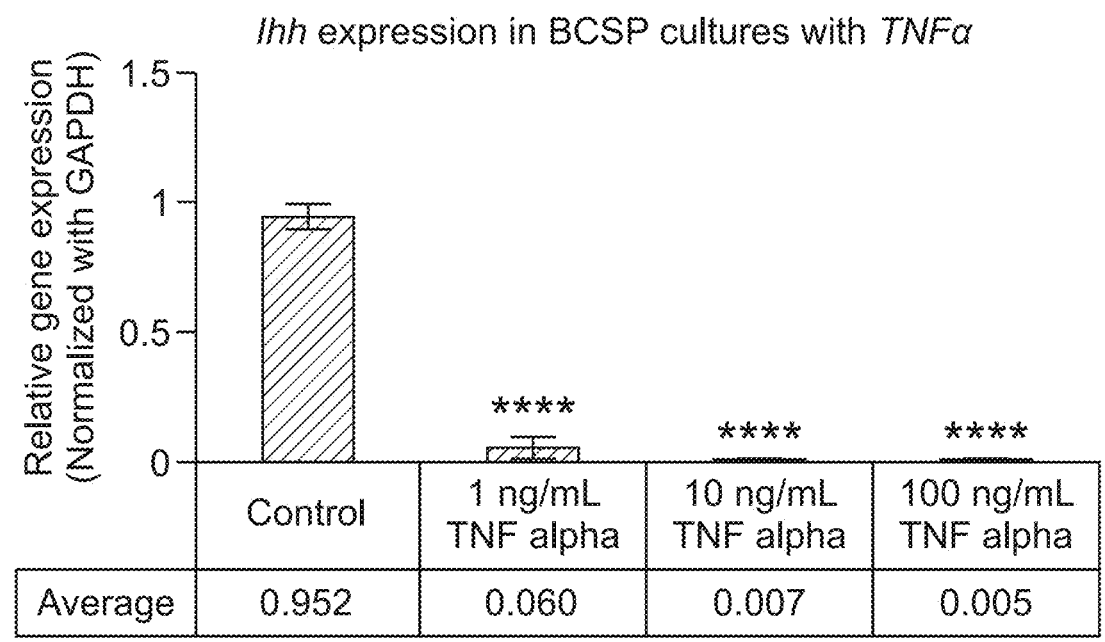
Figure 5I:
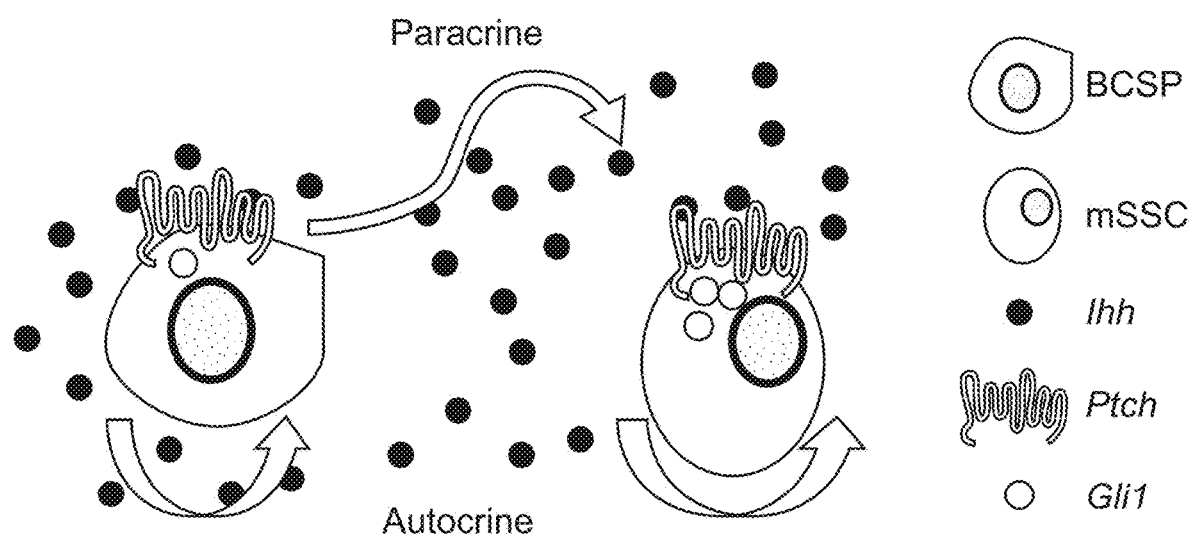
Figure 5J:
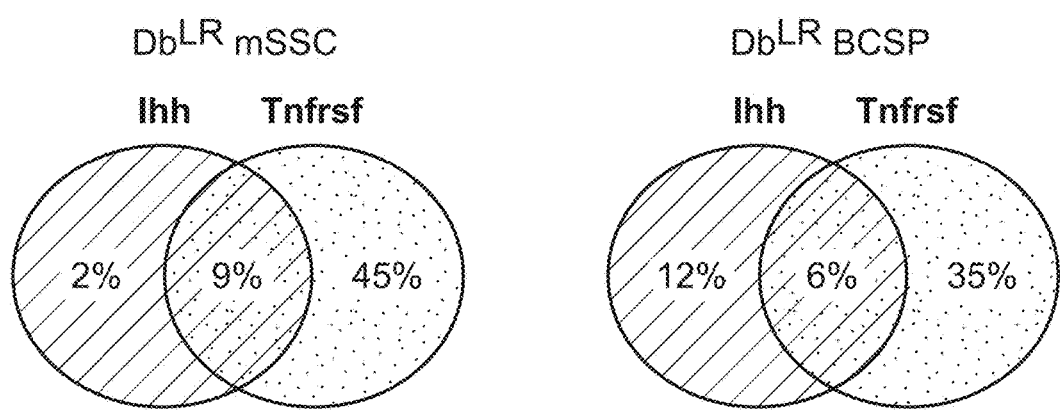

To determine if high levels of glucose or TNFα could directly repress Hh expression in skeletal niches, we cultured FACS-sorted mSSCs and BCSPs from uninjured P3 WT femora in glucose-supplemented, TNFα-supplemented, or control media for 48 hours. We then measured Ihh expression using quantitative reverse transcriptase-polymerase chain reaction (qRT-PCR) and found that Ihh expression was significantly reduced in both mSSC and BCSP cultures supplemented with TNFα but not in mSSC cultures supplemented with glucose (FIG. 5E-G). Interestingly, the inhibition of Ihh expression by glucose in BCSPs suggests that while TNFα alters Hh signaling at the stem cell level, glucose alters Hh signaling in the stem cell's downstream progenitors. This TNFα-mediated repression of Ihh expression was dose dependent in BCSPs (FIG. 5H). Furthermore, neutralization of TNFα with anti-TNFα antibodies restored Ihh expression levels in mSSCs cultured in $db_{LR}$ serum (FIG. 15). Cumulatively, these data indicate that systemically elevated levels of TNFα could suppress Ihh signaling, potentially disrupting essential pro-skeletogenic autocrine and/or paracrine crosstalk between mSSCs and BCSPs (FIG. 5I-J).

Figure 6A:
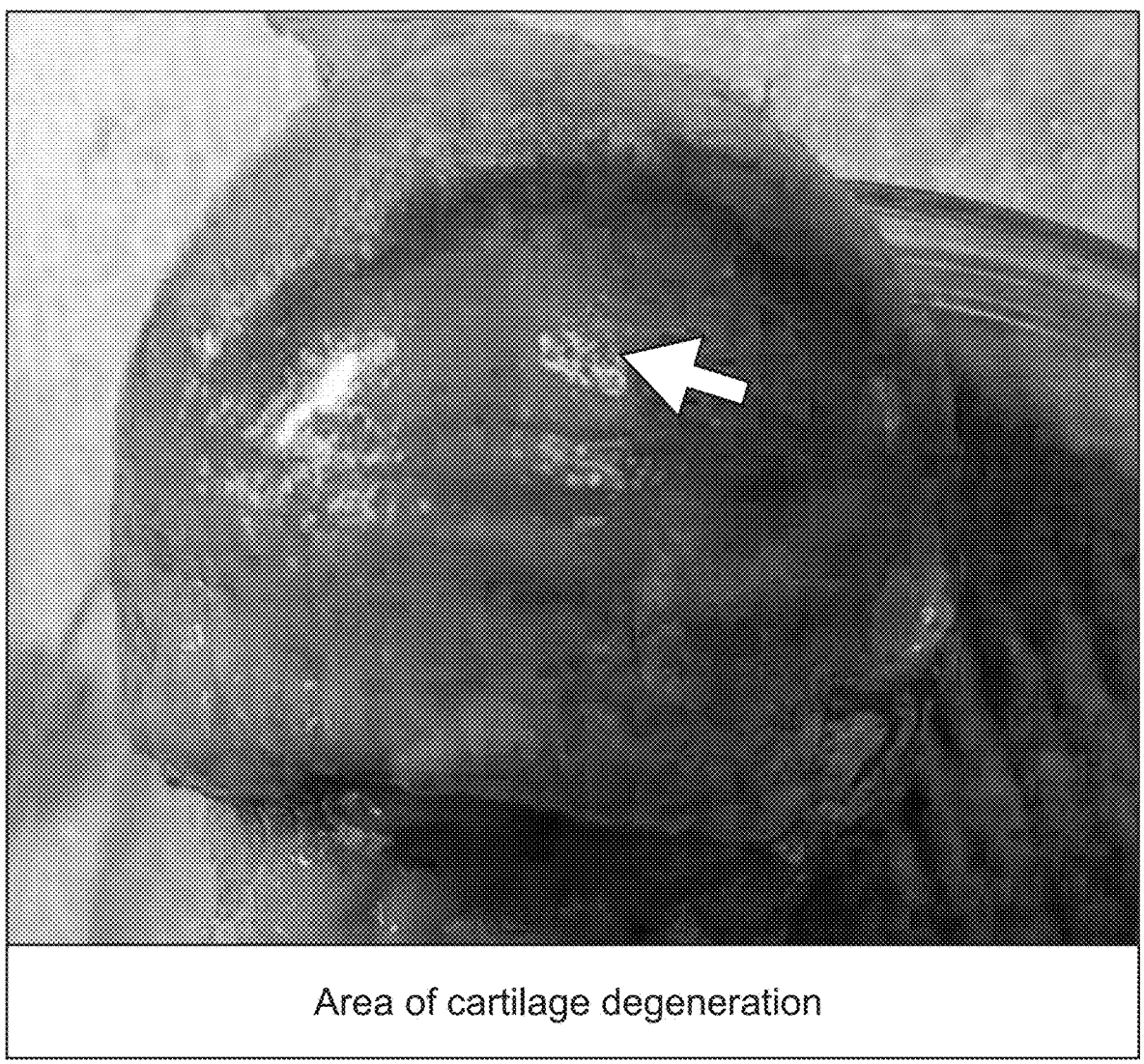
FIG. 6A-6D. Indian Hedgehog and Gli1 expression are repressed in diabetic human skeletal progenitors.
Figure 6B:
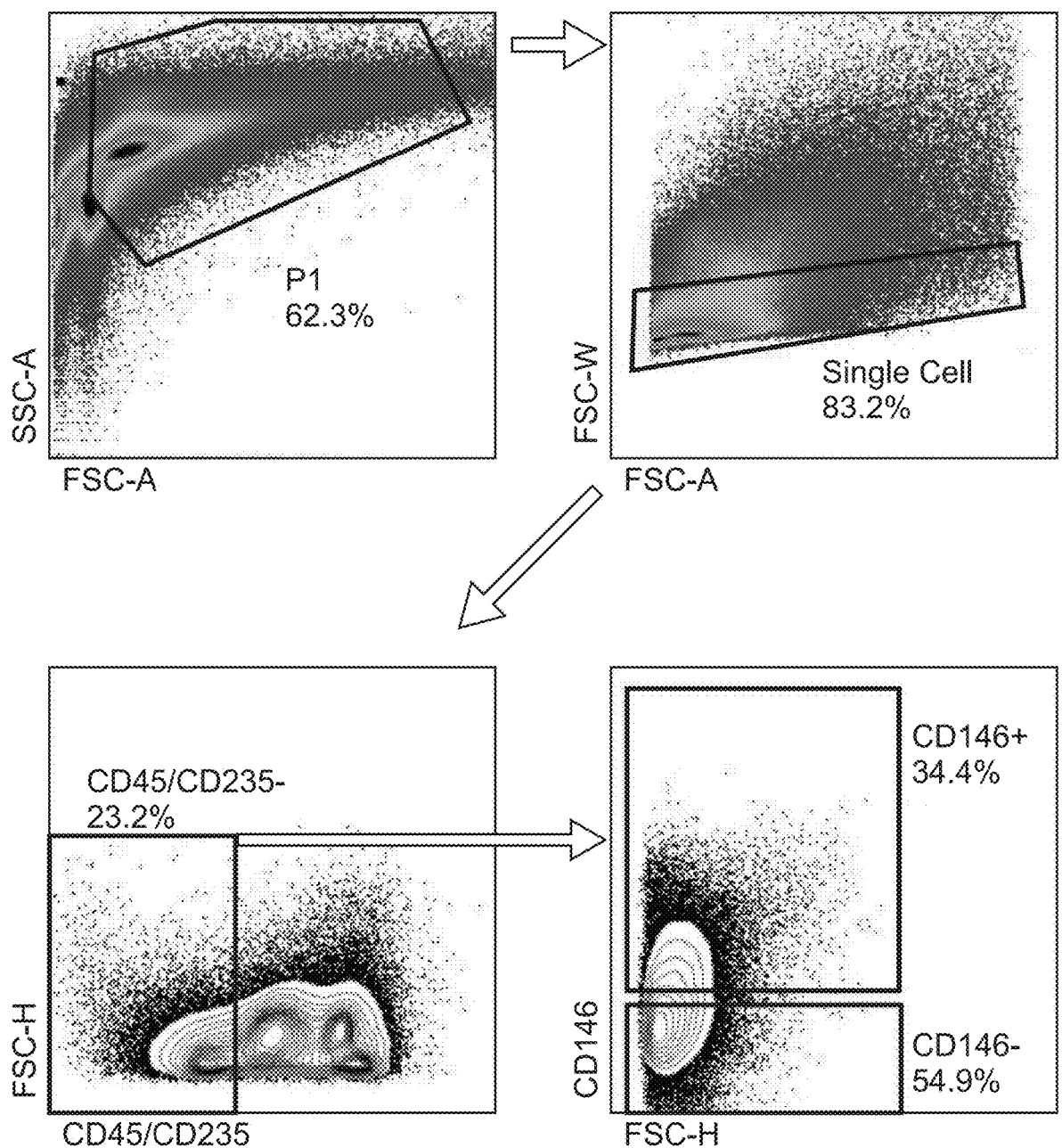
Figure 6C:
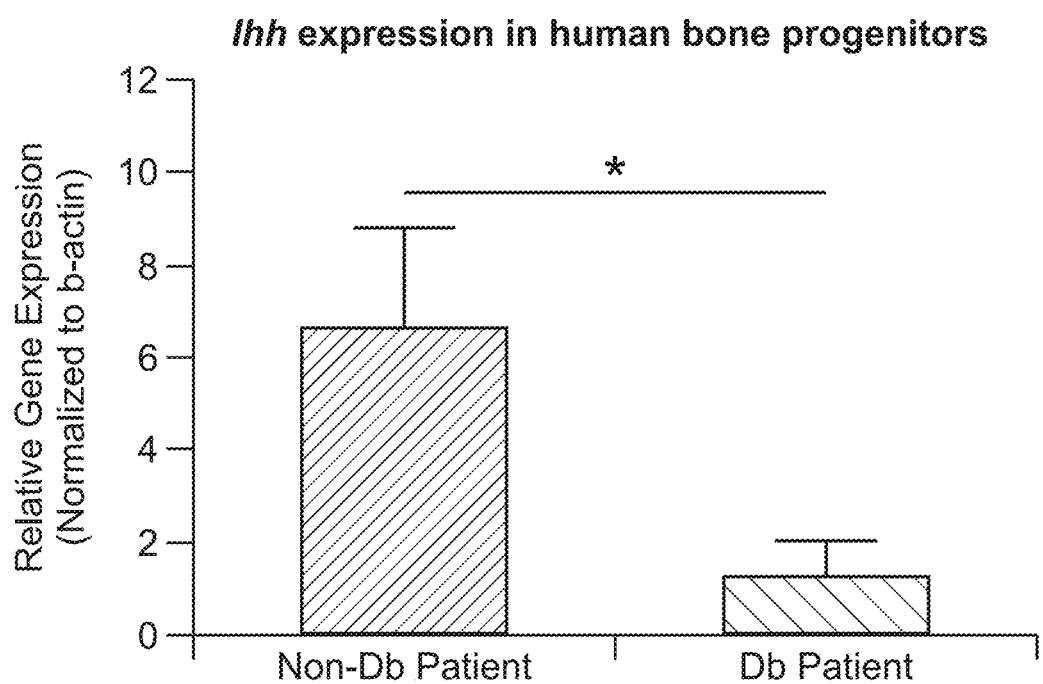
Figure 6D:
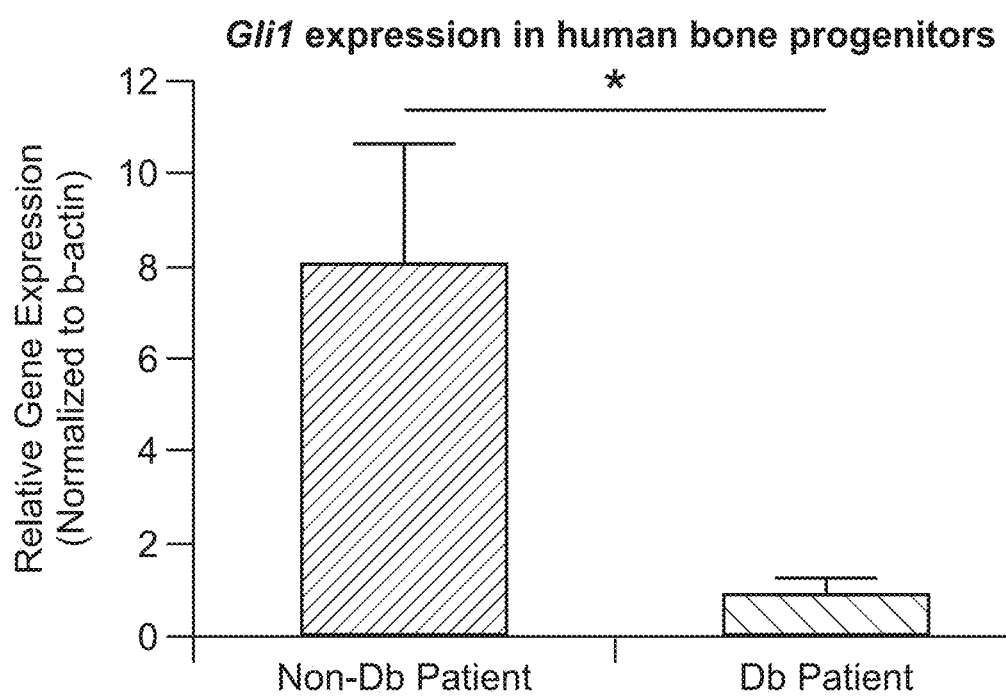

Indian hedgehog and Gli1 expression are repressed in diabetic human skeletal progenitors. As diabetic patients also exhibit high levels of TNFα, we investigated if human diabetic skeletal progenitors also exhibit repressed Ihh signaling. Due to the inaccessibility of fracture callus tissue from diabetic patients, we obtained freshly dissected femoral and knee specimens from osteoarthritic diabetic patients undergoing total joint arthroplasty. These tissues possessed large regions of cartilage degeneration that we used to investigate reparative signaling in isolated skeletogenic cells purified by FACS (FIG. 6A). We found that approximately 30% of the non-hematopoietic (CD45 negative) and non-endothelial (CD31 and Tie2 negative) fraction of these cells express CD146, a marker that has been used previously to describe a population of human skeletal stem and progenitor cells (FIG. 6B). Gene expression analysis confirmed that both Ihh and Gli1 are down-regulated in diabetic patient samples relative to non-diabetic patients, consistent with our findings in mice (FIG. 6C-D).

Figure 7A:
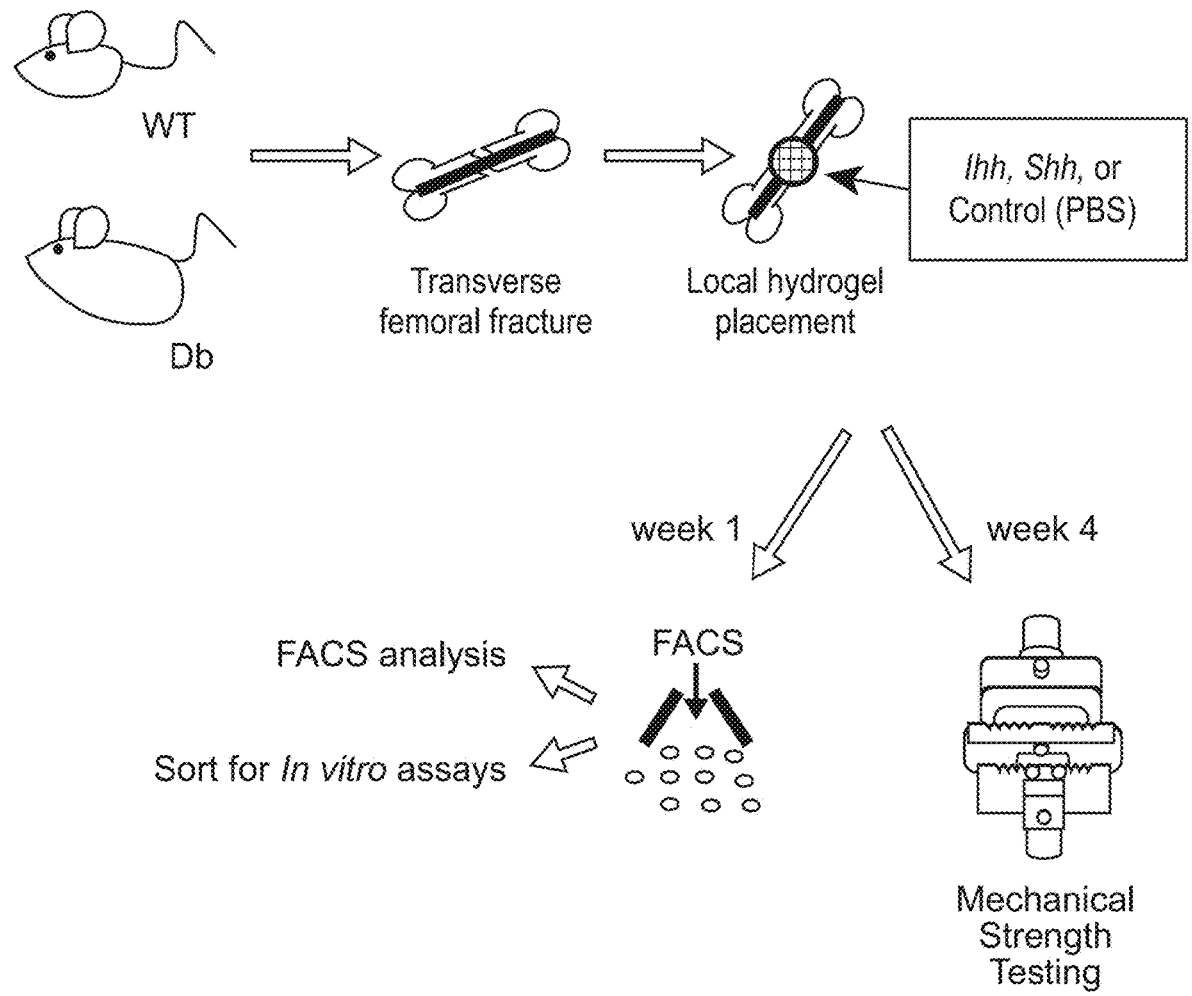
FIG. 7A-7G. Local delivery of Ihh restores mSSC's functional response to injury.
Figure 7B:
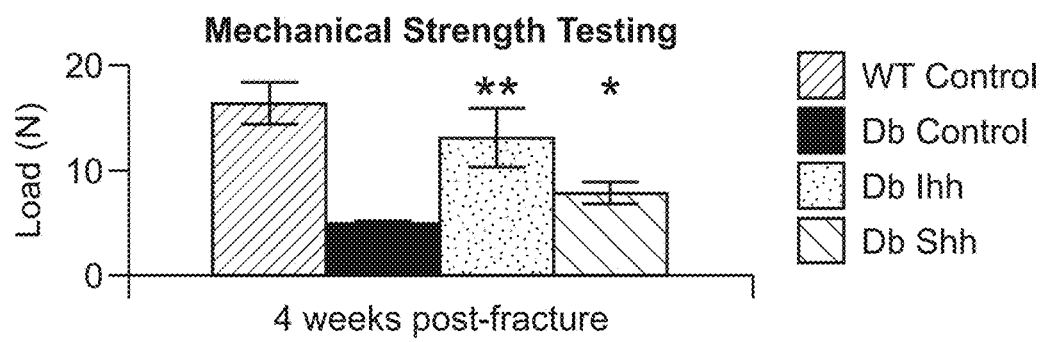
Figure 7C:
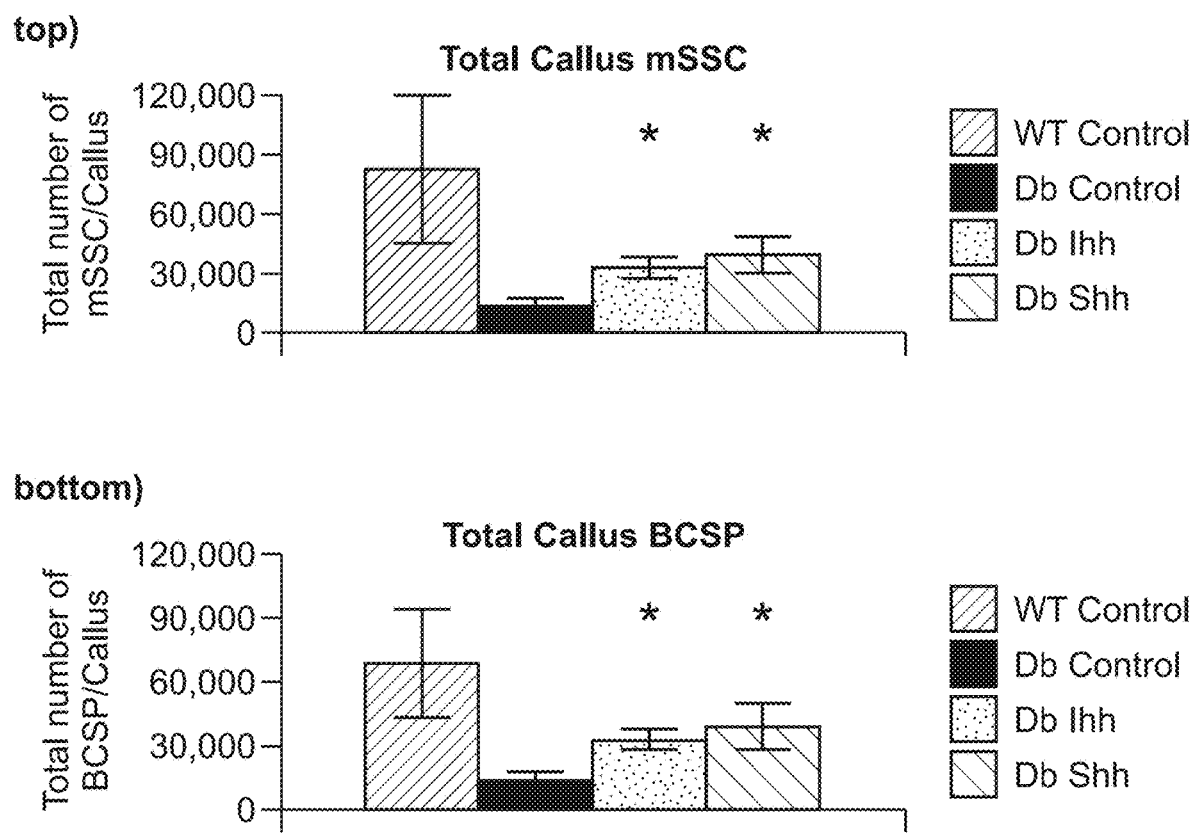
Figure 7D:
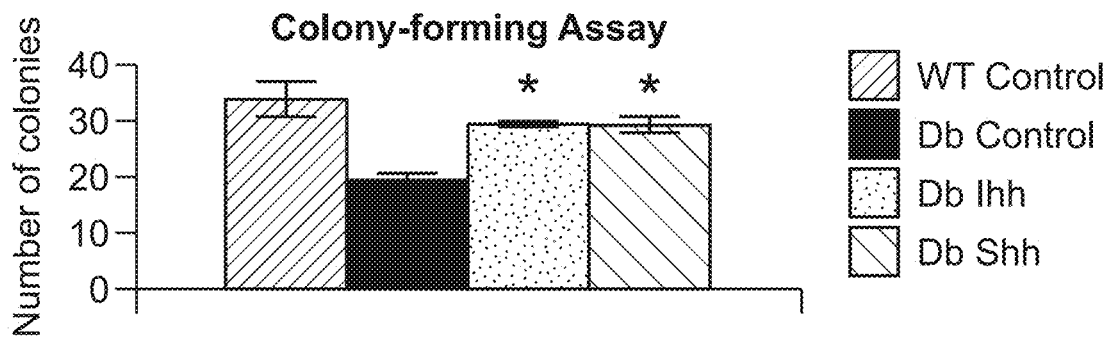

Local delivery of Indian hedgehog rescues diabetic fracture healing. We then assessed if modulating local Hh expression could improve diabetic fracture repair by applying degradable poly(ethylene glycol) hydrogels coated with recombinant Ihh, Sonic hedgehog (Shh), or PBS control to the defect sites of $db_{LR}$ or WT mice immediately after fracture creation (FIG. 7A). Notably, MST analyses of healing femora harvested at post-fracture week 4 revealed that Ihh- and Shh-treated $db_{LR}$ femora were significantly stronger than PBS treated controls (FIG. 7B). To determine if this improvement was associated with changes in mSSC or BCSP activity, we profiled the cellular composition of Hh-treated versus untreated post-fracture day 7 calluses using FACS and found that the absolute numbers of both mSSCs and BCSPs increased significantly in Hh-treated calluses (FIG. 7C). We also found that FACS sorted mSSCs isolated from Hh-treated calluses of $db_{LR}$ mice formed significantly more colonies in vitro than mSSCs from $db_{LR}$ controls. These results indicate that local delivery of Hh to the skeletal stem cell niche rescued $db_{LR}$ mSSC clonal activity, emphasizing the importance of Hh signaling in mSSC activity (FIG. 7D).

Figure 7E:
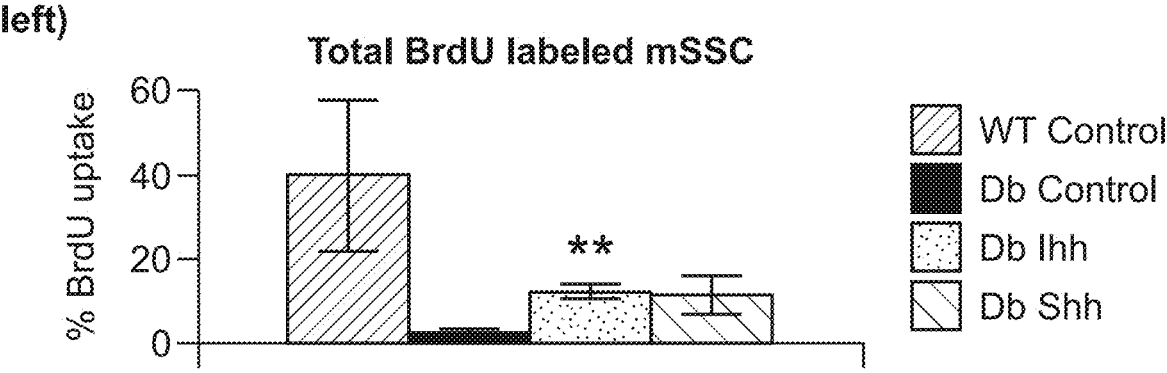
Figure 7E:
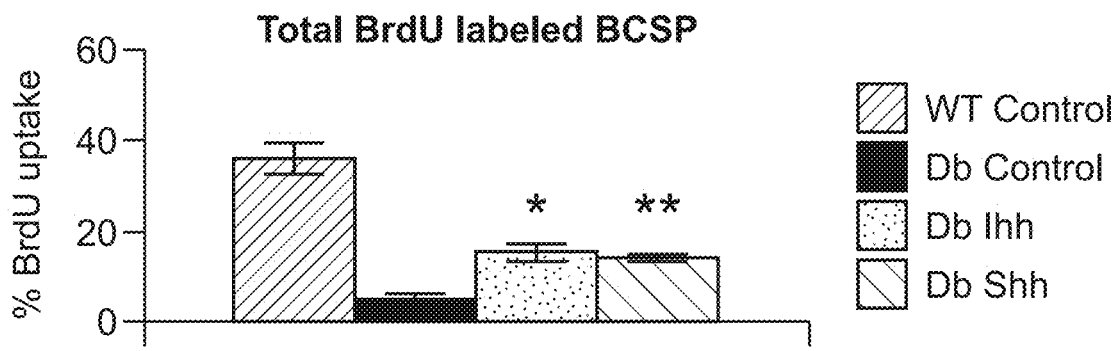
Figure 7F:
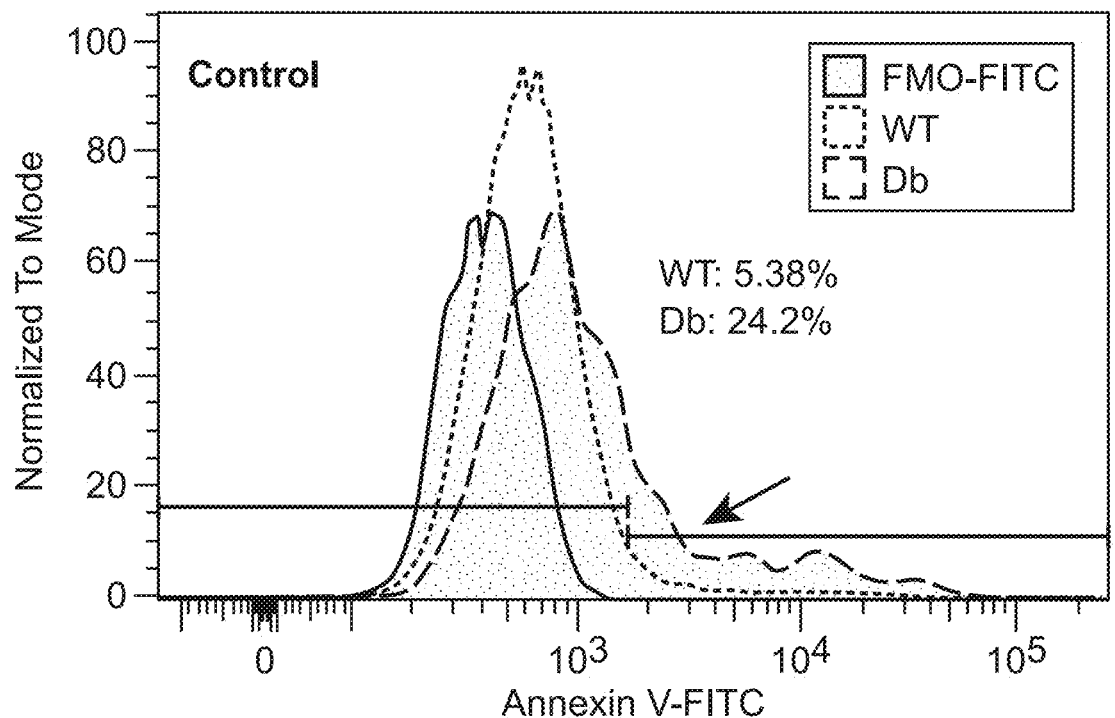
Figure 7F:
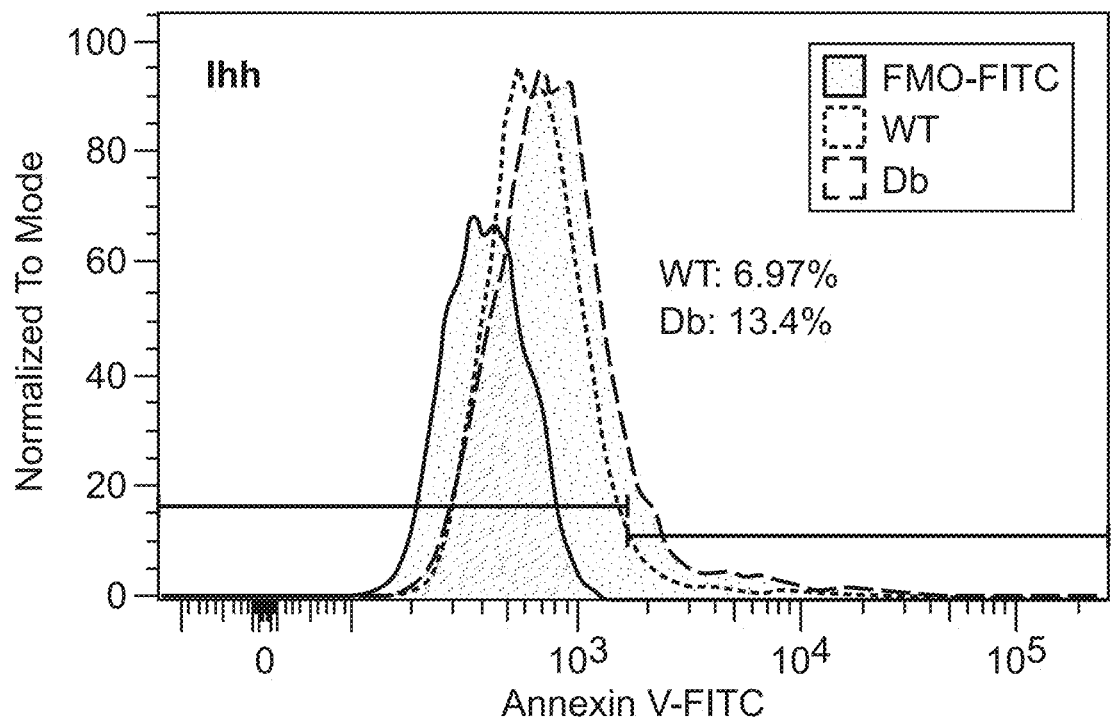
Figure 7G:
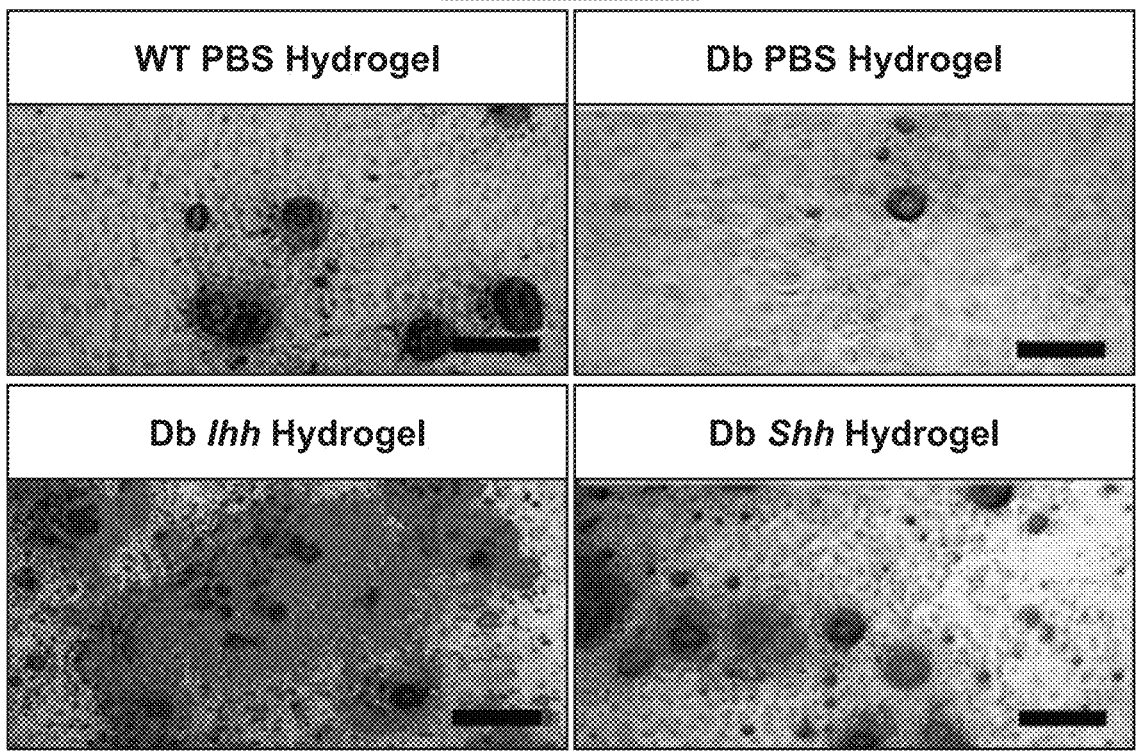
Figure 7G:
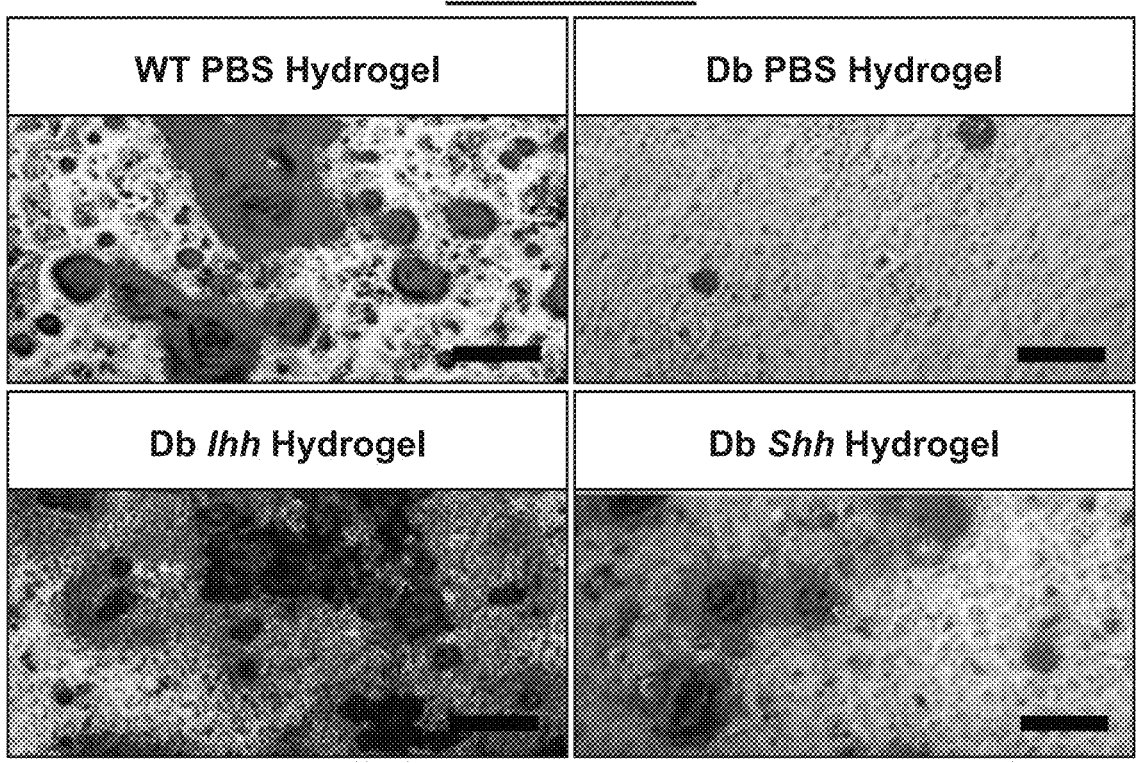
Figure 8:
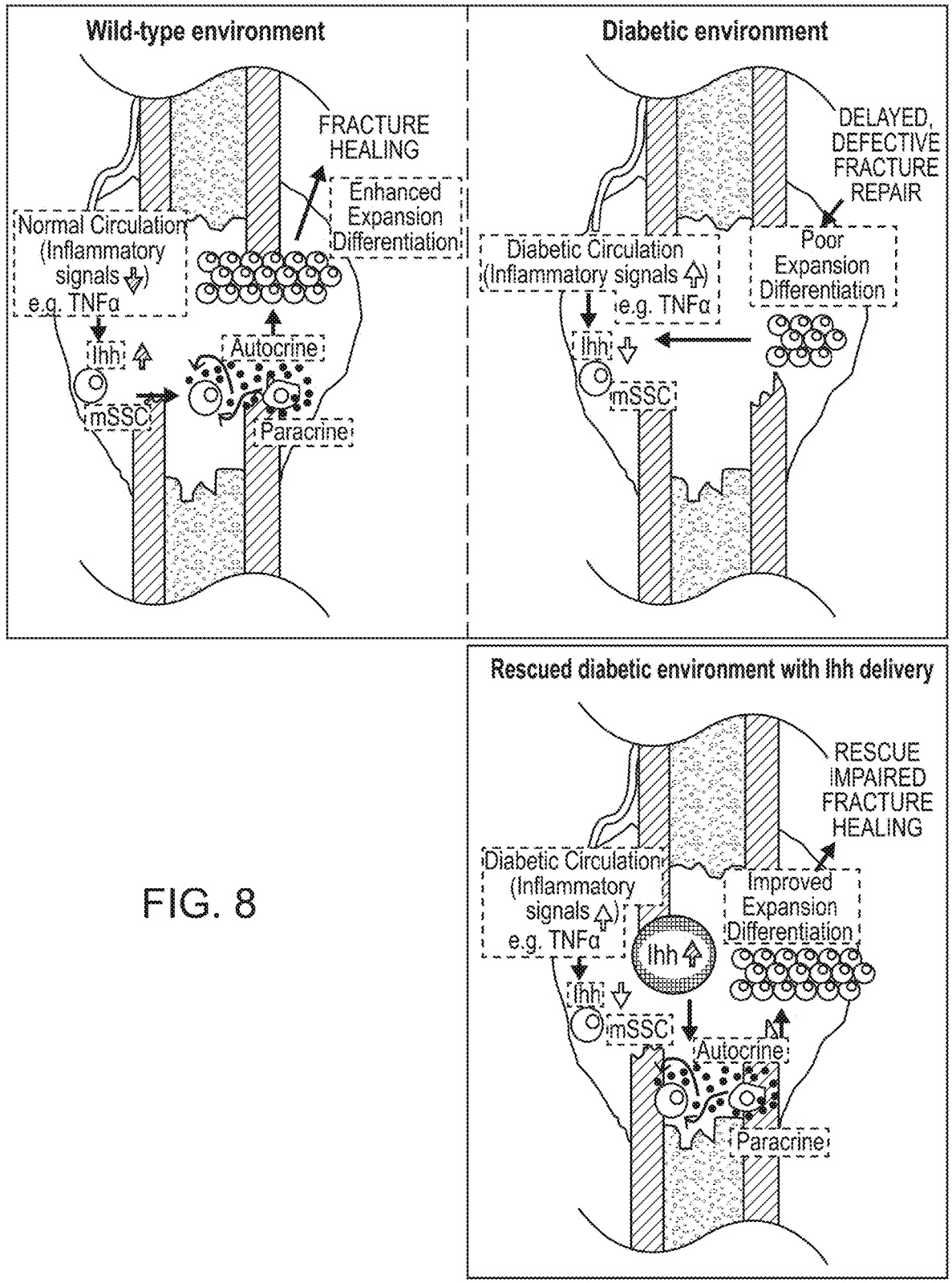
FIG. 8. Schematic showing the cellular and molecular mechanisms underlying impaired diabetic skeletal repair. A. In non-diabetic conditions (left box), normal Hh-mediated crosstalk between mSSCs and BCSPs in skeletal niches coordinates an effective injury response. In diabetic conditions (right box), high serum levels of TNFα disrupt skeletal niche signaling, leading to impaired fracture repair.
Figure 13A:
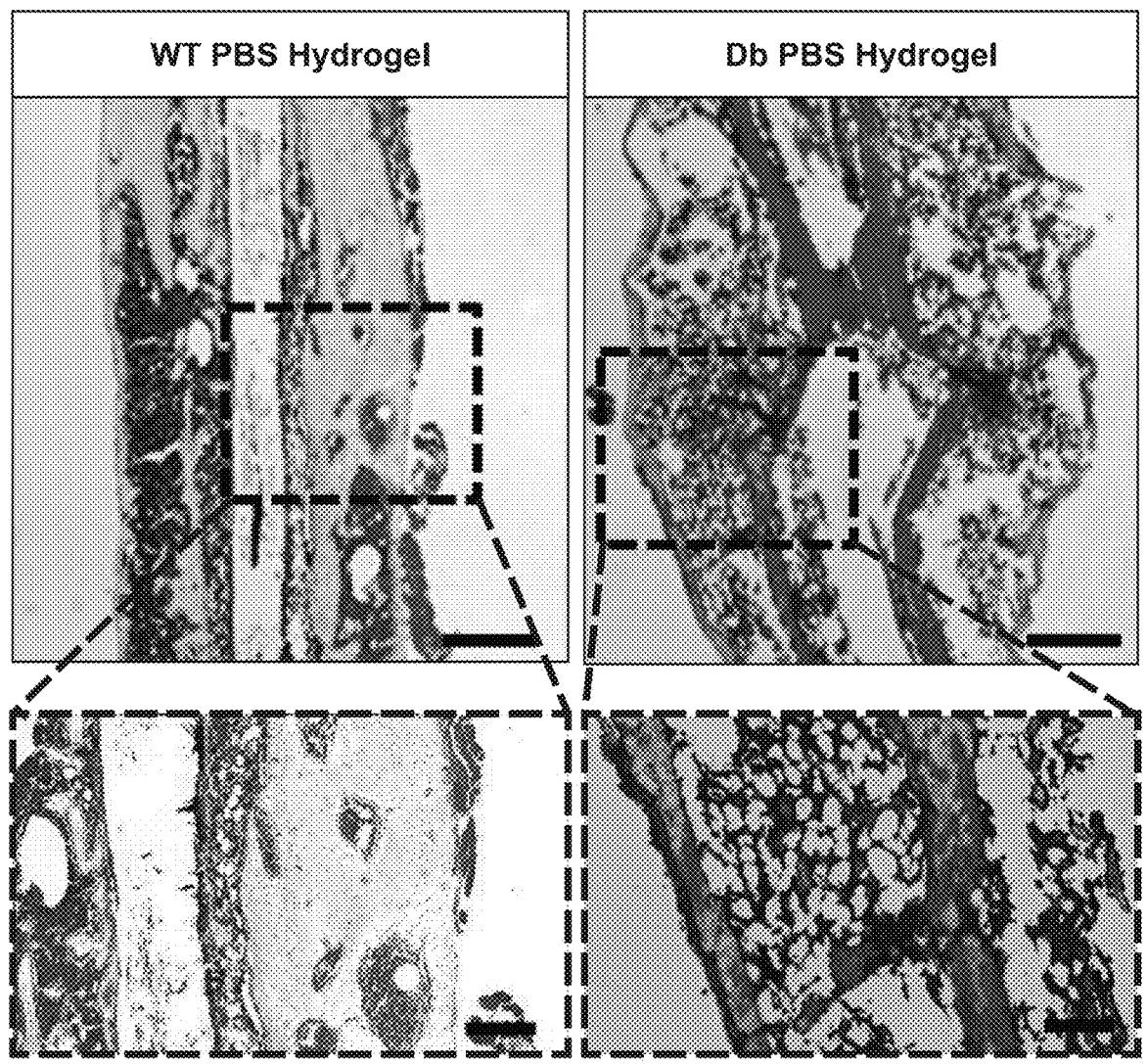
FIG. 13A-13B. Local delivery of Ihh restores impaired bone healing in db mice.
Figure 13A:
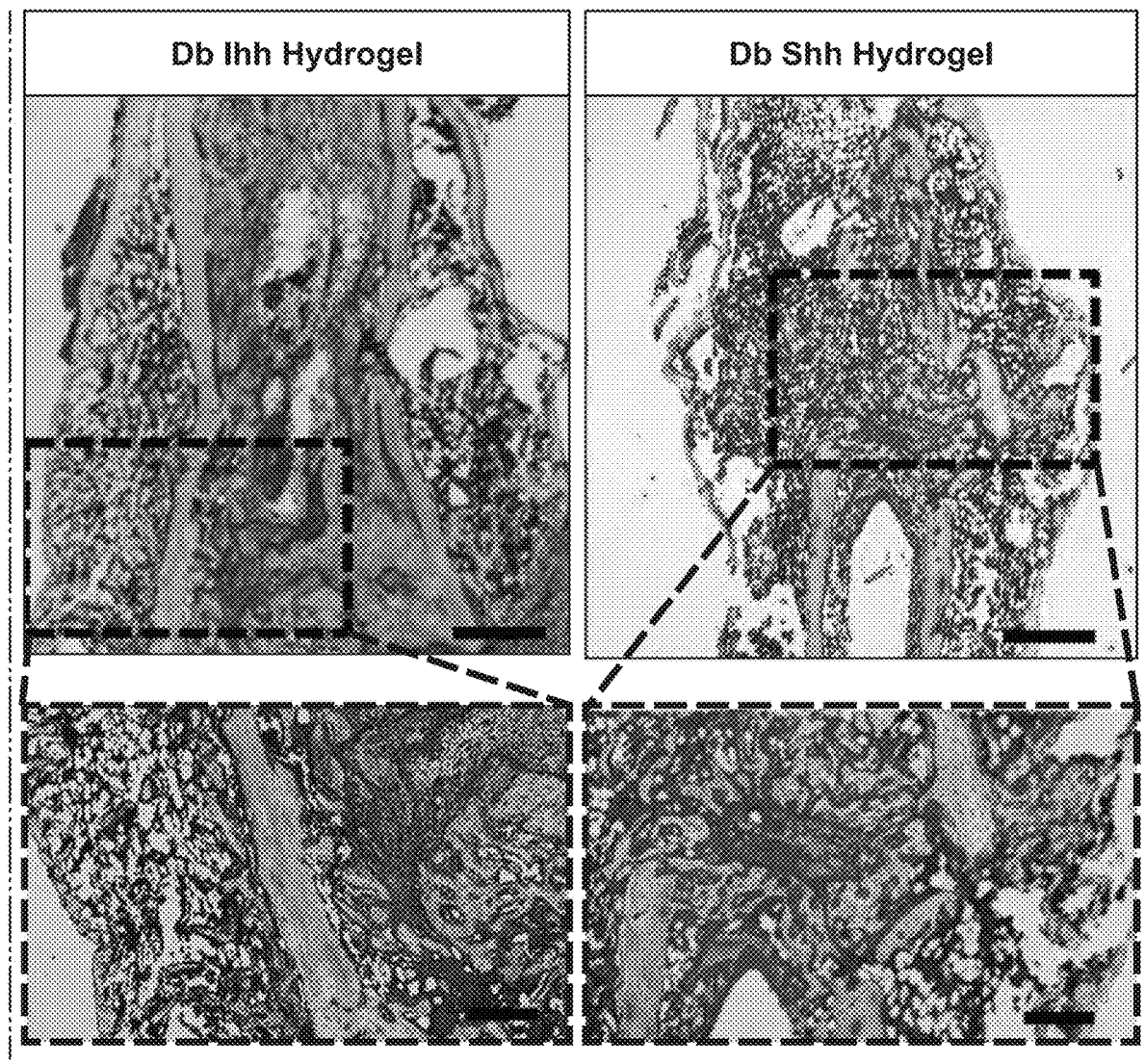
Figure 13B:
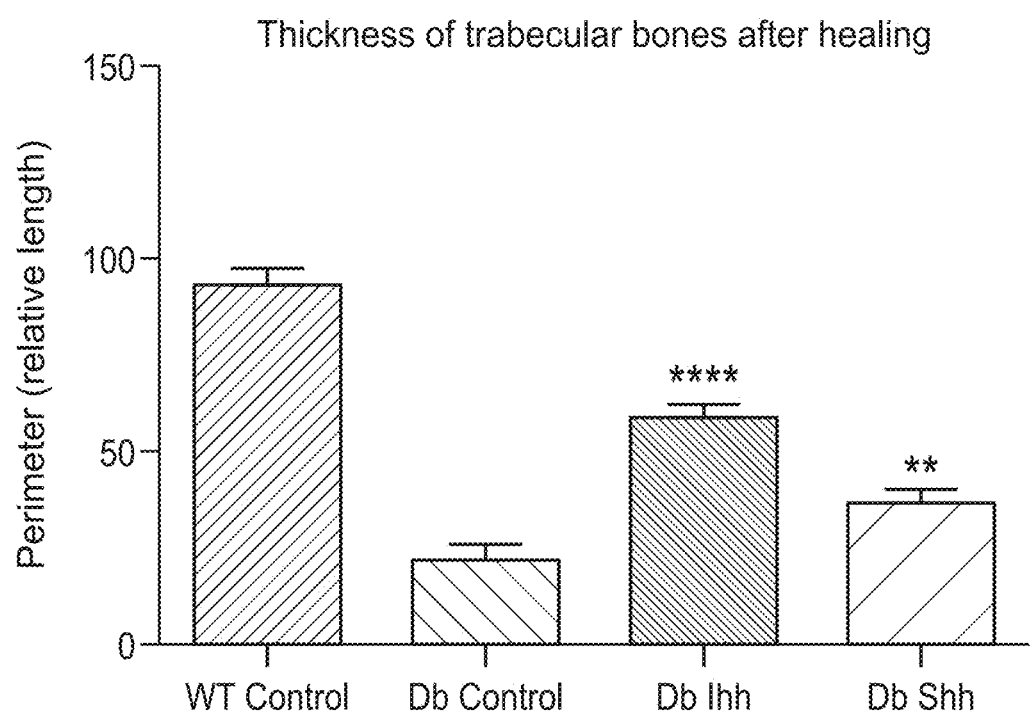
Figure 14A:
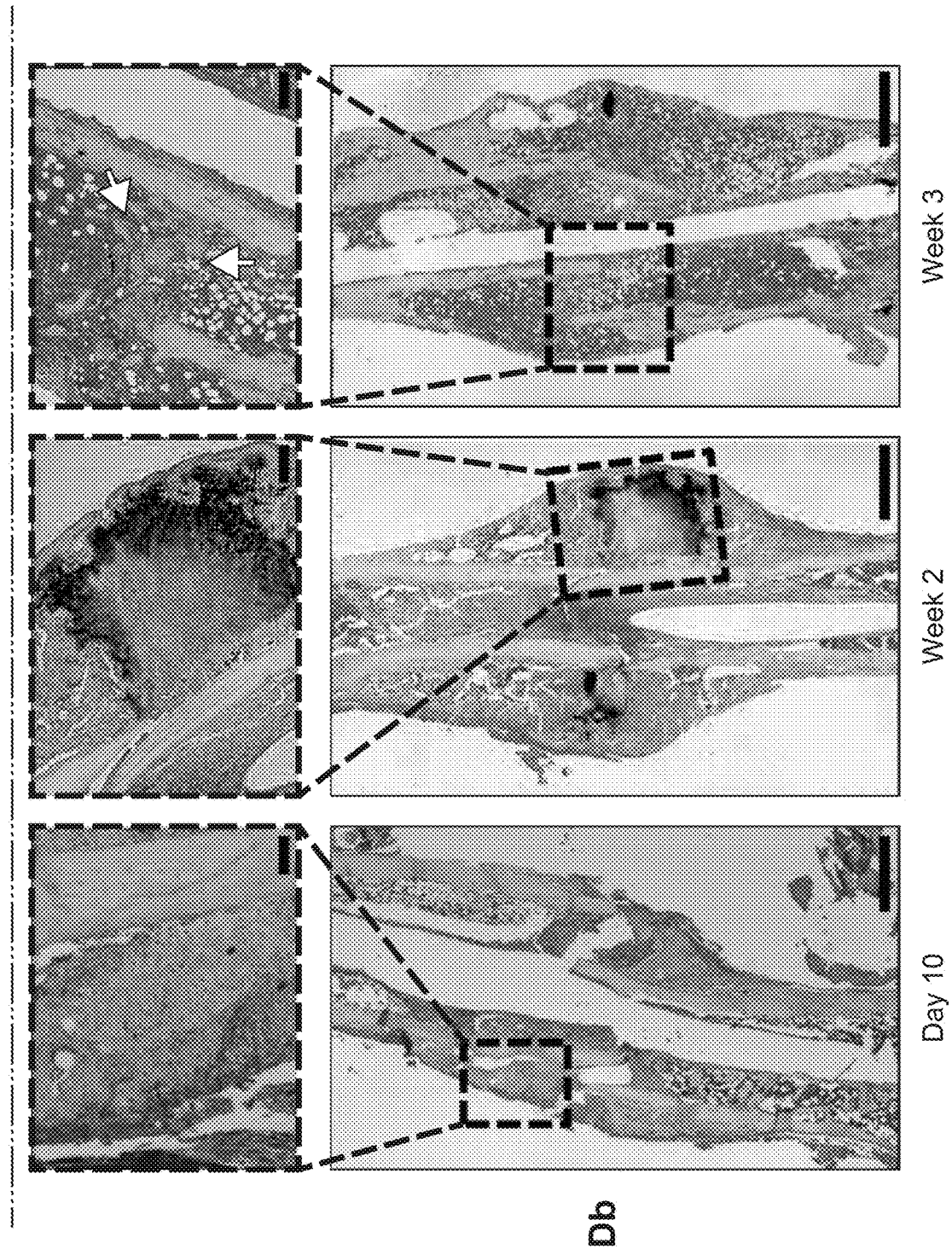
FIG. 14A-14E. Bone regeneration is impaired in db versus WT mice but osteoclastic activity is not notably affected.
Figure 14B:
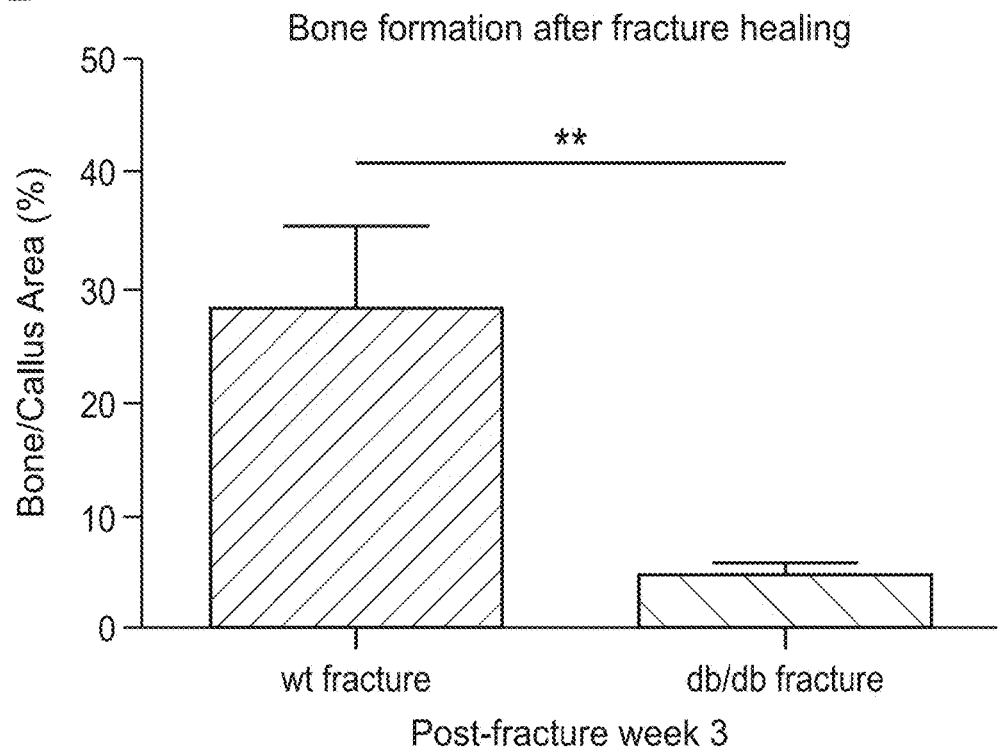
Figure 14C:
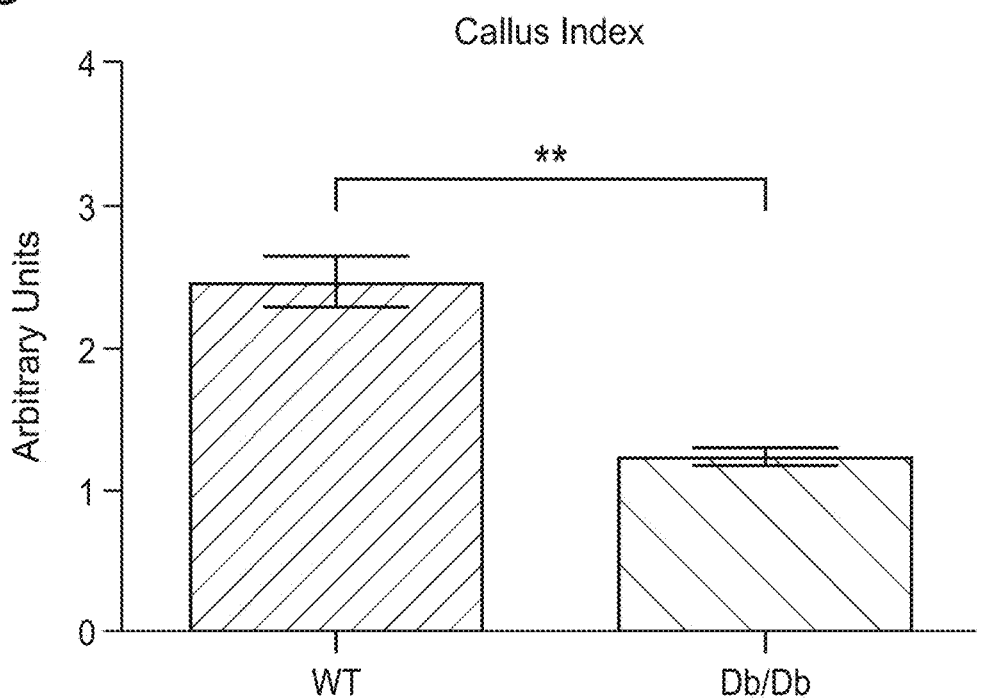
Figure 14D:
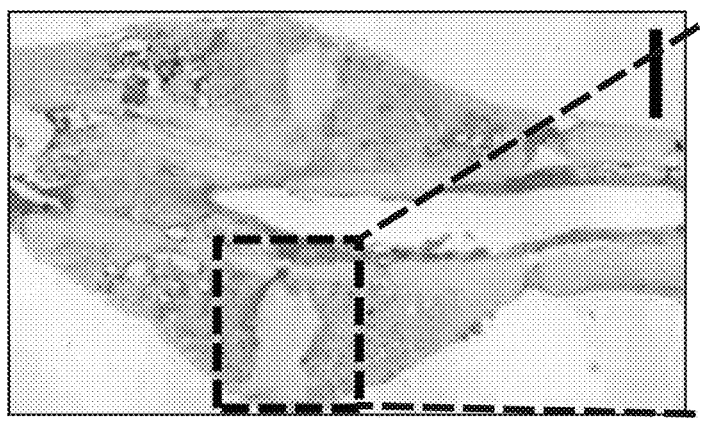
Figure 14D:
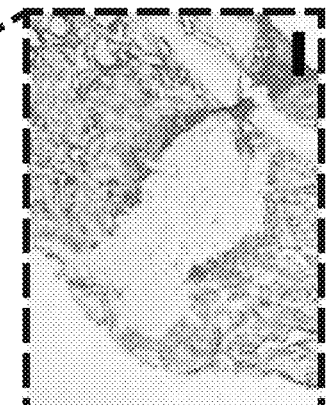
Figure 14D:
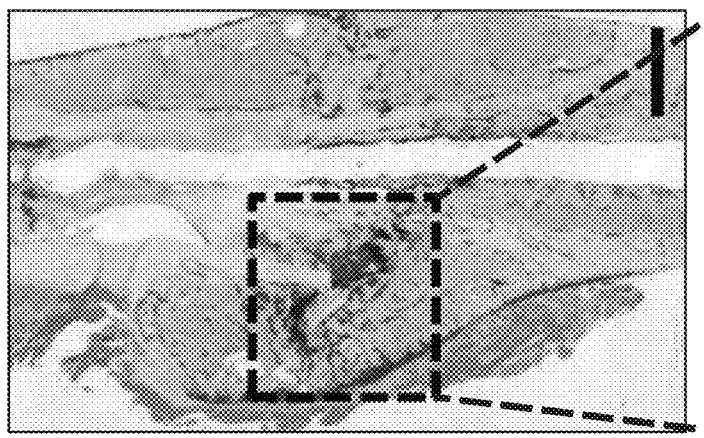
Figure 14D:
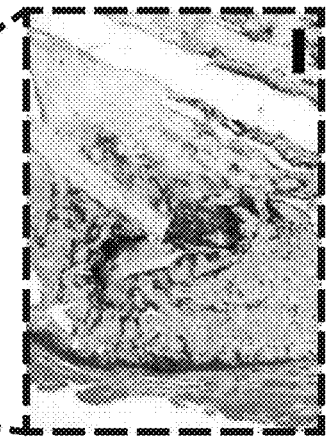
Figure 14D:
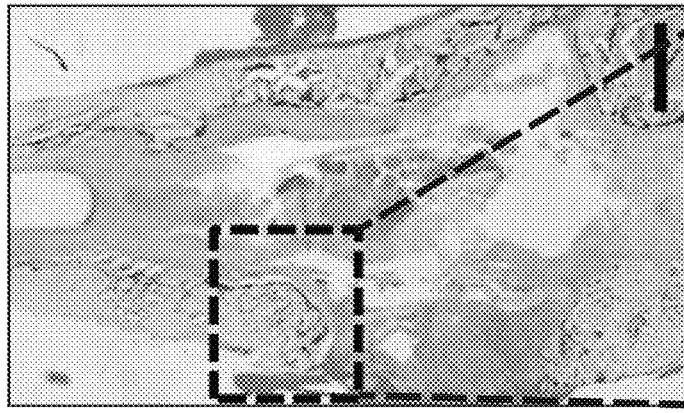
Figure 14D:
Figure 14D:
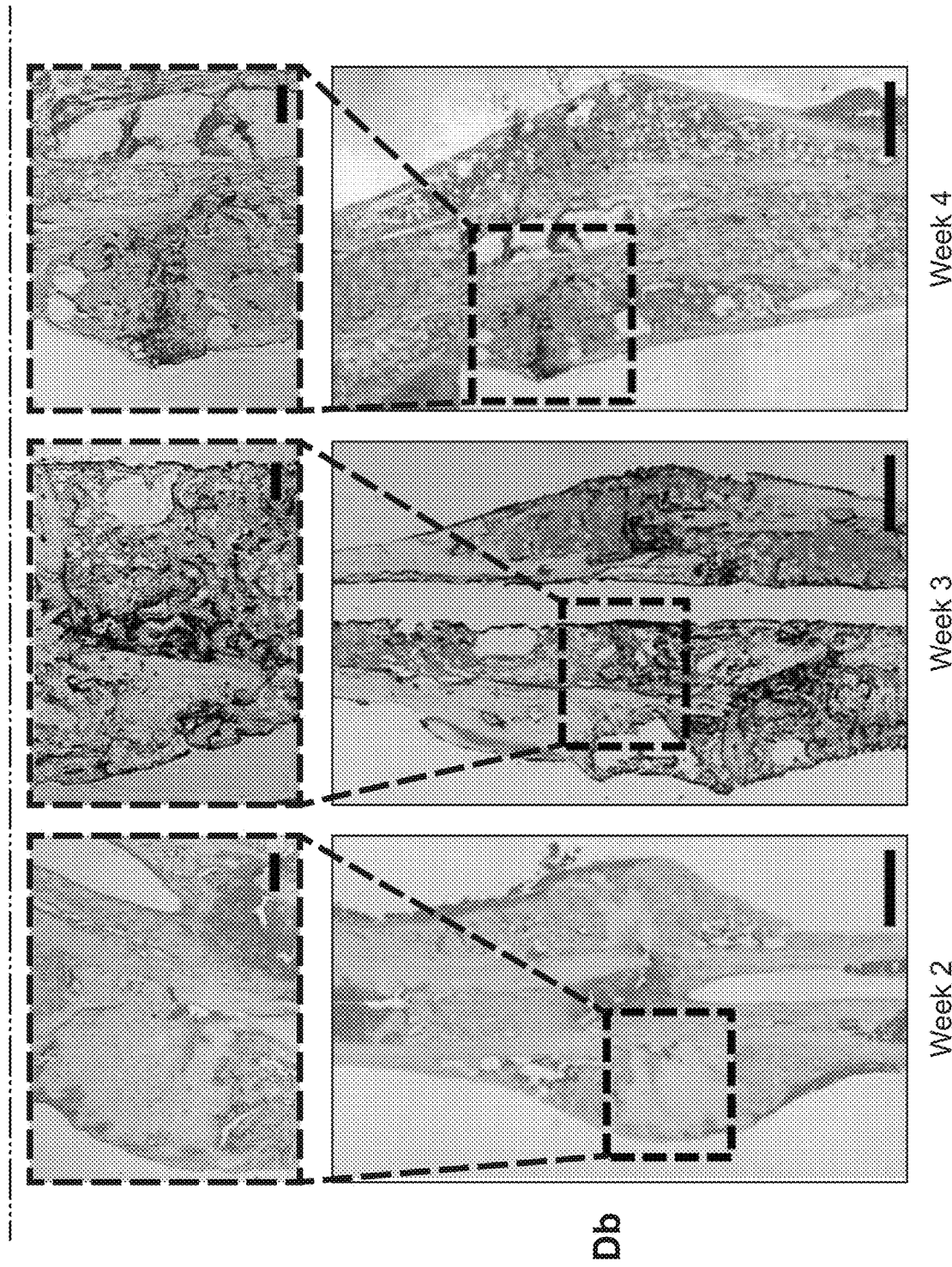
Figure 14E:
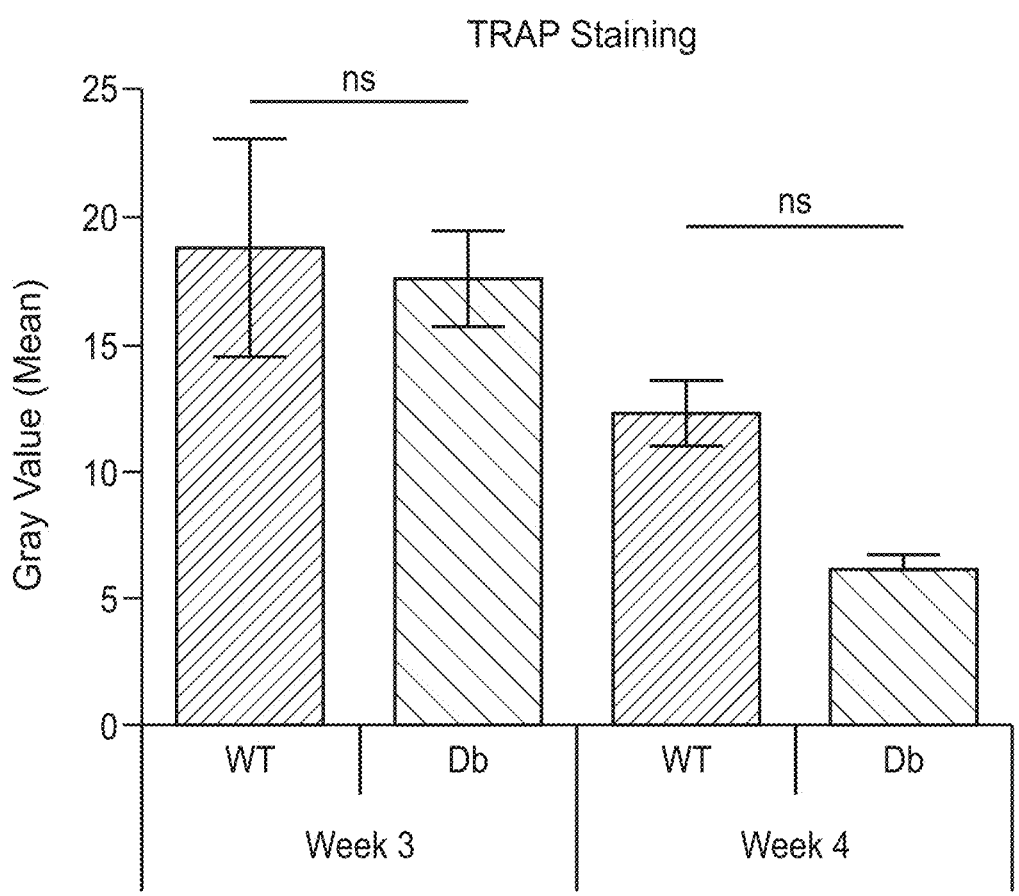
Figure 15A:
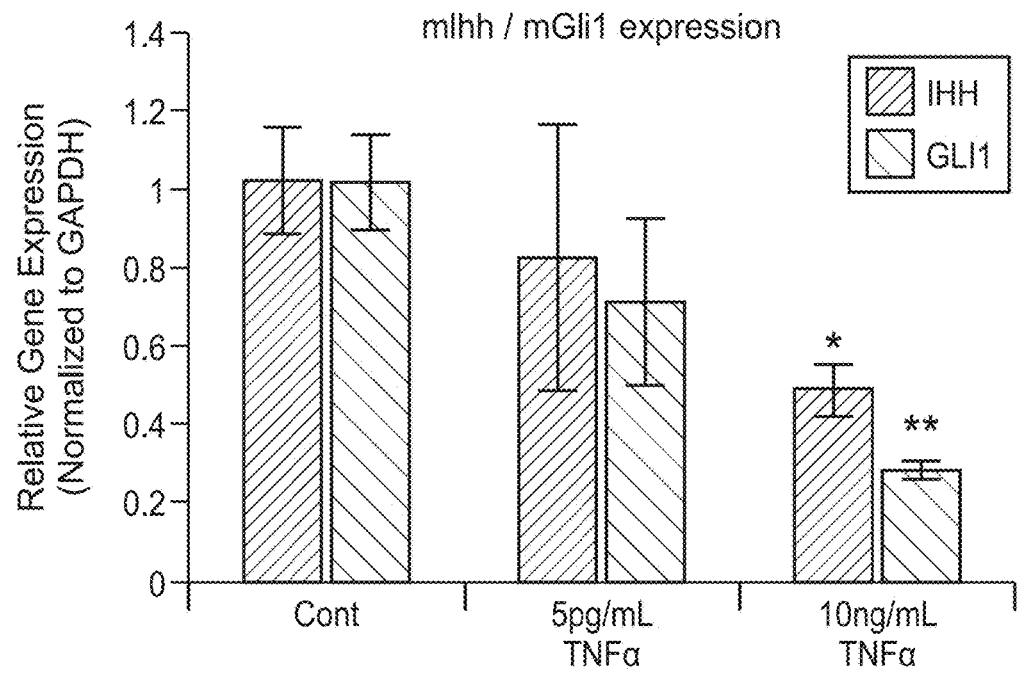
FIG. 15A-15D. Neutralization of TNFα signaling in db serum restores Ihh expression in co-cultured mSSC.
Figure 15B:
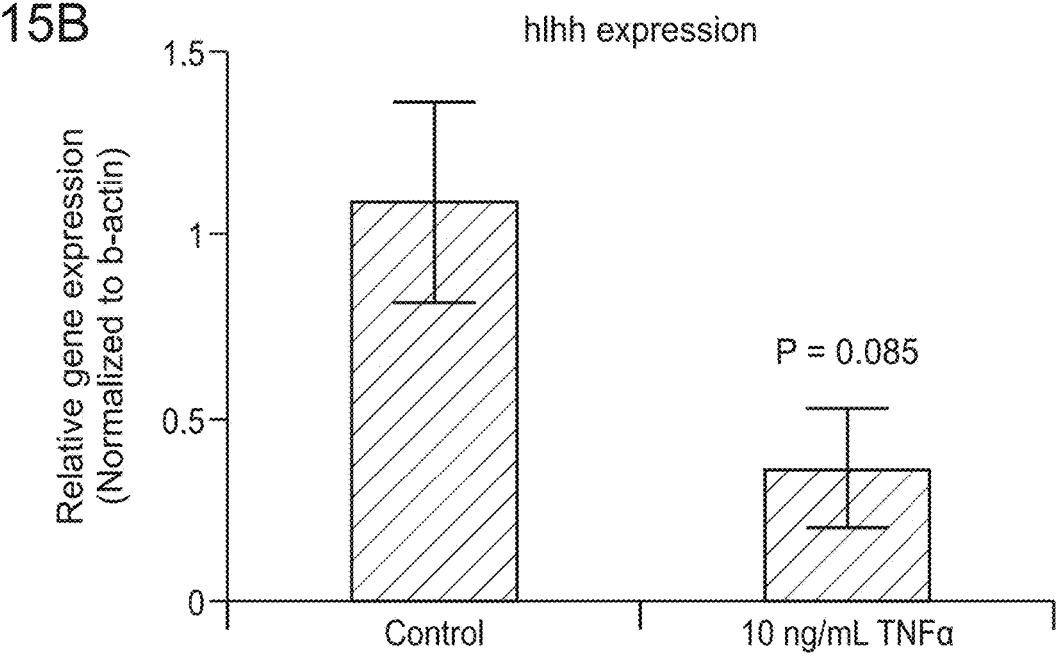
Figure 15C:
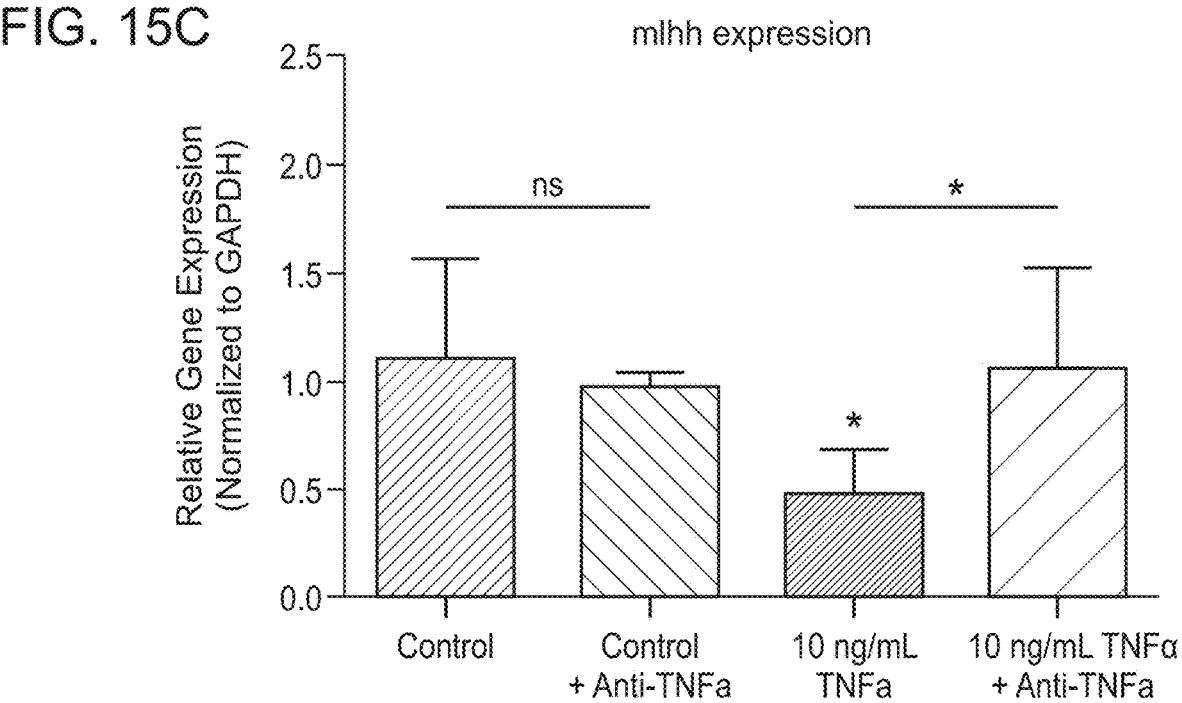
Figure 15D:
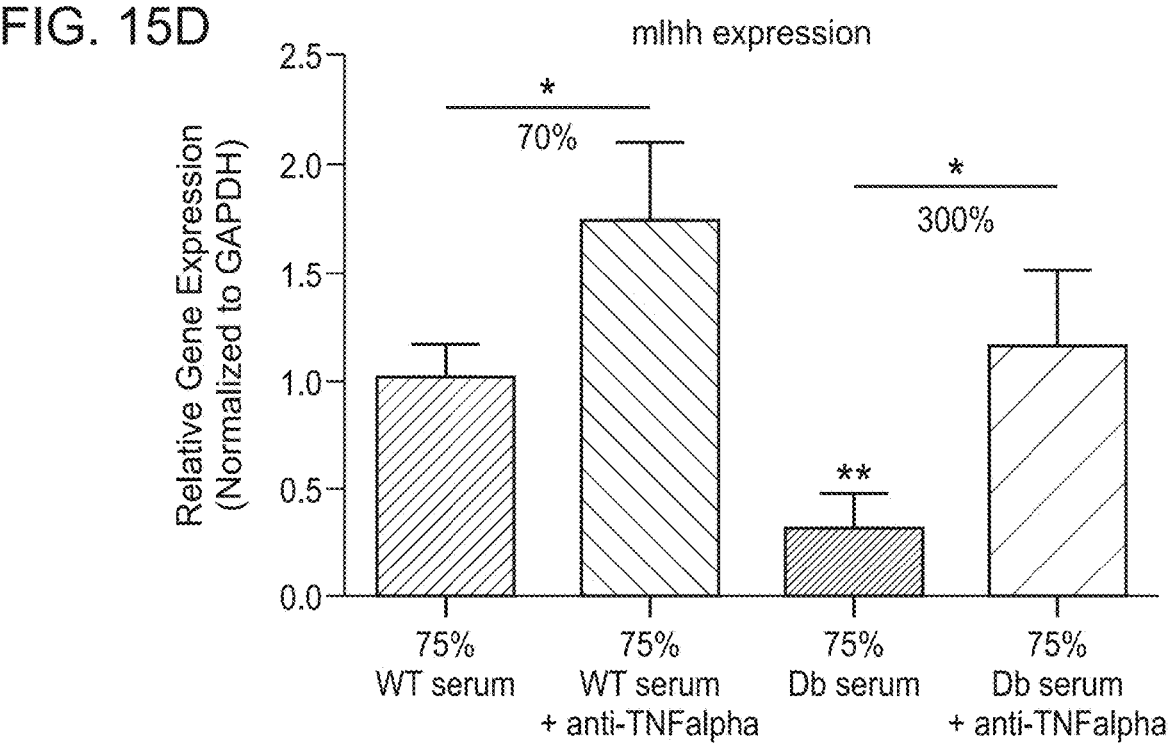

To gain insight into how exogenous Hh treatment stimulated mSSC and BCSP activity, we assessed the proliferative and apoptotic activity of each population after treatment. We found that BrdU uptake was significantly higher in mSSCs and BCSPs in post-fracture day 3 calluses following Hh treatment in $db_{LR}$ mice (FIG. 7E). We also found that Hh treatment reduced the apoptotic activity of $db_{LR}$ mSSCs relative to controls, as assessed by annexin V expression. By comparison, it did not affect the apoptotic activity of WT mSSCs (FIG. 7F). Together, these results suggest Hh treatment improves the mSSC and BCSP injury response in part by enhancing cellular expansion and survival in calluses of $db_{LR}$ mice. We then investigated if Hh treatment could enhance mSSC- and BCSP-mediated osteogenesis. Both mSSCs and BCSPs from Hh-treated, post-fracture day 7 calluses were more osteogenic than those from $db_{LR}$ controls, as assessed in vitro by alizarin red staining (FIG. 7G). These results are supported by histomorphometric analyses that show significantly enhanced osteogenesis in $db_{LR}$ mice (FIG. 13). Together, these findings demonstrate that targeted molecular therapy corrects specific skeletal niche defects caused by systemic diabetic disease, resulting in the restoration of mSSC dependent repair in $db_{LR}$ mice (FIG. 8).

Here, we describe a new mode of therapy that treats the altered reparative function of local stem and progenitor cells in db mice. In systemic diseases with multiple complications, it is challenging to characterize the mechanisms of tissue-specific dysfunction. Our approach determined cell-intrinsic versus cell-extrinsic control of skeletogenesis based on the recent characterization of the mSSC and its downstream progenitors that produce skeletal tissue.

Under normal conditions, mSSCs and BCSPs facilitate rapid healing. However, in db mice, significantly reduced injury expansions of mSSCs and BCSPs suppressed osteogenesis and impaired healing. Several groups have reported that exposure to a young circulation rejuvenates muscle, heart, brain, and skeletal tissue and that exposure to a nondiabetic circulation improves diabetic cutaneous wound healing. However, we found that exposure to a non-diabetic circulation did not restore diabetic bone healing. As a result, we centered our investigation on the mSSC and its downstream progenitors.

Deviations in normal mSSC activity could be cell-intrinsic, or they could arise from alterations to the external regulatory niche environment. Because heterotopic transplantation of mSSCs or BCSPs from db and WT calluses revealed that the intrinsic skeletogenic activity of each cell population did not differ, we hypothesized that cell-extrinsic abnormalities in skeletal niche signaling impaired diabetic healing. Heterotopic transplantation of WT mSSCs and BCSPs into db or WT mice supported this hypothesis because the size of grafts produced in db mice was significantly reduced. Factors known to be associated with mSSC niche signaling include bone morphogenic protein (BMP), WNT, hedgehog proteins (Hh), and transforming growth factor-β.

We examined these factors within the mSSC niche of db mice to identify abnormalities that could impair healing and ultimately lead to effective intervention. Our laboratory previously investigated paracrine- and autocrine-mediated control of normal mSSC activity using gene expression analysis and single-cell RNA-sequencing. When we applied the same analysis to db mSSCs, we found that although many skeletogenic signaling pathways were unchanged, Hh signaling was altered in db mSSCs after fracture. Ihh signaling is essential for embryonic skeletal formation and endochondral ossification, and it has also been implicated in regulation of cartilage development. Our results indicate that hedgehog signaling is also necessary for skeletal regeneration in mice and suggest that decreased Ihh expression in db calluses is likely a major factor in the molecular etiology of poor fracture healing in DM.

In addition to skeletal stem and progenitors in mice, we observed repressed Ihh signaling in human skeletal progenitors isolated from femoral head and knee specimens of diabetic patients (FIG. 6). These results indicate that Hh signaling and its importance to postnatal skeletal repair appear to be conserved between mouse and humans. We also found that elevated levels of TNFα in db mice can directly suppress Ihh expression in mSSCs and BCSPs. TNFα is expressed by a wide variety of tissues, including macrophages, T cells, and adipose tissue. Although it plays a key role in mediating the inflammatory response against microbial infections, TNFα has also been implicated in autoimmune disease and diabetes. In humans, elevated levels of TNFα are frequently detected in diabetic patients and have been shown to disrupt fracture healing.

The findings presented herein demonstrate that diminished Ihh signaling plays a mechanistic role in the chronic inflammatory state associated with DM. Due to the risk of anti-TNFα antibody therapy leading to increased adiposity as well as reports of impaired fracture repair in the absence of TNFα, we directly modulated skeletal niche signaling by delivering recombinant Ihh or Shh to the local fracture site using a slow release hydrogel. We found that both Ihh and Shh restored fracture repair in db mice, in part by enhancing mSSC expansion, survival, and osteogenic potential in db calluses. Because we observed that skeletal progenitors in bone and cartilage tissues isolated from DM patients undergoing total joint arthroplasty also demonstrate down-regulation of Ihh and Gli1 expression, local administration of recombinant Ihh or small molecule hedgehog agonists may also accelerate fracture repair in these patients.

Graves et al. reported that streptozotocin-induced Type 1 DM led to increased osteoclast activity during fracture healing. However, in a model of Type 2 DM, they observed that osteoclastogenesis was decreased. These findings oppose our observation that osteoclast activity was not significantly changed in vivo in models of Type 2 DM, therefore suggesting that additional factors could influence the activity of the regenerative niche during skeletal healing.

In summary, we devised a clinically relevant strategy for reversing complex, tissue-specific pathologies associated with metabolic disease. We demonstrate that the local application of two factors, Ihh and Shh, rescues diabetic bone healing by stimulating mSSC injury expansion. Thus, by determining how DM affects the mSSC and its supporting niche, we show how molecular therapies can be identified and used to treat metabolic disease directly at the stem cell level. These findings are consistent for multiple models of DM. Hh-mediated molecular therapies that directly target stem cells in human diabetic patients can be therapeutic.

Materials and Methods

Study Design. The objective of this study was to understand the cellular and molecular mechanisms underlying impaired bone healing in diabetic mice. Multiple mouse models of diabetes were used. For all experiments, the number of samples analyzed is outlined in the figure legends and were performed in triplicate. No outliers have been excluded from our analysis. Animals used for the hedgehog-rescue experiments were randomized with animals receiving hydrogel alone, hydrogel with Ihh, or hydrogel with Shh.

Femoral fractures. Ten-week old mice were anesthetized with aerosolized isoflurane. Analgesia was administered and the surgical site was prepared prior to skin incision. A medial parapatellar incision was created. The patella was dislocated laterally to expose the femoral condyles. The medullary cavity was reamed using a 25 to 23 G×⅝-inch regular bevel needle (BD) prior to insertion of an intramedullary pin of equal diameter into the medullary cavity. A transverse, middiaphyseal fracture was made using scissors. The pin remained in situ to provide relative stability during healing. The patella was relocated, muscles were reapproximated, and the skin was closed using a 6/0 nylon suture. Animals were radiographed to verify fracture alignment and assess fracture fixation. Animals with fracture displacement were excluded. Pin diameter was adjusted according to femoral cavity lumen diameter to minimize migration.

Isolation of skeletal progenitor cells. Uninjured femora and fractured femora were harvested at post-fracture days 3, 7, 10, 14, 21, and 28. Fracture calluses were dissected using microscopy. Tissues were crushed with mortar and pestle in collagenase buffer (2.2 mg/ml collagenase, DNase, 1000×1 M CaCl2, 100×p188, 50×1 M Hepes, m199 solvent), and heated to 37° C. for 10 min to activate collagenase. Each sample underwent 3 serial digestions at 37° C. for 25 minutes under gentle agitation. Dissociated cells were filtered through a 40 μm nylon mesh and washed in FACS buffer (2% fetal bovine serum in PBS). Each sample was pelleted at 200 g at 4° C. and resuspended in FACS buffer. Then, each sample was layered onto a histopaque gradient prior to centrifugation at 1400 rpm for 15 minutes at room temperature with zero acceleration. The cloudy interphase was aspirated, washed with FACS buffer, and centrifuged. The cells were stained with fluorochrome-conjugated antibodies against CD45, Ter119, Tie2, αv-integrin, Ly 51, CD105, Thy 1.1, and Thy 1.2 for purification by flow cytometry. Cells were sorted twice (once on "yield," then on "purity") to increase purity (BD FACS Aria).

Isolation of human bone progenitors. Femoral heads were obtained from diabetic and non-diabetic patients undergoing total joint arthroplasty. Cells from areas of cartilage degeneration were processed as described in Isolation of Skeletal Progenitor Cells. Cells were stained with fluorochrome-conjugated antibodies against CD45, CD235, and CD146 for purification by flow cytometry. Cells were sorted twice (once on "yield," then on "purity") (BD FACS Aria). Human skeletal progenitors were defined as CD45(−)CD235(−)CD146(+/−). Statistical analysis All analyses were performed using GraphPad Prism. Data were analyzed using two-tailed Student's t-test and/or one-way ANOVA and post hoc Tukey correction. Statistical significance was assigned for $p \leq 0.05$. All experiments were done in triplicate.

Animals. Mice were maintained at the Stanford University Comparative Medicine Pavilion and Research Animal Facility in accordance with guidelines set by the Stanford University Animal Care and Use Committee (APLAC-28330, APLAC-27683, APLAC-9999) and the Institutional Animal Care and Use Committee. Animals were housed in ventilated cages and were given food and water ad libitum. C57Bl/6 (00664), $Lepr_{db}$ (00697), and diet-induced obesity ($db_{DIO}$, C57Bl/6) strains were obtained from Jackson Laboratories. Streptozotocin-induced diabetes ($db_{STZ}$) was created in C57Bl/6 mice according to a standard protocol of streptozotocin injections provided by Jackson Laboratories. Homozygous, GFP-expressing C57Bl/6 and C57Bl/6/Rag2/γ(c)KO (non-diabetic immunodeficient) mice were generated in the Weissman laboratory.

Mechanical Strength Testing (MST). MST was performed using a delaminator run by R.H. Dauskardt laboratory at Stanford University. Femora were harvested at post-fracture week 4, and the overlying soft tissues and intramedullary pins were removed. MST analysis was conducted within 24 hours of the tissue harvest, so no additional preparation was done. Samples were preloaded to 1 Newton (N) and underwent a three-point bend test at a compression rate of 1 micron/second. The maximum load (N) to fracture was recorded (FIG. 9).

Hydrogel fabrication and placement. Eight-arm poly(ethylene glycol) (PEG) monomers with end groups of norbornene (MW 10 kDa) or mercaptoacetic ester (MW 10 kDa) were dissolved in phosphate-buffered saline (PBS) at a concentration of 20% (w/v). Photoinitiator lithium phenyl-2,4,6-trimethylbenzoylphosphinate was then added to each solution to make a concentration of 0.05% (w/v). The two polymer solutions were mixed at a 1:1 volume ratio to obtain a hydrogel precursor solution. Recombinant mouse growth factors, Ihh (R&D Systems: 1705-HH-025), Shh (R&D Systems: 464-SH-025) and thrombomodulin (R&D Systems: 3894-PA-010) were added to the precursor solution at concentrations of 2.5 mg/mL, 2.5 mg/mL, and 0.5 mg/mL, respectively. Solutions were exposed to UV (365 nm, 4 mW/cm$^2$) for 5 min in the mold with a volume of 4 μL each (thrombomodulin, 6 uL) to obtain growth factor-loaded hydrogels, with a loading amount of 5 μg/gel, 5 μg/gel, and 3 μg/gel for Ihh, Shh and thrombomodulin, respectively. PBS-loaded hydrogels served as controls.

For in vivo treatment, hydrogels were placed anteromedially on the defect and left in place until tissue harvest. In vitro kinetic assays were performed to show slow-release morphogen delivery. Each hydrogel was maintained in 200 μl of PBS in a 96-well plate at 37° C. The PBS solution was collected every 1-3 days for 4 weeks, stored at −80° C., and analyzed for morphogen concentration using a commercially available ELISA kit (R&D Systems).

Intracellular 5-bromo-2'-deoxyuridine (BrdU) proliferation assay. The intracellular FACS protocol was run as per the manufacturer's instructions using the FITC BrdU Flow Kit (BD Biosciences). Briefly, BrdU was administered by intraperitoneal injection 12 hours prior to harvest on post-fracture day 3 or 7. Cells were processed as described above and were permeabilized, subjected to DNase, stained with BrdU antibody, and analyzed using FACS.

Blood glucose monitoring. Circulating blood glucose levels after overnight fasting were recorded using a commercially available glucometer and testing strips (One Touch Ultra, Life Scan Inc.) by tail vein bleeding at weekly intervals.

Kidney capsule transplantation and graft analysis. mSSC and BCSP populations were isolated as previously described. Cells were pelleted and resuspended in 2 μL of Growth Factor Reduced Matrigel (BD Biosciences). Equal numbers of each cell population were transplanted beneath separate kidney capsules of anaesthetized age- and gender-matched, non-diabetic immunodeficient mice. Kidneys were removed from host mice 4 weeks after transplantation and imaged. Grafts were dissected and fixed in 2% paraformaldehyde overnight at 4° C., decalcified in a 19% EDTA solution for 2 weeks at 4° C., and embedded in OCT or Paraffin for sectioning. Representative sections were stained with Movat's Pentachrome stain.

Transcriptional expression profiling and analysis. We performed microarray analyses on highly purified mSSC and BCSP populations isolated as previously described. In microarray studies, mSSC refers to mSSC/pre-BCSP (multipotent progenitor), as previously described. In single-cell RNA sequencing studies, mSSC refers to the mSSC alone. RNA was isolated with RNeasy Micro Kit (Qiagen) as per manufacturer's instructions. RNA was amplified twice with a RiboAmp RNA amplification kit (Arcturus Engineering). Amplified cRNA was streptavidin-labeled, fragmented, and hybridized to Affymetrix 430-2.0 arrays, as recommended by the manufacturer (Affymetrix). Arrays were scanned with a GeneChip Scanner 3000 (Affymetrix) running GCOS 1.1.1 software. Raw microarray data were submitted to Gene Expression Commons for normalization against the Common Reference, a large collection (n=11,939) of publicly available microarray data from the National Center for Biotechnology Information Gene Expression Omnibus (NCBI GEO). Meta-analysis of the Common Reference provides the dynamic range of each probe set. Where applicable, the probe set with the widest dynamic range was used. The Affymetrix Mouse Genome 430 2.0 Array includes 45,101 probe sets, of which 17,872 annotated genes are measurable. Heat maps representing fold change of gene expression were made in Gene Expression Commons.

Cell culture. Cells were maintained in vitro in Minimum Essential Media (MEM) with 10% FBS and 1% penicillin-streptomycin (Penstrep) under 2% $O_2$/7.5% $CO_2$. Each plate was coated with 0.1% gelatin. Cultured cells were lifted using collagenase II buffer (Sigma-Aldrich). For mSSC colony forming assays, cells were cultured for 2 weeks and colonies were counted using phase microscopy. The cells were lifted for staining and analysis by FACS. Osteogenic differentiation medium consisted of Dulbecco's Modified Eagle Medium with 10% FBS, 100 μg/ml ascorbic acid, and 10 mM-glycerophosphate. mSSCs isolated from P3, WT, and db mice were maintained in either regular media (MEM-alpha medium with 10% FBS, 1% Penstrep) or regular media supplemented with Ihh (R&D, 2.5 mg/mL), Shh (R&D, 500 pg/mL), or PBS under 2% $O_2$/7.5% $CO_2$ conditions. After 7 days, cells were lifted for staining and analysis by FACS or for RNA extraction and qRT-PCR.

ELISA of circulating cytokines. Serum levels of circulating cytokines were probed using commercially available kits, as per the manufacturer's instructions (SDF1a: R&D Systems; Osteocalcin: IBL America).

Luminex assay. Mouse serum was analyzed by the Human Immune Monitoring Center at Stanford University. Mouse 38 plex kits were purchased from eBiosciences/Affymetrix and used according to the manufacturer's instructions with noted modifications. Beads were added to a 96-well plate and washed in a Biotek ELx405 washer. Samples were added and incubated at room temperature (RT) for 1 hour followed by overnight incubation at 4° C. with shaking. Cold and RT incubation steps were performed on an orbital shaker at 500-600 rpm. Following overnight incubation, plates were washed and biotinylated detection antibody was added for 75 minutes at RT with shaking. The plate was washed again, and streptavidin-PE was added followed by incubation for 30 minutes at RT. The samples were washed again, and a reading buffer was added. Each sample was measured in duplicate. Plates were read using a Luminex 200 instrument with a lower bound of 50 beads per sample per cytokine. Custom assay control beads by Radix Biosolutions were added.

Parabiosis. Age- and sex-matched db (00697, Jackson Laboratories), WT (00664, Jackson Laboratories), or GFP (C57Bl/6, generated by Weissman laboratory) mice were paired 4 weeks prior to parabiosis. Chimeric pairs were generated as follows: WT/WT, db/db and WT/db. Mice are anesthetized with inhalational anesthesia. An incision from the base of the foreleg to the base of the hind-leg was made on the right side of one parabiont and the left side of the partner. The fore- and hind-legs were sutured together at the joints while the dorsal-dorsal, and ventral-ventral folds of the skin flaps were sutured together using horizontal mattress sutures to optimize size mismatch of the parabionts. Analgesia was administered. Blood chimerism was assessed using peripheral samples collected from tails after 2 weeks of parabiosis using FACS (if GFP+WT mouse used) or by local injection of Evan's blue dye and visualization of cross-circulation (if non-fluorescent WT mouse used). A peripheral blood chimerism of approximately 1:1 indicated full fusion of circulatory systems. Fractures were created upon blood chimerism.

Protein extraction from bone and immunoblotting. Dissected calluses were harvested and placed in liquid nitrogen. Using a pre-cooled mortar and pestle, individual tissue samples were ground to a fresh powder. Protein isolation was performed using cold RIPA buffer (50 mmol/L of HEPES, pH 7.5, 150 mmol/L of NaCl, 1 mmol/L of EDTA, 10% glycerol, 1% Triton-X-100, 25 mM NaF) containing 1 mM sodium orthovanadate and Proteases Inhibitor Cocktail (Sigma-Aldrich). Following repeated freeze-thaw cycles and sonication, samples were centrifuged and the supernatant was collected for protein quantification and western blot analysis. Total protein samples were prepared for loading with NuPAGE LDS sample buffer and NuPAGE reducing agent according to manufacturers instructions (NuPage, Life Technologies). Protein samples were electrophoresed on 4-20% Tris-HCl sodium dodecyl sulfate (SDS)-PAGE gels (Precast Criterion gels, Bio-Rad) and transferred onto Immobilon-P membrane (Millipore Corporation). Immunoblotting analysis was performed using primary rabbit antibodies of Indian hedgehog (ab52919, Abcam) and alpha-Tubulin (3873, Cell Signaling). A horseradish peroxidase-conjugated secondary anti-rabbit was used (1:2000; Cell Signaling). Immunoblotted proteins were visualized by enhanced chemiluminescence (Amersham Biosciences). Densitometry analysis of electrophoretic bands was performed using the ImageJ software program (NIH). Results are presented as mean±SEM of three independent experiments.

Quantitative reverse transcription polymerase chain reaction (qRT-PCR). RNA was isolated from cells using the RNeasy Mini kit (Qiagen) as per manufacturer's instructions. Reverse transcription was performed and gene expression was examined by qRT-PCR using the Applied biosystems Prism 7900HT sequence detection system (Applied Biosystems) and SYBR Green PCR Master Mix (Applied Biosystems). All values were normalized using glyceraldehyde 3-phosphate dehydrogenase for mouse samples and using beta-actin for human samples. Specific primer sequences for genes of interest were obtained from PrimerBank.

X-ray micro-computed tomography (micro-CT). Specimens were imaged using a calibrated X-ray micro-computed tomography unit (microXCT-200, Carl Zeiss X-ray Microscopy, Inc.) at 4× magnification with a peak voltage of 40 kVp, an LE #2 source filter, and a beam-hardening constant of 2. Reconstruction analysis was performed using XMReconstructor software (version 8.2.3724). Bone mineral density was determined using Avizo 9.0.0 post-processing software using the digital segmentation method as previously described (40).

What is claimed is:

1. A method of enhancing bone repair in a human individual with diabetes, the method comprising:
    selecting for treatment a human individual with diabetes and a hedgehog signaling deficiency in the skeletal stem cell niche response to bone injury or implant;
    administering to the individual within 7 days of a bone injury or orthopedic implant a localized drug delivery device at the site of bone injury or implant, the device releasing an effective dose of Indian Hedgehog protein for a period of time of not more than one week, to overcome the hedgehog signaling deficiency in the skeletal stem cell niche; wherein
    injury-induced expansion and osteogenic potential of skeletal stem cells is restored at the site and bone repair is enhanced at the site of bone injury or orthopedic implant.

2. The method of claim 1, wherein the individual has type 1 diabetes.

3. The method of claim 1, wherein the individual has type 2 diabetes.

4. The method of claim 1, wherein the localized drug delivery device is a sustained or localized release formulation.

5. The method of claim 4, wherein the formulation comprises a hydrogel.

6. The method of claim 1, further comprising administering to the individual an effective dose of skeletal stem cells or progenitors thereof.

7. The method of claim 1, further comprising administering porous or non-porous calcium phosphate, porous or non-porous hydroxyapatite, porous or non-porous tricalcium phosphate, porous or non-porous tetracalcium phosphate, porous or non-porous calcium sulfate, or a combination thereof.

8. The method of claim 1, further comprising administering an effective dose of a bioactive bone agent, comprising one or more of peptide growth factors, anti-inflammatory factors, pro-inflammatory factors, inhibitors of apoptosis, MMP inhibitors, bone catabolic antagonists.

9. A method of enhancing bone repair in a human individual with diabetes, the method comprising:
   selecting for treatment a human individual with diabetes and a hedgehog signaling deficiency in the skeletal stem cell niche response to bone injury or implant;
   administering to the individual, within 7 days of a bone injury or orthopedic implant, a localized drug delivery device at the site of bone injury or implant, the device releasing an effective dose of Indian Hedgehog (IHH) protein for a period of time of not more than one week, to overcome the hedgehog signaling deficiency in the skeletal stem cell niche;
   wherein the effective dose is one or more of:
      (a) the amount of IHH necessary to accelerate bone healing by at least 25%, relative to healing in the absence of IHH;
      (b) the amount of IHH necessary to increase the presence of skeletal stem cells (SSC) by at least about 25%, relative to healing in the absence of IHH;
      (c) the amount of IHH that provides for at least 0.1 µg/kg IHH protein;
   wherein injury-induced expansion and osteogenic potential of skeletal stem cells is restored at the site and bone repair is enhanced at the site of bone injury or orthopedic implant.

* * * * *